United States Patent
Allen et al.

(10) Patent No.: US 11,643,665 B2
(45) Date of Patent: May 9, 2023

(54) NUCLEOTIDE SEQUENCES ENCODING FASCIATED EAR3 (FEA3) AND METHODS OF USE THEREOF

(71) Applicants: CORTEVA AGRISCIENCE LLC, Indianapolis, IN (US); COLD SPRING HARBOR LABORATORY, Cold Spring Harbor, NY (US)

(72) Inventors: Stephen M Allen, Wilmington, DE (US); David Peter Jackson, Brooklyn, NY (US); Byoung Il Je, Oyster Bay, NY (US); Mai Komatsu, Indianapolis, IN (US); Young Koung Lee, East Norwich, NY (US); Hajime Sakai, Newark, DE (US)

(73) Assignees: CORTEVA AGRISCIENCE LLC, Indianapolis, IN (US); COLD SPRING HARBOR LABORATORY, Coldspring Harbor, NY (US)

( * ) Notice: Subject to any disclaimer, the term of this patent is extended or adjusted under 35 U.S.C. 154(b) by 220 days.

(21) Appl. No.: 16/783,613

(22) Filed: Feb. 6, 2020

(65) Prior Publication Data
US 2020/0157557 A1 May 21, 2020

Related U.S. Application Data

(63) Continuation of application No. 15/612,106, filed on Jun. 2, 2017, now Pat. No. 10,584,349, which is a continuation of application No. 14/384,692, filed as application No. PCT/US2013/030672 on Mar. 13, 2013, now Pat. No. 9,701,979.

(60) Provisional application No. 61/751,326, filed on Jan. 11, 2013, provisional application No. 61/610,645, filed on Mar. 14, 2012.

(51) Int. Cl.
C12N 15/82 (2006.01)

(52) U.S. Cl.
CPC ..... *C12N 15/8261* (2013.01); *C12N 15/8229* (2013.01); *C12N 15/8241* (2013.01)

(58) Field of Classification Search
None
See application file for complete search history.

(56) References Cited

U.S. PATENT DOCUMENTS

| | | | | |
|---|---|---|---|---|
| 7,179,963 | B2 * | 2/2007 | Bruce | C07K 14/415 435/71.1 |
| 9,701,979 | B2 * | 7/2017 | Allen | C12N 15/8261 |
| 10,584,349 | B2 * | 3/2020 | Allen | C12N 15/8261 |
| 2007/0011783 | A1 | 1/2007 | Liu et al. | |
| 2007/0020908 | A1 | 9/2007 | Wu et al. | |

FOREIGN PATENT DOCUMENTS

| | | |
|---|---|---|
| WO | 01/70987 A1 | 9/2001 |
| WO | 200170987 A2 | 9/2001 |

OTHER PUBLICATIONS

Tiedemann et al. Dissection of a complex seed phenotype: novel insights of FUSCA3 regulated developmental processes. Dev. Biol. May 1, 2008;317(1):1-12. Epub Feb. 13, 2008. (Year: 2008).*
Peter Bommert et al., thick tassel dwarf1 encodes a putative maize ortholog of the *Arabidopsis* CLAVATA1 eucine-rich repeat receptor-like kinase, Development, 2005, pp. 1235-1245, vol. 132.
Jennifer C. Fletcher et al., Signaling of Cell Fate Decisions by CLAVAT3 in *Arabidopsis* Shoot Meristems, Science, Mar. 19, 1999, pp. 1911-1914, vol. 283.
Thomas R. Mertens et al., The Morphology, Anatomy, and Genetics of a Stem Fasciation in Lycopersicon esculentum, American Journal of Botany, Nov. 1954, p. 726-732, vol. 41, No. 9.
Zugene J. Szymkowiak et al., The Internal Meristem Layer (L3) Determines Floral Meristem Size and Carpel Number in Tomato Periclinal Chimeras, The Plant Cell, Sep. 1992, pp. 1089-1100, vol. 4.
Funio Taguchi-Shiobara et al., The fascinated ear2 gene encodes a leucine-rich repeat receptor-like protein that regulates shoot meristem proliferation in maize, Genes & Development, 2001, pp. 2755-2766, vol. 15.
Amy E. Trotochaud et al., The CLAVATA1 Receptor-like Kinase Requires CLAVATA3 for Its Assembly into a Signaling Complex That Includes KAPP and a Rho-Related Protein, The Plant Cell, Mar. 1999, pp. 393-405, vol. 11.
Yonghong Wang et al., Genes controlling plant architecture, Current Opinion in Biotechnology, 2006, pp. 123-129, vol. 17.
Etsuo Yamamoto et al., Molecular characterization of two soybean homologs of *Arabidopsis thaliana* CLAVAT1 from the wild type and fasciation mutant1, Biochimica et Biophysica Acta, 2000, pp. 333-340, vol. 1491.
UniProt ID Q9CA41_ARATH, Jun. 1, 2001.
UnitProt ID Q5PP26_ARATH (PII2_ARATH), Jan. 4, 2005.
UniProt ID No. F4JA38_ARATH Jun. 28, 2011.
UniProt ID No. C5XEWS_SORBI Sep. 1, 2009.
UniProt ID No. C5XEW7_SORBI Sep. 1, 2009.
UniProt ID No. K7LKJ4_SOYBN Jan. 9, 2013.
UniProt ID No. I1NHK5_SOYBN Jun. 13, 2012.
UniProt ID No. K7K7H6_SOYBN Jan. 9, 2013.
UniProt ID No. K7K2T2_SOYBN Jan. 9, 2013.
UniProt ID No. I1K192_SOYBN Jun. 13, 2012.
UniProt ID No. I1MUH6_SOYBN Jun. 13, 2012.
UniProt ID No. q0dgx0_orysj Oct. 17, 2006.
International Search Report—PCT/US2013/030672—dated Jun. 26, 2013.

* cited by examiner

*Primary Examiner* — Cynthia E Collins

(57) ABSTRACT

Methods and compositions for modulating shoot apical meristem size are provided. Methods are provided for modulating the expression of fea3 sequence in a host plant or plant cell to modulate agronomic characteristics such as altered size and number of organs, including plant seeds.

4 Claims, 8 Drawing Sheets

Specification includes a Sequence Listing.

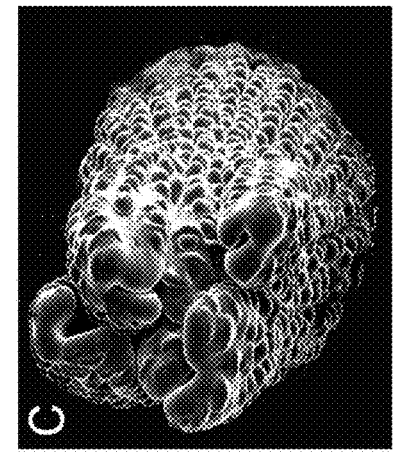
FIG. 3B
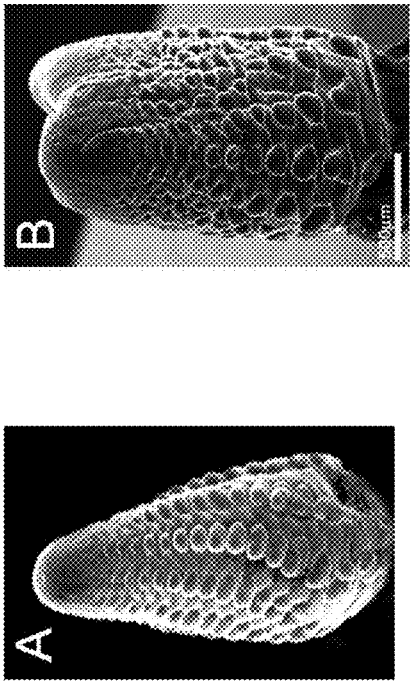
FIG. 3C
FIG. 3A
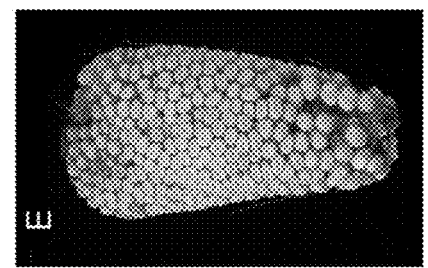
FIG. 3E
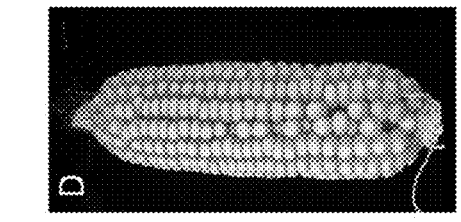
FIG. 3D

NUCLEOTIDE SEQUENCES ENCODING FASCIATED EAR3 (FEA3) AND METHODS OF USE THEREOF

CROSS REFERENCE TO RELATED APPLICATIONS

This application is a continuation application of U.S. Ser. No. 15/612,106, filed on Jun. 2, 2017, which is a continuation application of U.S. Ser. No. 14/384,692, filed Sep. 12, 2014, now U.S. Pat. No. 9,701,979, which is a National Stage Application of PCT/US2013/030672, filed Mar. 13, 2013, which claims the benefit of U.S. Provisional Application No. 61/610,645, filed Mar. 14, 2012, and U.S. Provisional Application No. 61/751,326, filed Jan. 11, 2013, the entire content of each is herein incorporated by reference.

FIELD OF THE INVENTION

The invention relates to the field of the genetic manipulation of plants, particularly the modulation of gene activity and development in plants.

BACKGROUND OF THE INVENTION

Leaves and the axillary meristems that generate branches and flowers are initiated in regular patterns from the shoot apical meristem (SAM). The cells of the shoot apical meristem summit serve as stem cells that divide to continuously displace daughter cells to the surrounding regions, where they are incorporated into differentiated leaf or flower primordia. The meristems are thus capable of regulating their size during development by balancing cell proliferation with the incorporation of cells into new primordia. The SAM provides all aerial parts of plant body. The central concept of stem cells regulation is known by the signal pathway of CLAVATA/WUSCHEL (CLV/WUS) genes. Loss of CLV1, CLV2, or CLV3 activity in *Arabidopsis* causes accumulation of undifferentiated cells in the shoot apex, indicating that CLV genes together promote the timely transition of stem cells into differentiation pathways, or repress stem cell division, or both (Fletcher et al. (1999) *Science* 283:1911-1914; Taguchi-Shiobara et al. (2001) *Genes and Development* 15:2755-5766; Trotochaud et al. (1999) *Plant Cell* 11:393-405; Merton et al. (1954) *Am. J. Bot.* 41:726-32; Szymkowiak et al. (1992) *Plant Cell* 4:1089-100; Yamamoto et al. (2000) *Biochim. Biophys. Acta.* 1491:333-40). The maize orthologue of CLV1 is TD1 (Bommert et al. (2005) Development 132:1235-1245). The maize orthologue of CLV2 is FEA2 (Taguchi-Shiobara et al. (2001) *Genes Dev.* 65 15:2755-2766). It is desirable to be able to control the size and appearance of shoot and floral meristems, to give increased yields of leaves, flowers, and fruit. Accordingly, it is an object of the invention to provide novel methods and compositions for the modulation of meristem development.

SUMMARY OF THE INVENTION

In one embodiment, the current invention provides a method of producing a transgenic plant with decreased expression of endogenous fea3, the method comprising the steps of (a) introducing into a regenerable plant cell a recombinant construct comprising a polynucleotide sequence operably linked to a promoter, wherein the expression of the polynucleotide sequence reduces endogenous fea3 expression; (b) regenerating a transgenic plant from the regenerable plant cell after step (a), wherein the transgenic plant comprises in its genome the recombinant DNA construct; and (c) selecting a transgenic plant of (b), wherein the transgenic plant comprises the recombinant DNA construct and exhibits a decrease in expression of fea3, when compared to a control plant not comprising the recombinant DNA construct.

In another embodiment, the current invention provides a method of producing a transgenic plant with decreased expression of endogenous fea3, the method comprising the steps of (a) introducing into a regenerable plant cell a recombinant DNA construct comprising an isolated polynucleotide operably linked, in sense or antisense orientation, to a promoter functional in a plant, wherein the polynucleotide comprises: (i) the nucleotide sequence of SEQ ID NO:1, 2 or 4; (ii) a nucleotide sequence with at least 90% sequence identity, based on the Clustal W method of alignment, when compared to SEQ ID NO:1, 2 or 4; (iii) a nucleotide sequence of at least 100 contiguous nucleotides of SEQ ID NO:1, 2 or 4; (iv) a nucleotide sequence that can hybridize under stringent conditions with the nucleotide sequence of (i); or (v) a modified plant miRNA precursor, wherein the precursor has been modified to replace the miRNA encoding region with a sequence designed to produce a miRNA directed to SEQ ID NO:1, 2 or 4; (b) regenerating a transgenic plant from the regenerable plant cell after step (a), wherein the transgenic plant comprises in its genome the recombinant DNA construct; and (c) selecting a transgenic plant of (b), wherein the transgenic plant comprises the recombinant DNA construct and exhibits a decrease in expression of fea3, when compared to a control plant not comprising the recombinant DNA construct.

One embodiment of the invention is a method of producing a transgenic plant with alteration of an agronomic characteristic, the method comprising the steps of (a) introducing into a regenerable plant cell a recombinant DNA construct comprising an isolated polynucleotide operably linked to at least one regulatory sequence, wherein the polynucleotide encodes a fragment or a variant of a polypeptide having an amino acid sequence of at least 80% sequence identity, based on the Clustal W method of alignment, when compared to SEQ ID NO:3 or 5, wherein the fragment or the variant confers a dominant-negative phenotype in the regenerable plant cell; (b) regenerating a transgenic plant from the regenerable plant cell after step (a), wherein the transgenic plant comprises in its genome the recombinant DNA construct; and (c) selecting a transgenic plant of (b), wherein the transgenic plant comprises the recombinant DNA construct and exhibits an alteration of at least one agronomic characteristic selected from the group consisting of: ear meristem size, kernel row number, leaf number, inflorescence number, branching within the inflorescence, flower number, fruit number, seed number, root branching, root biomass, root lodging, biomass and yield, when compared to a control plant not comprising the recombinant DNA construct.

Another embodiment of the current invention is the above method wherein expression of the polypeptide of part (a) in a plant line having the fea3 mutant genotype is capable of partially or fully restoring the wild-type phenotype.

One embodiment of the current invention is a method of identifying a weaker allele of fea3, the method comprising the steps of (a) performing a genetic screen on a population of mutant maize plants (b) identifying one or more mutant maize plants that exhibit weak fea3 phenotype than a fea3 null plant; and (c) identifying the weak fea3 allele from the mutant maize plant with weaker fea3 phenotype.

One embodiment of the current invention is a method of identifying a weaker allele of fea3, the method comprising the steps of: (a) gene shuffling using SEQ ID NOS:1, 2 or 4; (b) transforming the shuffled sequences from step (a) into a population of regenerable plant cells; (c) regenerating a population of transformed plants from the population of transformed regenerable plant cells of step (b); (d) screening the population of transformed plants from step (c) for weak fea3 phenotype; and (e) identifying the weak fea3 allele from the transformed plant exhibiting weak fea3 phenotype.

One embodiment of the invention is a plant in which expression of the endogenous fea3 gene is inhibited relative to a control plant. Another embodiment of the current invention is a method of making said plant, the method comprising the steps of (a) introducing a mutation into the endogenous fea3 gene; and (b) detecting the mutation, wherein the mutation is effective in inhibiting the expression of the endogenous fea3 gene. In one embodiment, the steps (a) and (b) are done using Targeting Induced Local Lesions IN Genomics (TILLING) method. In embodiment, the mutation is a site-specific mutation.

One embodiment of the invention is a plant that exhibits weaker fea3 phenotype relative to a wild-type plant. Another embodiment is a method of making said plant wherein the method comprises the steps of: (a) introducing a transposon into a germ plasm containing an endogenous fea3 gene; (b) obtaining progeny of the germplasm of step (a); (c) and identifying a plant of the progeny of step (b) in which the transposon has inserted into the endogenous FEA3 gene and a reduction of expression of fea3 is observed. Step (a) may further comprise introduction of the transposon into a regenerable plant cell of the germ plasm by transformation and regeneration of a transgenic plant from the regenerable plant cell, wherein the transgenic plant comprises in its genome the transposon.

In one embodiment, the methods described above wherein the method further comprises the steps of (a) introducing into a regenerable plant cell a recombinant construct comprising the weak fea3 allele identified by the methods described above; (b) regenerating a transgenic plant from the regenerable plant cell after step (a), wherein the transgenic plant comprises in its genome the recombinant DNA construct; and (c) selecting a transgenic plant of (b), wherein the transgenic plant comprises the recombinant DNA construct and exhibits a weak fea3 phenotype, when compared to a control plant not comprising the recombinant DNA construct.

Another embodiment is a method of producing a transgenic plant with an alteration in agronomic characteristic, the method comprising (a) introducing into a regenerable plant cell a recombinant DNA construct comprising an isolated polynucleotide operably linked, in sense or antisense orientation, to a promoter functional in a plant, wherein the polynucleotide comprises: (i) the nucleotide sequence of SEQ ID NO:1, 2 or 4; (ii) a nucleotide sequence with at least 90% sequence identity, based on the Clustal W method of alignment, when compared to SEQ ID NO:1, 2 or 4; (iii) a nucleotide sequence of at least 100 contiguous nucleotides of SEQ ID NO:1, 2 or 4; (iv) a nucleotide sequence that can hybridize under stringent conditions with the nucleotide sequence of (i); or (v) a modified plant miRNA precursor, wherein the precursor has been modified to replace the miRNA encoding region with a sequence designed to produce a miRNA directed to SEQ ID NO:1, 2 or 4; (b) regenerating a transgenic plant from the regenerable plant cell after step (a), wherein the transgenic plant comprises in its genome the recombinant DNA construct; and (c) selecting a transgenic plant of (b), wherein the transgenic plant comprises the recombinant DNA construct and exhibits an alteration in at least one agronomic characteristic selected from the group consisting of: enlarged ear meristem, kernel row number, seed number, root branching, root biomass, root lodging, biomass and yield, when compared to a control plant not comprising the recombinant DNA construct. Another embodiment is the plant produced by this method.

One embodiment is a method of expressing a heterologous polynucleotide in a plant, the method comprising (a) transforming a regenerable plant cell with a recombinant DNA construct comprising a heterologous polynucleotide operably linked to a second polynucleotide, wherein the second polynucleotide is a FEA3 promoter (b) regenerating a transgenic plant from the regenerable plant cell after step (a), wherein the transgenic plant comprises in its genome the recombinant DNA construct; and (c) selecting a transgenic plant of (b), wherein the transgenic plant comprises the recombinant DNA construct and further wherein the heterologous polynucleotide is expressed in the transgenic plant. Another embodiment is the plant comprising in its genome a recombinant DNA construct comprising a heterologous polynucleotide operably linked to a second polynucleotide, wherein the second polynucleotide is a FEA3 promoter and wherein the heterologous polynucleotide is expressed in the plant.

Another embodiment is a method of identifying a first maize plant or a first maize germplasm that has an alteration of at least one agronomic characteristic, the method comprising detecting in the first maize plant or the first maize germplasm at least one polymorphism of a marker locus that is associated with said phenotype, wherein the marker locus encodes a polypeptide comprising an amino acid sequence selected from the group consisting of: a) an amino acid sequence having at least 90% and less than 100% sequence identity to SEQ ID NO:3 or 5, wherein expression of said polypeptide in a plant or plant part thereof results in an alteration of at least one agronomic characteristic selected from the group consisting of: ear meristem size, kernel row number, inflorescence number, branching within the inflorescence, flower number, fruit number, and seed number, when compared to a control plant, wherein the control plant comprises SEQ ID NO:3 or 5. Another embodiment is the above method wherein said polypeptide comprises the sequence set forth in SEQ ID NO:23, 25 or 27.

The invention includes a recombinant DNA construct comprising an isolated polynucleotide of the current invention operably linked, in sense or antisense orientation, to a promoter that is shoot apical meristem specific or shoot apical meristem preferred.

This invention includes a vector, cell, plant, or seed comprising any of the recombinant DNA constructs described in the present invention.

The invention encompasses plants produced by the methods described herein.

The invention also encompasses regenerated, mature and fertile transgenic plants comprising the recombinant DNA constructs described above, transgenic seeds produced therefrom, T1 and subsequent generations. The transgenic plant cells, tissues, plants, and seeds may comprise at least one recombinant DNA construct of interest.

In one embodiment, the plant is selected from the group consisting of: *Arabidopsis*, tomato, maize, soybean, sunflower, sorghum, canola, wheat, alfalfa, cotton, rice, barley, millet, sugar cane and switchgrass.

In one embodiment, the plant comprising the recombinant constructs described in the present invention is a monocotyledonous plant. In another embodiment, the plant comprising the recombinant constructs described in the present invention is a maize plant.

BRIEF DESCRIPTION OF THE DRAWINGS AND SEQUENCE LISTINGS

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. § 1.822.

FIG. 1 shows the map-based cloning approach used to isolate the fea3-Reference allele.

FIG. 2A shows RT-PCR data showing the expression analysis of fea2 and fea3 in different tissues. The different tissues analyzed are RAM: root apical meristem; RE: root elongation zone; RAM(l): RAM of lateral root; SAM; shoot apical meristem (including leaf primordia); EM: ear inflorescence meristem FIG. 2B shows fea3 expression in situ. FIG. 2C shows western blot with anti-RFP antibody of RFP-tagged FEA3, of membrane fractionated samples from non-transgenic WT and transgenic plants expressing RFP tagged FEA3 protein. "T" is the "total, unfractionated sample", "S" is the soluble fraction and "M" is the membrane fraction.

FIG. 3B-3E shows the fasciated fea3 phenotype in ear development compared to that in a wild-type (wt) plant (FIG. 3A).

Figure 4B:
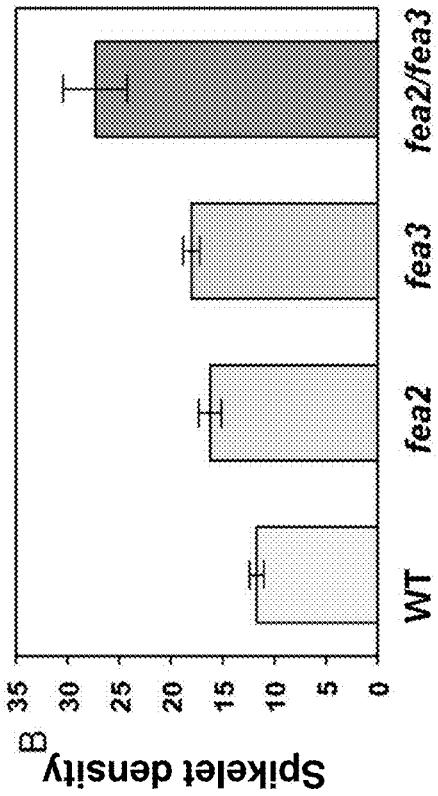
FIG. 4A-4C show the phenotypic analysis of fea3/fea2 double mutants.
Figure 4A:
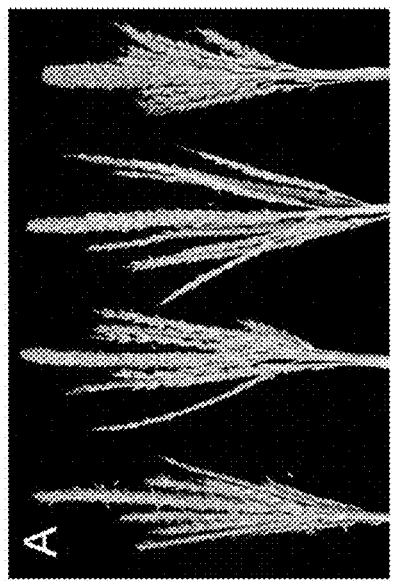
Figure 4C:
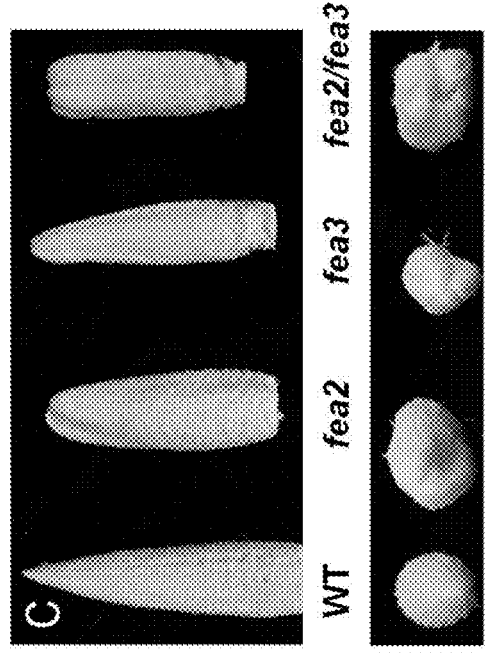

FIG. 4A shows the comparison between the tassels of double mutants compared to single mutants and wt plants. FIG. 4B shows the spikelet density comparison between double mutants, single mutants and wt plants. FIG. 4C shows a comparison between double mutant ear phenotypes compared to single mutants and wt plants.

Figures 5A, 5B:
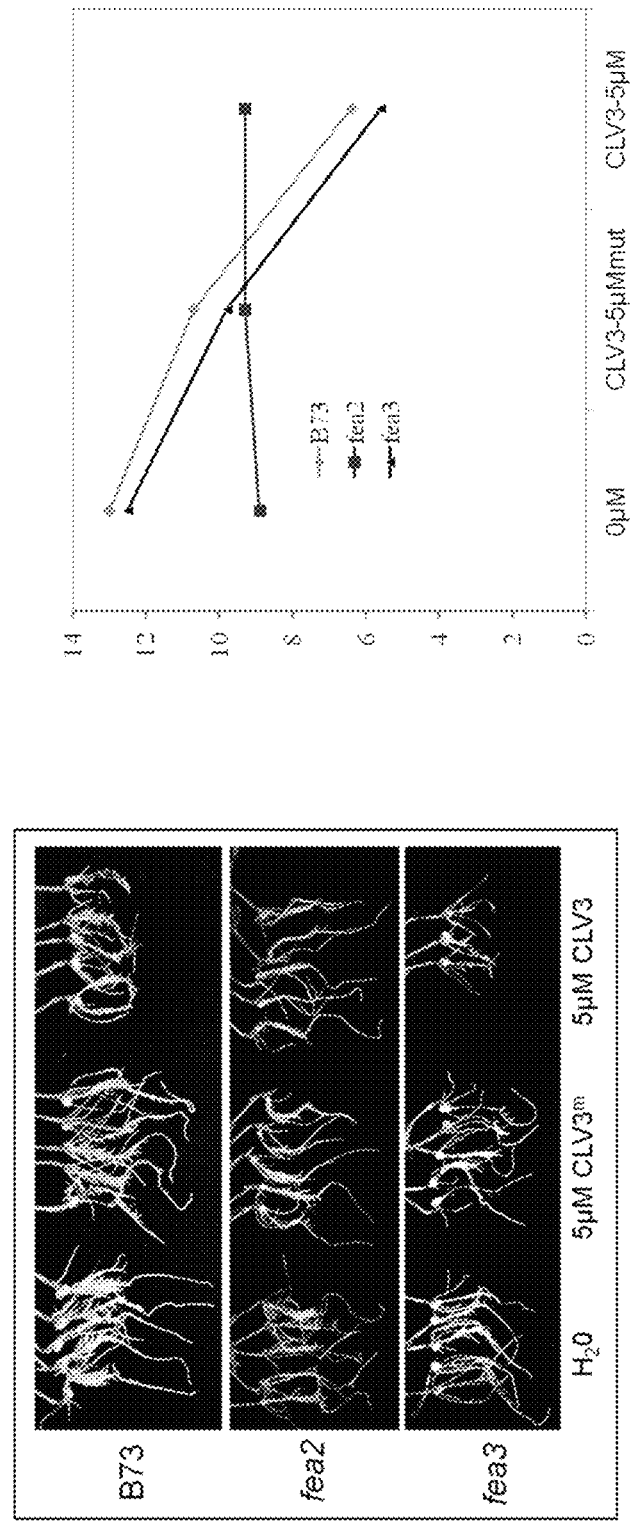

FIG. 5A and FIG. 5B shows a comparison between wt plants, fea2 and fea3 plants in the CLV3 peptide root assay. FIG. 5B shows the quantitative analysis.

Figure 6:
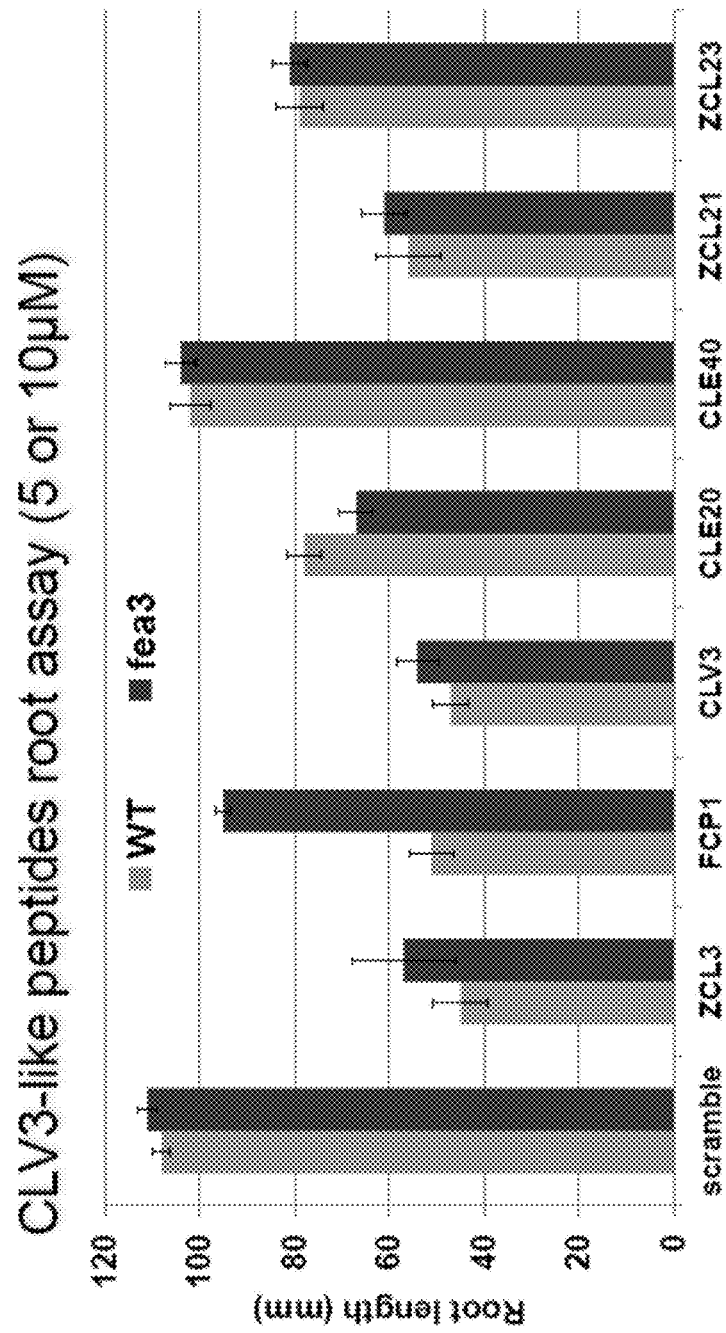

FIG. 6 shows a quantitative analysis of the comparison between wt plants, fea2 and fea3 plants in the CLV3-like peptide root assay.

Figure 7B:
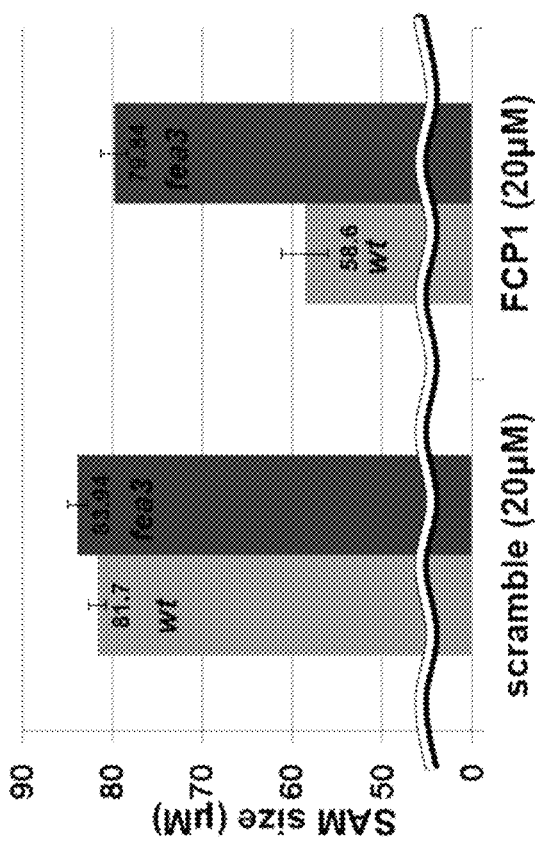
Figure 7A:
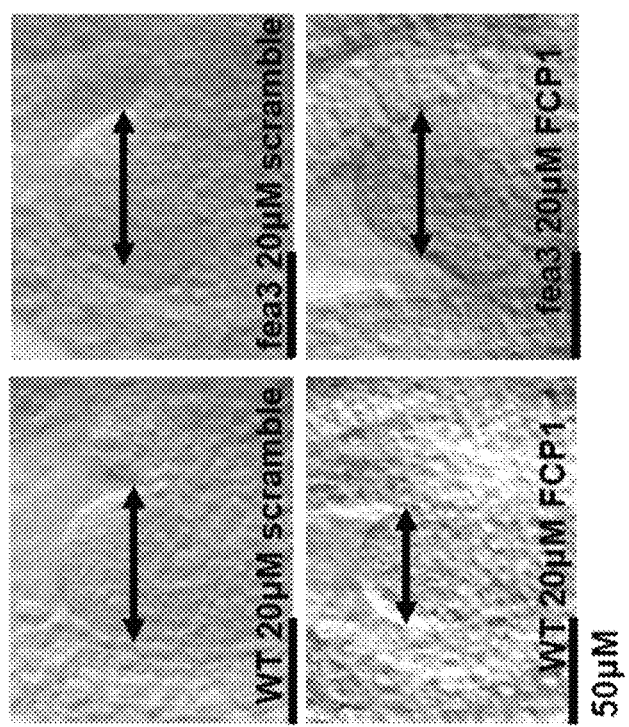

FIG. 7A and FIG. 7B shows wt and fea3 embryos cultured in the presence of FCP1 and scrambled peptide. FIG. 7A shows wt and fea3 embryo SAM growth, and FIG. 7B shows a quantitative analysis of the same.

Figure 8B:
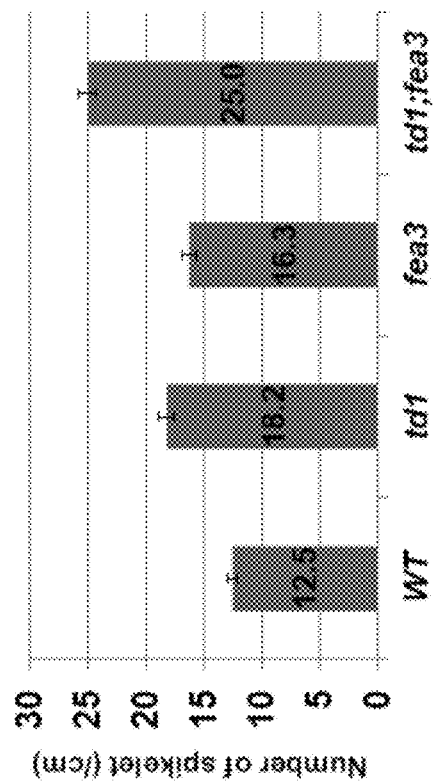
Figure 8A:
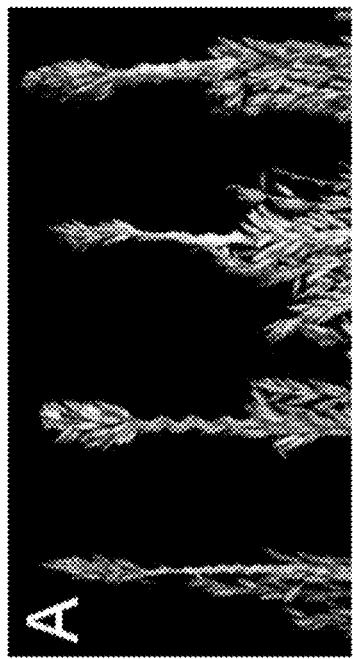
Figure 8C:
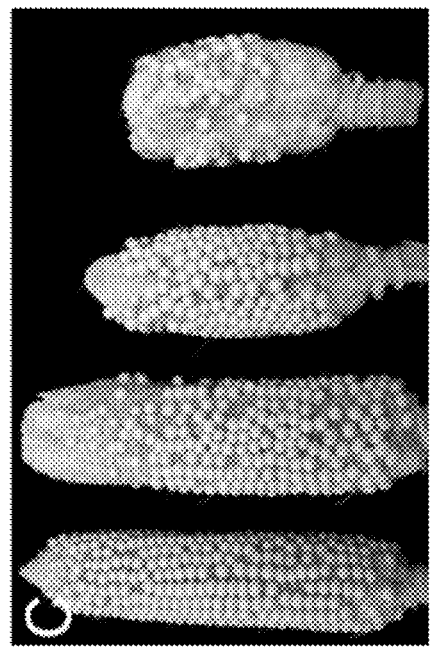
Figure 8C:
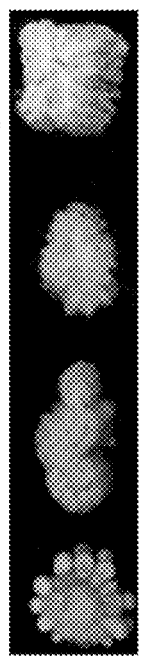

FIG. 8A-8C show the phenotypic analysis of fea3/td1 double mutants.

The sequence descriptions (Table 1) and Sequence Listing attached hereto comply with the rules governing nucleotide and/or amino acid sequence disclosures in patent applications as set forth in 37 C.F.R. § 1.821-1.825. The Sequence Listing contains the one letter code for nucleotide sequence characters and the three letter codes for amino acids as defined in conformity with the IUPAC-IUBMB standards described in Nucleic Acids Res. 13:3021-3030 (1985) and in the Biochemical J. 219 (2):345-373 (1984) which are herein incorporated by reference. The symbols and format used for nucleotide and amino acid sequence data comply with the rules set forth in 37 C.F.R. § 1.822.

SEQ ID NO:1 is the nucleotide sequence of the fea3 wt gene.

SEQ ID NO:2 is the coding sequence of wt fea3.

SEQ ID NO:3 is the amino acid sequence of wt fea3.

SEQ ID NO:4 is the coding sequence of alternatively spliced shorter fea3.

SEQ ID NO:5 is the amino acid sequence of alternatively spliced shorter fea3.

SEQ ID NO:6 is the amino acid sequence encoded by the nucleotide sequence corresponding to the locus At1g68780 (*Arabidopsis thaliana*).

SEQ ID NO:7 is the amino acid sequence encoded by the nucleotide sequence corresponding to the locus At1g13230 (*Arabidopsis thaliana*).

SEQ ID NO:8 is the amino acid sequence encoded by the nucleotide sequence corresponding to the locus At3g25670 (*Arabidopsis thaliana*).

SEQ ID NO:9 is the amino acid sequence corresponding to the locus LOC_Os05g43140.1, a rice (*japonica*) predicted protein from the Michigan State University Rice Genome Annotation Project Osa1 release 6 (January 2009).

SEQ ID NO:10 is the amino acid sequence corresponding to Sb03g008380, a sorghum (*Sorghum bicolor*) predicted protein from the Sorghum JGI genomic sequence version 1.4 from the US Department of energy Joint Genome Institute.

SEQ ID NO:11 is the amino acid sequence corresponding to Sb03g008360, a sorghum (*Sorghum bicolor*) predicted protein from the Sorghum JGI genomic sequence version 1.4 from the US Department of energy Joint Genome Institute.

SEQ ID NO:12 is the amino acid sequence corresponding to Glyma20g32610, a soybean (*Glycine max*) predicted protein from predicted coding sequences from Soybean JGI Glyma1.01 genomic sequence from the US Department of energy Joint Genome Institute.

SEQ ID NO:13 is the amino acid sequence corresponding to Glyma10g34950, a soybean (*Glycine max*) predicted protein from predicted coding sequences from Soybean JGI Glyma1.01 genomic sequence from the US Department of energy Joint Genome Institute.

SEQ ID NO:14 is the amino acid sequence corresponding to Glyma02g11350, a soybean (*Glycine max*) predicted protein from predicted coding sequences from Soybean JGI Glyma1.01 genomic sequence from the US Department of energy Joint Genome Institute.

SEQ ID NO:15 is the amino acid sequence corresponding to Glyma01g22730, a soybean (*Glycine max*) predicted protein from predicted coding sequences from Soybean JGI Glyma1.01 genomic sequence from the US Department of energy Joint Genome Institute.

SEQ ID NO:16 is the amino acid sequence corresponding to Glyma05g07800, a soybean (*Glycine max*) predicted protein from predicted coding sequences from Soybean JGI Glyma1.01 genomic sequence from the US Department of energy Joint Genome Institute.

SEQ ID NO:17 is the amino acid sequence corresponding to Glyma17g13210, a soybean (*Glycine max*) predicted protein from predicted coding sequences from Soybean JGI Glyma1.01 genomic sequence from the US Department of energy Joint Genome Institute.

SEQ ID NO:18 is the nucleotide sequence of a fea3 homolog from *Ascelpias syriaca*.

SEQ ID NO:19 is the amino acid sequence encoded by the nucleotide sequence of SEQ ID NO:18.

SEQ ID NO:20 is the nucleotide sequence of fea3-0 reference allele.

SEQ ID NO:21 is the protein sequence of fea3-0 reference allele, encoded by SEQ ID NO:20.

SEQ ID NO:22 is the nucleotide sequence of the EMS mutant fea3-1.

SEQ ID NO:23 is the protein sequence of the EMS mutant allele fea3-1, encoded by the nucleotide sequence given in SEQ ID NO:22.

SEQ ID NO:24 is the nucleotide sequence of the EMS mutant fea3-2.

SEQ ID NO:25 is the protein sequence of the EMS mutant allele fea3-2, encoded by the nucleotide sequence given in SEQ ID NO:24.

SEQ ID NO:26 is the nucleotide sequence of the EMS mutant fea3-3.

SEQ ID NO:27 is the protein sequence of the EMS mutant allele fea3-3, encoded by the nucleotide sequence given in SEQ ID NO:26.

SEQ ID NO:28 is the nucleotide sequence of the FEA3 promoter.

SEQ ID NO:29 is the nucleotide sequence encoding the signal peptide of the FEA3 protein.

SEQ ID NO:30 is the nucleotide sequence encoding the RFP-FEA3 fusion protein.

SEQ ID NO:31 is the nucleotide sequence of the FEA3 3'-UTR.

SEQ ID NOS:32-38 are the sequences of the peptides (ZCL3, FCP1, CLV3, CLE20, CLE40, ZCL21 and ZCL23 respectively) used for the CLV3/CLV3-like peptide assay described in Example 10.

The sequence descriptions and Sequence Listing attached hereto comply with the rules governing nucleotide and/or amino acid sequence disclosures in patent applications as set forth in 37 C.F.R. § 1.821-1.825.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. § 1.822.

DETAILED DESCRIPTION OF THE INVENTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, or by agricultural observations such as osmotic stress tolerance or yield.

"Agronomic characteristic" is a measurable parameter including but not limited to, ear meristem size, tassel size, greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root branching, root biomass, root lodging, harvest index, stalk lodging, plant height, ear height, ear length, salt tolerance, early seedling vigor and seedling emergence under low temperature stress.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

"Coding region" refers to a polynucleotide sequence that when transcribed, processed, and/or translated results in the production of a polypeptide sequence.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Overexpression" refers to the production of a gene product in transgenic organisms that exceeds levels of production in a null segregating (or non-transgenic) organism from the same experiment.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A "favorable allele" is the allele at a particular locus that confers, or contributes to, a desirable phenotype, e.g., increased cell wall digestibility, or alternatively, is an allele that allows the identification of plants with decreased cell wall digestibility that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches. Silencing may be targeted to coding regions or non-coding regions, e.g., introns, 5'-UTRs and 3'-UTRs, or both.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al., *Plant J.* 16:651-659 (1998); and Gura, *Nature* 404:804-808 (2000)). Cosuppression constructs may contain sequences from coding regions or non-coding regions, e.g., introns, 5'-UTRs and 3'-UTRs, or both.

Another variation describes the use of plant viral sequences to direct the suppression of proximal mRNA encoding sequences (PCT Publication No. WO 98/36083 published on Aug. 20, 1998).

RNA interference refers to the process of sequence-specific post-transcriptional gene silencing in animals mediated by short interfering RNAs (siRNAs) (Fire et al., *Nature* 391:806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 (1999)).

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to about 24 nucleotides (nt) in length that have been identified in both animals and plants (Lagos-Quintana et al., *Science* 294:853-858 (2001), Lagos-Quintana et al., *Curr. Biol.* 12:735-739 (2002); Lau et al., *Science* 294:858-862 (2001); Lee and Ambros, *Science* 294:862-864 (2001); Llave et al., *Plant Cell* 14:1605-1619 (2002); Mourelatos et al., *Genes. Dev.* 16:720-728 (2002); Park et al., *Curr. Biol.* 12:1484-1495 (2002); Reinhart et al., *Genes. Dev.* 16:1616-1626 (2002)). They are processed from longer precursor transcripts that range in size from approximately 70 to 200 nt, and these precursor transcripts have the ability to form stable hairpin structures.

MicroRNAs (miRNAs) appear to regulate target genes by binding to complementary sequences located in the transcripts produced by these genes. It seems likely that miRNAs can enter at least two pathways of target gene regulation: (1) translational inhibition; and (2) RNA cleavage. MicroRNAs entering the RNA cleavage pathway are analogous to the 21-25 nt short interfering RNAs (siRNAs) generated during RNA interference (RNAi) in animals and posttranscriptional gene silencing (PTGS) in plants, and likely are incorporated into an RNA-induced silencing complex (RISC) that is similar or identical to that seen for RNAi.

The term "locus" generally refers to a genetically defined region of a chromosome carrying a gene or, possibly, two or more genes so closely linked that genetically they behave as a single locus responsible for a phenotype. When used herein with respect to Fea3, the "Fea3 locus" shall refer to the defined region of the chromosome carrying the Fea3 gene including its associated regulatory sequences.

A "gene" shall refer to a specific genetic coding region within a locus, including its associated regulatory sequences. One of ordinary skill in the art would understand that the associated regulatory sequences will be within a distance of about 4 kb from the Fea3 coding sequence, with the promoter located upstream.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leaves, stems, pollen, or cells, that can be cultured into a whole plant.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal W method of alignment.

The Clustal W method of alignment (described by Higgins and Sharp, CABIOS. 5:151-153 (1989); Higgins, D. G. et al., Comput. Appl. Biosci. 8:189-191 (1992)) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB.

After alignment of the sequences, using the Clustal W program, it is possible to obtain "percent identity" and "divergence" values by viewing the "sequence distances" table on the same program; unless stated otherwise, percent identities and divergences provided and claimed herein were calculated in this manner.

The present invention includes the following isolated polynucleotides and polypeptides:

An isolated polynucleotide comprising: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal W method of alignment, when compared to SEQ ID NO:3, 5, 6, 7, 8, 9, 10, 11, 12, 13, 14, 15, 16, 17, 19, 21, 23, 25 or 27; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs (including suppression DNA constructs) of the present invention. The polypeptide is preferably a FEA3 polypeptide. The polypeptide preferably has FEA3 activity.

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal W method of alignment, when compared to SEQ ID NO:3, 5, 6, 7, 8, 9, 10, 11, 12, 13, 14, 15, 16, 17, 19, 21, 23, 25 or 27. The polypeptide is preferably a FEA3 polypeptide. The polypeptide preferably has FEA3 activity.

An isolated polynucleotide comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal W method of alignment, when compared to SEQ ID NO:1, 2, 4, 18, 20, 22, 24 or 26; or (ii) a full complement of the nucleic acid sequence of (i). Any of the foregoing isolated polynucleotides may be utilized in any recombinant DNA constructs (including suppression DNA constructs) of the present invention. The polypeptide is preferably a FEA3 polypeptide. The polypeptide preferably has FEA3 activity.

An isolated polynucleotide comprising a nucleotide sequence, wherein the nucleotide sequence is hybridizable under stringent conditions with a DNA molecule comprising the full complement of SEQ ID NO:1, 2, 4, 18, 20, 22, 24 or 26. The polypeptide is preferably a FEA3 polypeptide. The polypeptide preferably has FEA3 activity.

An isolated polynucleotide comprising a nucleotide sequence, wherein the nucleotide sequence is derived from SEQ ID NO:1, 2, 4, 18, 20, 22, 24 or 26 by alteration of one or more nucleotides by at least one method selected from the group consisting of: deletion, substitution, addition and insertion. The polypeptide is preferably a FEA3 polypeptide. The polypeptide preferably has FEA3 activity.

An isolated polynucleotide comprising a nucleotide sequence, wherein the nucleotide sequence corresponds to an allele of SEQ ID NO:1, 2, 4, 18, 20, 22, 24 or 26.

In one embodiment, the present invention includes recombinant DNA constructs (including suppression DNA constructs). The recombinant DNA construct (including suppression DNA constructs) may comprise a polynucleotide of the present invention operably linked, in sense or antisense orientation, to at least one regulatory sequence (e.g., a promoter functional in a plant). The polynucleotide may comprise 100, 200, 300, 400, 500, 600, 700, 800, 900 or 1000 contiguous nucleotides of SEQ ID NO:1, 2, 4, 18, 20, 22, 24 or 26. The polynucleotide may encode a polypeptide of the present invention.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

It is well understood by those skilled in the art that different promoters may direct the expression of a gene in different tissues or cell types, or at different stages of development, or in response to different environmental conditions.

Promoters that can be used for this invention include, but are not limited to, shoot apical meristem specific promoters and shoot apical meristem preferred promoters. Maize knotted 1 promoter, and promoters from genes that are known to be expressed in maize SAM can be used for expressing the polynucleotides disclosed in the current invention. Examples of such genes include, but are not limited to Zm phabulosa, terminal ear1, rough sheath2, rolled leaf1, zyb14, narrow sheath (Ohtsu, K. et al (2007) *Plant Journal* 52, 391-404). Promoters from orthologs of these genes from other species can be also be used for the current invention.

Examples of *Arabidopsis* promoters from genes with SAM-preferred expression include, but are not limited to, clv3, aintegumenta-like (ail5, ail6, and ail7) and terminal ear like1, clavata1, wus, shootmeristemless, terminal flower1 (Yadav et al (2009) *Proc Natl Acad Sci USA*. March 24).

PCT Publication Nos. WO 2004/071467 and U.S. Pat. No. 7,129,089 describe the synthesis of multiple promoter/gene/terminator cassette combinations by ligating individual promoters, genes, and transcription terminators together in unique combinations. Generally, a NotI site flanked by the suitable promoter is used to clone the desired gene. NotI sites can be added to a gene of interest using PCR amplification with oligonucleotides designed to introduce NotI sites at the 5' and 3' ends of the gene. The resulting PCR product is then digested with NotI and cloned into a suitable promoter/NotI/terminator cassette. Although gene cloning into expression cassettes is often done using the NotI restriction enzyme, one skilled in the art can appreciate that a number of restriction enzymes can be utilized to achieve the desired cassette. Further, one skilled in the art will appreciate that other cloning techniques including, but not limited to, PCR-based or recombination-based techniques can be used to generate suitable expression cassettes.

In addition, WO 2004/071467 and U.S. Pat. No. 7,129,089 describe the further linking together of individual promoter/gene/transcription terminator cassettes in unique combinations and orientations, along with suitable selectable marker cassettes, in order to obtain the desired phenotypic expression. Although this is done mainly using different restriction enzymes sites, one skilled in the art can appreciate that a number of techniques can be utilized to achieve the desired promoter/gene/transcription terminator combination or orientations. In so doing, any combination and orientation of shoot apical meristem-specific promoter/gene/transcription terminator cassettes can be achieved. One skilled in the art can also appreciate that these cassettes can be located on individual DNA fragments or on multiple fragments where co-expression of genes is the outcome of co-transformation of multiple DNA fragments.

The term "root architecture" refers to the arrangement of the different parts that comprise the root. The terms "root architecture", "root structure", "root system" or "root system architecture" are used interchangeably herein.

As referred to herein, alterations in "Root lodging", "root branching" and "root biomass" are examples of alterations in "root architecture".

In general, the first root of a plant that develops from the embryo is called the primary root. In most dicots, the primary root is called the taproot. This main root grows downward and gives rise to branch (lateral) roots. In monocots the primary root of the plant branches, giving rise to a fibrous root system.

The term "altered root architecture" refers to aspects of alterations of the different parts that make up the root system at different stages of its development compared to a reference or control plant. It is understood that altered root architecture encompasses alterations in one or more measurable parameters, including but not limited to, the diameter, length, number, angle or surface of one or more of the root system parts, including but not limited to, the primary root, lateral or branch root, adventitious root, and root hairs, all of which fall within the scope of this invention. These changes can lead to an overall alteration in the area or volume occupied by the root.

One of ordinary skill in the art is familiar with protocols for determining alteration in plant root architecture. For example, wt and mutant maize plants can be assayed for changes in root architecture at seedling stage, flowering time or maturity.

Alterations in root architecture can be determined by counting the nodal root numbers of the top 3 or 4 nodes of the greenhouse grown plants or the width of the root band.

"Root band" refers to the width of the mat of roots at the bottom of a pot at plant maturity. Other measures of alterations in root architecture include, but are not limited to, the number of lateral roots, average root diameter of nodal roots, average root diameter of lateral roots, number and length of root hairs.

The extent of lateral root branching (e.g. lateral root number, lateral root length) can be determined by sub-sampling a complete root system, imaging with a flat-bed scanner or a digital camera and analyzing with WinRHIZO™ software (Regent Instruments Inc.).

Root lodging is the measure of plants that do not root lodge; plants that lean from the vertical axis at an approximately 30 degree angle or greater would be counted as root lodged.

One can also evaluate alterations in root lodging, root biomass and root branching by the ability of the plant to increase yield in field testing when compared, under the same conditions, to a control or reference plant.

Data taken on root phenotype are subjected to statistical analysis, normally a t-test to compare the transgenic roots with that of non-transgenic sibling plants. One-way ANOVA may also be used in cases where multiple events and/or constructs are involved in the analysis.

One can also evaluate alterations in root lodging, root biomass and root branching by the ability of the plant to maintain substantial yield (for example, at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under stress conditions (e.g., nutrient over-abundance or limitation, water over-abundance or limitation, presence of disease), when compared to the yield of a control or reference plant under non-stressed conditions. The wild-type FEA3 or "fasciated ear3" gene encodes a predicted leucine rich repeat receptor-like protein (LRR-RLP) consisting of 506 amino acids. The terms "wild-type FEA3 gene", "FEA3 wt gene", "Fea3 gene" and "FEA3 gene" are used interchangeably herein. *Arabidopsis* contains three FEA3 orthologues At3g25670, At1g13230, and At1g68780.

LRR-RLPs constitute a large class of LRR-containing proteins (Wang, G. et al (2010) *Critical Reviews in Plant Science*, 29: 285-299). Structurally, LRR-RLPs can be divided into the following seven distinct domains: a signal peptide, a cysteine-rich domain, the extracellular LRR (eLRR) domain, a variable domain, an acidic domain, a transmembrane domain, and a short cytoplasmic region (Jones and Jones (1997) *Adv. Bot. Res.* 24:89-167). The LRR-containing C domain is composed of three subdomains with a non-LRR island subdomain (C2) that interrupts eLRR subdomains C1 and C3, although not all RLPs contain a C2 island (Wang, G. et al. (2008) *Plant Physiol* 147: 503-517).

Our analysis of fea2/fea3 double mutants indicate that fea2 and fea3 act in independent pathways.

Our analysis of td1/fea3 double mutants indicate that td1 and fea3 act in independent pathways.

The term fasciation, from the Latin fascis, meaning bundle, describes variations in plant form resulting from proliferative growth.

Plants with fea3 mutations, wherein the mutation results in a loss of FEA3 function or loss of FEA3 expression are also called "fea3 plants" or "fea3 null plants". "fea3 null plants" exhibit the "fea3 phenotype" or the "fea3 null phenotype". fea3 plants develop larger meristems during inflorescence and floral shoot development, and ear inflorescence meristems show severe fasciation, suggesting that fea3 normally acts to limit the growth of these meristems.

Plants with weak fea3 mutations, wherein the mutation results in a partial loss of fea3 function or partial loss of fea3 expression are also called "fea3 plants with weak fea3 phenotype". "weak fea3 plants" exhibit the "weak fea3 phenotype". fea3 plants with weak fea3 alleles exhibit similar phenotype as the fea3 null plants, but to a lesser extent. fea3 plants with weak fea3 alleles may also exhibit partial fea3 null phenotype, that is may not exhibit all the fea3 null characteristics. "Weak fea3 alleles" as referred to herein are fea3 variants or variants of SEQ ID NOS: 1, 2 or 4, which confer weak fea3 phenotype on the plant.

Plants with fea3 mutations that exhibit "null fea3 phenotype" or "weak fea3 phenotype" are referred to herein as plants with "mutant fea3 phenotype".

The term "dominant negative mutation" as used herein refers to a mutation that has an altered gene product that acts antagonistically to the wild-type allele. These mutations usually result in an altered molecular function (often inactive) and are characterized by a "dominant negative" phenotype. A gene variant, a mutated gene or an allele that confers "dominant negative phenotype" would confer a "null" or a "mutated" phenotype on the host cell even in the presence of a wild-type allele.

As used herein, a polypeptide (or polynucleotide) with "FEA3 activity" refers to a polypeptide (or polynucleotide), that when expressed in a "fea3 mutant line" that exhibits the "fea3 mutant phenotype", is capable of partially or fully rescuing the fea3 mutant phenotype.

The terms "gene shuffling" and "directed evolution" are used interchangeably herein. The method of "gene shuffling" consists of iterations of DNA shuffling followed by appropriate screening and/or selection to generate variants of FEA3 nucleic acids or portions thereof having a modified biological activity (Castle et al., (2004) Science 304(5674): 1151-4; U.S. Pat. Nos. 5,811,238 and 6,395,547).

"TILLING" or "Targeting Induced Local Lesions IN Genomics" refers to a mutagenesis technology useful to generate and/or identify, and to eventually isolate mutagenised variants of a particular nucleic acid with modulated expression and/or activity (McCallum et al., (2000), *Plant Physiology* 123:439-442; McCallum et al., (2000) *Nature Biotechnology* 18:455-457; and, Colbert et al., (2001) *Plant Physiology* 126:480-484).

TILLING combines high density point mutations with rapid sensitive detection of the mutations. Typically, ethylmethanesulfonate (EMS) is used to mutagenize plant seed. EMS alkylates guanine, which typically leads to mispairing. For example, seeds are soaked in an about 10-20 mM solution of EMS for about 10 to 20 hours; the seeds are washed and then sown. The plants of this generation are known as M1. M1 plants are then self-fertilized. Mutations that are present in cells that form the reproductive tissues are inherited by the next generation (M2). Typically, M2 plants are screened for mutation in the desired gene and/or for specific phenotypes.

TILLING also allows selection of plants carrying mutant variants. These mutant variants may exhibit modified expression, either in strength or in location or in timing (if the mutations affect the promoter for example). These mutant variants may even exhibit lower FEA3 activity than that exhibited by the gene in its natural form. TILLING combines high-density mutagenesis with high-throughput screening methods. The steps typically followed in TILLING are: (a) EMS mutagenesis (Redei G P and Koncz C (1992) In Methods in *Arabidopsis* Research, Koncz C, Chua N H, Schell J, eds. Singapore, World Scientific Publishing Co, pp. 16-82; Feldmann et al., (1994) In Meyerowitz E M, Somerville C R, eds, *Arabidopsis*. Cold Spring Harbor Laboratory Press, Cold Spring Harbor, N.Y., pp 137-172; Lightner J and Caspar T (1998) In J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (U.S. Pat. No. 8,071,840).

Other mutagenic methods can also be employed to introduce mutations in the FEA3 gene. Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, and N-nitroso-N-ethylurea. Alternatively, ionizing radiation from sources such as X-rays or gamma rays can be used.

Other detection methods for detecting mutations in the FEA3 gene can be employed, e.g., capillary electrophoresis (e.g., constant denaturant capillary electrophoresis and single-stranded conformational polymorphism). In another example, heteroduplexes can be detected by using mismatch repair enzymology (e.g., CELI endonuclease from celery). CELI recognizes a mismatch and cleaves exactly at the 3' side of the mismatch. The precise base position of the mismatch can be determined by cutting with the mismatch repair enzyme followed by, e.g., denaturing gel electrophoresis. See, e.g., Oleykowski et al., (1998) "Mutation detection using a novel plant endonuclease" *Nucleic Acid Res.* 26:4597-4602; and, Colbert et al., (2001) "High-Throughput Screening for Induced Point Mutations" *Plant Physiology* 126:480-484.

The plant containing the mutated fea3 gene can be crossed with other plants to introduce the mutation into another plant. This can be done using standard breeding techniques.

Homologous recombination allows introduction in a genome of a selected nucleic acid at a defined selected position. Homologous recombination has been demonstrated in plants. See, e.g., Puchta et al. (1994), *Experientia* 50: 277-284; Swoboda et al. (1994), *EMBO J.* 13: 484-489; Offringa et al. (1993), *Proc. Natl. Acad. Sci. USA* 90: 7346-7350; Kempin et al. (1997) *Nature* 389:802-803; and, Terada et al., (2002) *Nature Biotechnology,* 20(10):1030-1034).

Methods for performing homologous recombination in plants have been described not only for model plants (Offringa et al. (1990) *EMBO J.* October; 9(10):3077-84) but also for crop plants, for example rice (Terada R, Urawa H, Inagaki Y, Tsugane K, Iida S. *Nat Biotechnol.* 2002; Iida and Terada: *Curr Opin Biotechnol.* 2004 April; 15(2):1328). The nucleic acid to be targeted (which may be FEA3 nucleic acid or a variant thereof as hereinbefore defined) need not be targeted to the locus of FEA3 gene respectively, but may be introduced in, for example, regions of high expression. The nucleic acid to be targeted may be weak fea3 allele or a dominant negative allele used to replace the endogenous gene or may be introduced in addition to the endogenous gene.

Transposable elements can be categorized into two broad classes based on their mode of transposition. These are designated Class I and Class II; both have applications as mutagens and as delivery vectors. Class I transposable elements transpose by an RNA intermediate and use reverse transcriptases, i.e., they are retroelements. There are at least three types of Class I transposable elements, e.g., retrotransposons, retroposons, SINE-like elements. Retrotransposons typically contain LTRs, and genes encoding viral coat proteins (gag) and reverse transcriptase, RnaseH, integrase and polymerase (pol) genes. Numerous retrotransposons have been described in plant species. Such retrotransposons mobilize and translocate via a RNA intermediate in a reaction catalyzed by reverse transcriptase and RNase H encoded by the transposon. Examples fall into the Ty1-copia and Ty3-gypsy groups as well as into the SINE-like and LINE-like classifications (Kumar and Bennetzen (1999) *Annual Review of Genetics* 33:479). In addition, DNA transposable elements such as Ac, TamI and En/Spm are also found in a wide variety of plant species, and can be utilized in the invention. Transposons (and IS elements) are common tools for introducing mutations in plant cells.

The shoot apical meristem (SAM) regulates its size during development by balancing stem cell proliferation and the incorporation of daughter cells into primordia. Several "fasciated" mutants with enlarged meristems have been identified in maize, and can be used to study the genetic basis of meristem size regulation. Two maize genes, thick tassel dwarf1 (td1; Bommert et al. (2005) Development 132:1235-1245) and fasciated ear2 (fea2; Taguchi-Shiobara et al. (2001) *Genes Dev.* 65 15:2755-2766), are homologous to the *Arabidopsis* leucine-rich-repeat (LRR) receptor-genes CLAVATA1 (CLV1) and CLAVATA2 (CLV2), respectively. CLV1 and CLV2 were predicted to form a receptor complex that is activated by the CLV3 ligand and represses the stem cell promoting transcription factor WUSCHEL. Analysis of fea2/td1 double mutants however suggested, that the basic CLV1-CLV2 co-receptor model is likely more complex, as the fea2/td1 double mutant showed a more severe phenotype than either single mutant. Recent analysis in *Arabidopsis* revealed that the separate action of three major receptor complexes (CLV1-BAM1 (BARELY ANY MERISTEM1), CLV2-CRN (CORYNE), and RPK2/TOAD2 (RECEPTOR-LIKE PROTEIN KINASE2/TOADTOOL2)) is necessary for proper meristem size control in *Arabidopsis*.

Here we present a phenotypic and molecular characterization of the maize mutant fea3 that causes the overproliferation of the inflorescence meristem, leading to enlarged or fasciated meristems. We cloned the fea3 gene using a map-based cloning approach and the mutant results from an insertion of a partial retrotransposon into an exon of the fea3 locus. We confirmed this identity by isolation of three additional alleles of fea3 derived from a targeted EMS mutagenesis. The FEA3 gene encodes a predicted leucine rich repeat receptor-like protein, related to fea2. In-situ hybridization and Red Fluorescent Protein-tagged transgenic plants show that FEA3 is expressed in the organizing center of SAM and is also expressed in the root apical meristem. FEA3 is localized in the plasma membrane. To determine if FEA3 responds to a CLV3-related (CLE) peptide, we tested its sensitivity to different peptides. The fea3 mutants showed reduced peptide sensitivity, but interestingly they responded to a different CLE peptide compared to FEA2. Double mutants of fea2/fea3 and td1/fea3 have additive and synergistic fasciated phenotypes in ear and tassel, indicating that they act in independent pathways that converge on the same downstream target to control meristem size. Consequently, the function of FEA3 as a receptor protein is in a new pathway distinct from that of TD1 and FEA2.

EMBODIMENTS

In one embodiment, the fea3 variant that can be used in the methods of the current invention is one or more of the following fea3 nucleic acid variants: (i) a portion of a fea3 nucleic acid sequence (SEQ ID NO:1, 2 or 4); (ii) a nucleic acid sequence capable of hybridizing with a fea3 nucleic acid sequence (SEQ ID NO:1, 2 or 4); (iii) a splice variant of a fea3 nucleic acid sequence (SEQ ID NO:1, 2 or 4); (iv) a naturally occurring allelic variant of a fea3 nucleic acid sequence (SEQ ID NO:1, 2 or 4); (v) a fea3 nucleic acid sequence obtained by gene shuffling; (vi) a fea3 nucleic acid sequence obtained by site-directed mutagenesis; (vii) a fea3 variant obtained and identified by the method of TILLING.

In one embodiment, the levels of endogenous FEA3 expression can be decreased in a plant cell by antisense constructs, sense constructs, RNA silencing constructs, RNA interference, artificial microRNAs and genomic disruptions. Examples of genomic disruption include, but are not limited to, disruptions induced by transposons, tilling, homologous recombination.

In one embodiment, a modified plant miRNA precursor may be used, wherein the precursor has been modified to replace the miRNA encoding region with a sequence designed to produce a miRNA directed to FEA3. The precursor is also modified in the star strand sequence to correspond to changes in the miRNA encoding region.

In one embodiment, a nucleic acid variant of FEA3 useful in the methods of the invention is a nucleic acid variant obtained by gene shuffling.

In one embodiment, a genetic modification may also be introduced in the locus of a maize FEA3 gene using the technique of TILLING (Targeted Induced Local Lesions In Genomes).

In one embodiment, site-directed mutagenesis may be used to generate variants of fea3 nucleic acids. Several methods are available to achieve site-directed mutagenesis; the most common being PCR based methods (U.S. Pat. No. 7,956,240).

In one embodiment homologous recombination can also be used to inactivate, or reduce the expression of endogenous FEA3 gene in a plant.

Homologous recombination can be used to induce targeted gene modifications by specifically targeting the FEA3 gene in vivo. Mutations in selected portions of the FEA3 gene sequence (including 5' upstream, 3' downstream, and intragenic regions) such as those provided herein are made in vitro and introduced into the desired plant using standard techniques. Homologous recombination between the introduced mutated fea3 gene and the target endogenous FEA3 gene would lead to targeted replacement of the wild-type gene in transgenic plants, resulting in suppression of FEA3 expression or activity.

In one embodiment, catalytic RNA molecules or ribozymes can also be used to inhibit expression of FEA3 gene. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules. The inclusion of ribozyme sequences within antisense RNAs confers RNA-cleaving activity upon them, thereby increasing the activity of the constructs. A number of classes of ribozymes have been identified. For example, one class of ribozymes is derived from a number of small circular RNAs that are capable of self-cleavage and replication in plants. The RNAs can replicate either alone (viroid RNAs) or with a helper virus (satellite RNAs). Examples of RNAs include RNAs from avocado sunblotch viroid and the satellite RNAs from tobacco ringspot virus, lucerne transient streak virus, velvet tobacco mottle virus, Solanum nodiflorum mottle virus and subterranean clover mottle virus. The design and use of target RNA-specific ribozymes has been described. See, e.g., Haseloff et al. (1988) Nature, 334:585-591.

Another method to inactivate the FEA3 gene is by inhibiting expression is by sense suppression. Introduction of expression cassettes in which a nucleic acid is configured in the sense orientation with respect to the promoter has been shown to be an effective means by which to block the transcription of a desired target gene. (Napoli et al. (1990), The Plant Cell 2:279-289, and U.S. Pat. Nos. 5,034,323, 5,231,020, and 5,283,184).

In one embodiment, the FEA3 gene can also be inactivated by, e.g., transposon based gene inactivation.

In one embodiment, the inactivating step comprises producing one or more mutations in the FEA3 gene sequence, where the one or more mutations in the FEA3 gene sequence comprise one or more transposon insertions, thereby inactivating the FEA3 gene compared to a corresponding control plant. For example, the mutation may comprise a homozygous disruption in the FEA3 gene or the one or more mutations comprise a heterozygous disruption in the FEA3 gene.

These mobile genetic elements are delivered to cells, e.g., through a sexual cross, transposition is selected for and the resulting insertion mutants are screened, e.g., for a phenotype of interest. Plants comprising disrupted fea3 genes can be crossed with a wt plant. Any of a number of standard breeding techniques can be used, depending upon the species to be crossed. The location of a TN (transposon) within a genome of an isolated or recombinant plant can be determined by known methods, e.g., sequencing of flanking regions as described herein. For example, a PCR reaction from the plant can be used to amplify the sequence, which can then be diagnostically sequenced to confirm its origin. Optionally, the insertion mutants are screened for a desired phenotype, such as the inhibition of expression or activity of fea3 or alteration of an agronomic characteristic.

EXAMPLES

The present invention is further illustrated in the following Examples, in which parts and percentages are by weight and degrees are Celsius, unless otherwise stated. It should be understood that these examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Furthermore, various modifications of the invention in addition to those shown and described herein will be apparent to those skilled in the art from the foregoing description. Such modifications are also intended to fall within the scope of the appended claims.

Example 1

Cloning of Maize Fea3 Gene

Figure 1:
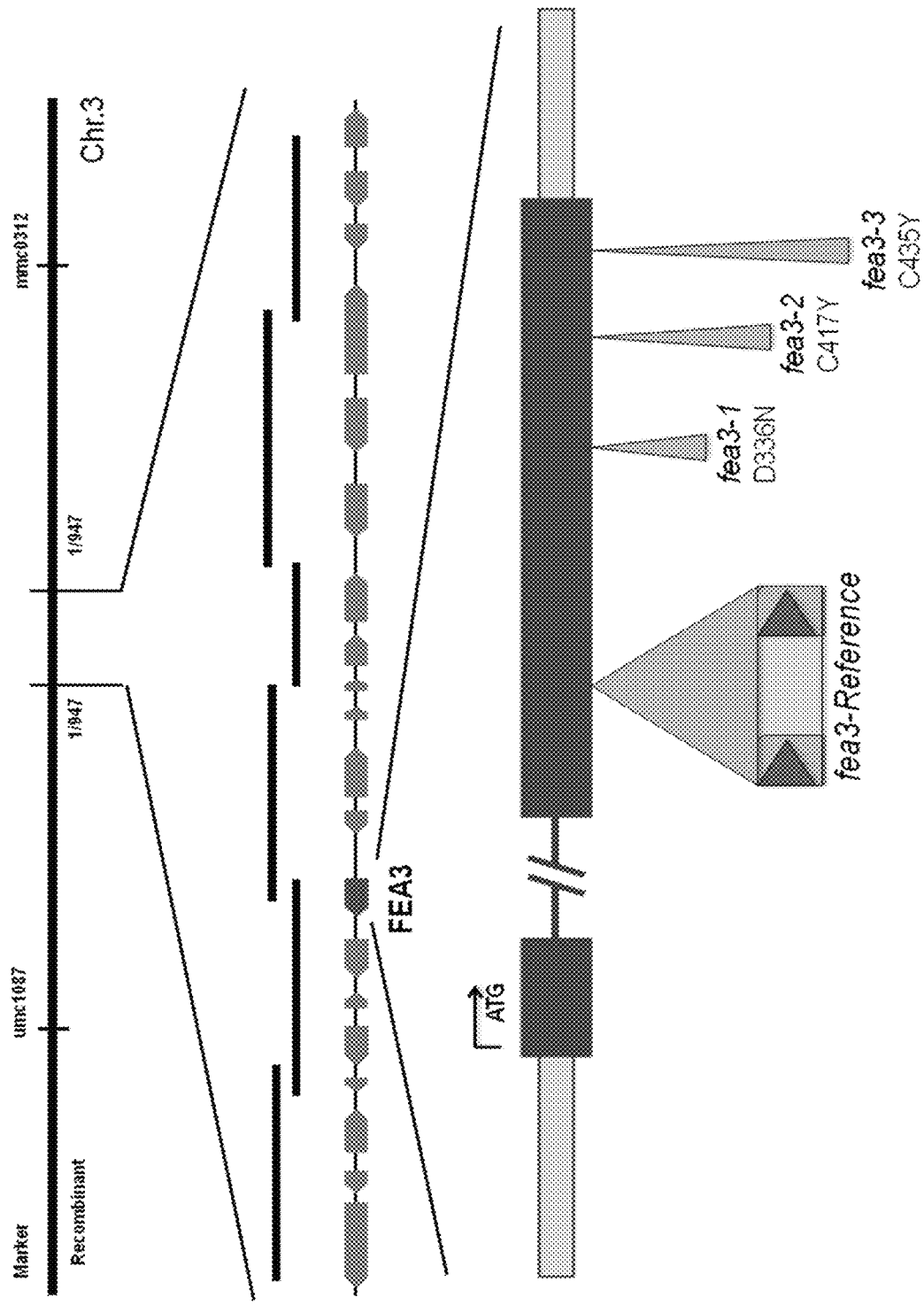

A map-based cloning approach was used to isolate the fea3-0 Reference allele (SEQ ID NO:20), which was originally mapped on chromosome 3 (FIG. 1). A partial retrotransposon insertion within a gene encoding a leucine-rich-repeat receptor like protein was identified by fine mapping. To confirm that this insertion was the causative mutation, a targeted EMS screen was performed, which allowed us to identify three additional alleles of fea3, designated fea3-1, -2 and -3 (SEQ ID NOS: 22, 24, and 26 respectively).

fea3 was initially mapped using bulked segregant mapping. A mapping population of 947 individuals was used to place the locus between the BACs c0267MO3 and c0566I18, a region of ~6 BACs containing ~25 predicted genes. Sequencing and expression analysis revealed one candidate, an LRR receptor like protein that had a small insertion in the fea3-0 allele. Three additional alleles were identified using a targeted EMS screen from ~10,000 M1 plants. Sequencing of each allele revealed an amino acid change relative to the progenitor, confirming that the correct gene was isolated.

Example 2

Expression Analysis of FEA2 and FEA3 Genes

Figure 2A:
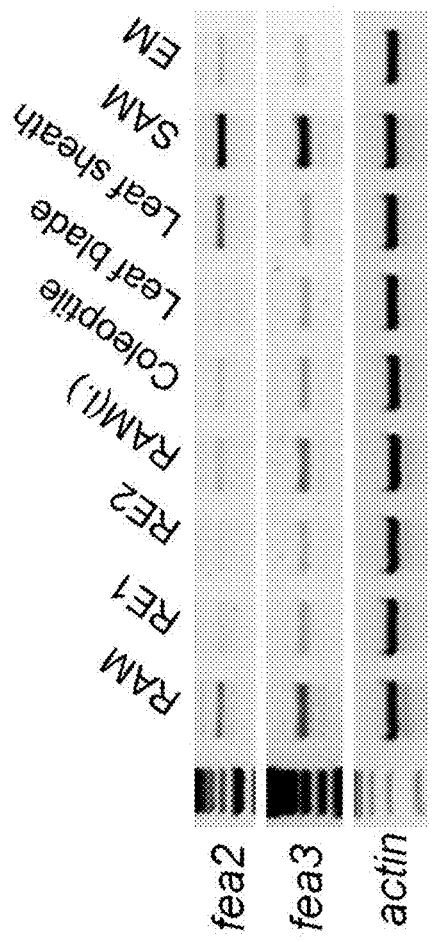
Figure 2B:
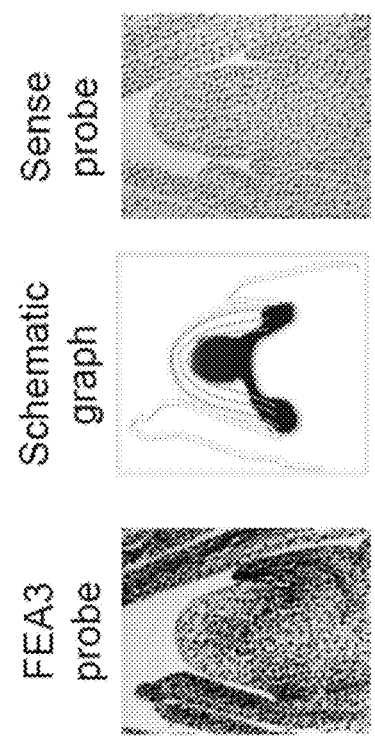

RT-PCR was done for FEA2 and FEA3 in different tissues. FIG. 2A shows the expression of FEA22 and FEA3 in different tissues. FEA2 and FEA3 show the strongest expression the shoot apical meristem. FIG. 2B shows the FEA3 expression in situ, showing expression is detected organizing center of meristem. This region overlaps with WUS expression region. This pattern is quite different with other known fasciated ear mutant (Inflorescence transition stage).

Example 3

Maize Mutant Fea3 Phenotype

During vegetative development fea3 mutant plants appear normal. After transition to flowering, however, during early inflorescence development, fea3 mutants ears (FIG. 3B) show a flattened and enlarged inflorescence meristem (IM) compared to wild type (FIG. 3A). At later stages of development enlargement of the IM causes fasciation in the mutant (FIG. 3C). At maturity wild type ears show regularly spaced and organized kernel rows (FIG. 3D), whereas fea3 mutant ears show a progressive enlargement of the ear tip, extra kernel rows and an overall irregular arrangement of rows (FIG. 3E).

Example 4

Fea3/Fea2 Double Mutant Analysis

The tassels of maize fea3/fea2 double mutants are thicker and shorter compared to single mutants (FIG. 4A). Spikelet density was analyzed by counting spikelets per cm along the main rachis. Double mutants show a significant increase in spikelet density, indicating additive effects between fea2 and fea3 (FIG. 4B). Similarly, double mutant ear phenotypes show additive fasciation (FIG. 4C). These results suggest that FEA2 and FEA3 act in different pathways.

Example 5

Clavata3 Peptide Root Assay

In *Arabidopsis*, CLAVATA2 activity can be detected by responses of root growth to CLAVATA3 (CLV3) peptide. To analyze whether FEA3 and FEA2 respond to CLV3, and determine if they act in a common pathway a CLV3 peptide assay was performed. B73 and homozygous fea2 and fea3 mutant seedlings were germinated and grown on agar plates containing CLV3 peptide. As a control, seedlings were also grown on plates containing a mutated version of the peptide and on plates without any peptide. After 7 days the length of the primary root was measured. B73 wild type plants show strong root growth inhibition as result of response to CLV3 peptide, but fea2 mutants do not respond to CLV3 peptide. Interestingly, fea3 mutants respond to CLV3 peptide, even though FEA3 is expressed in root (FIG. 5).

Example 6

Expression of Red Fluorescent Protein from the FEA3 Promoter

A recombinant DNA construct was made to allow for in vivo localization of FEA3 that has been tagged with Red Fluorescent Protein (RFP). The construct contained the following elements in the 5' to 3' orientation: 1) FEA3 Promoter; 2) FEA3 signal peptide coding region; 3) RFP-FEA3 fusion protein coding region; and 4) FEA3 3'-UTR. Transgenic maize plants containing this recombinant DNA construct were produced. Analysis of the transgenic plants revealed that RFP-FEA3 fusion protein was expressed in the inflorescence meristem central zone of both the ear and the tassel.

Figure 2C:
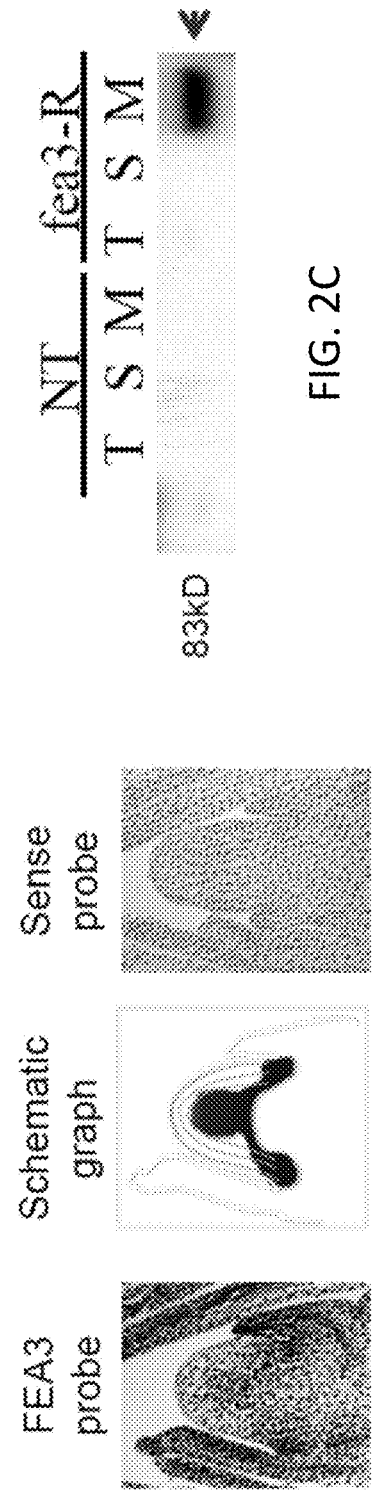

To see whether FEA3 is localized in the membrane or the soluble fraction, western blot was performed after membrane fractionation. Tissue used was young tassel (about 0.5-3 cm tassel) from the transgenic plant expressing RFP tagged FEA3 protein, as described above. FIG. 2C shows that RFP tagged FEA3 is localized in the plasma membrane, with the arrow indicating band size of about 83 kD which is expected fusion size of RFP tagged FEA3.

Example 7

Clavata3-Like Peptide Root Assay

To analyze whether FEA3 responds to CLV3-like peptides, and determine if they act in a common pathway, a CLV3 peptide assay was performed. The peptides used were ZCL3 (*Zea mays* CLE-like 3; SEQ ID NO:32), FCP1 (SEQ ID NO:33), CLV3 (SEQ ID NO:34), CLE20 (SEQ ID NO:35), CLE40 (SEQ ID NO:36), ZCL21 (*Zea mays* CLE-like 3; SEQ ID NO:37), and ZCL23 (*Zea mays* CLE-like 23; SEQ ID NO:38).

The ZCL peptides were found in maize sequences in the NCBI database by homology search using the CLV3, CLE, and rice related peptides (Fiers et al Plant Cell (2005), 17: 2542-2553; Suzaki et al (2008), Plant Cell, 20: 2049-2058).

B73 and fea3 mutant seedlings were germinated and grown on agar plates containing each 5 μM or 10 μM peptide. As a control, seedlings were also grown on plates containing a scramble of the peptide. After 7 days the length of the primary root was measured. B73 wild type plants show strong root growth inhibition as result of response to ZCL3 (SEQ ID NO:32), FCP1 (SEQ ID NO:33) and CLV3 (SEQ ID NO:34) peptides. Interestingly, fea3 mutants show less sensitivity to FCP1 peptide (FIG. 6).

Example 8

Embryo Culture Assay in Presence of FCP1 Peptide

Wt and fea3 embryos were cultured in the presence of 20 μM FCP1 peptide (SEQ ID NO:33) or 20 μM scrambled peptide. For measurement of embryo SAM growth, about 10 days after pollination, embryos were sterilized (whole corn was sterilized, not individual young seeds) and dissected embryos and put the embryos down on the media and the measurement of SAM size was done two weeks after planting (embryo culture). WT embryo SAM growth was found to be strongly inhibited by FCP1, but fea3 embryos showed resistance (FIG. 7A shows an image comparing wt and fea3 embryo SAM growth, and FIG. 7B shows a quantitative analysis of the same). For the histogram shown in FIG. 7B, p<0.0001

Example 9

Fea3/td1 Double Mutant Analysis

The tassels of maize fea3/td1 double mutants are thicker and shorter compared to single mutants (FIG. 4A). Spikelet density was analyzed by counting spikelets per cm along the main rachis. Double mutants show a significant increase in spikelet density, indicating additive effects between fea2 and fea3 (FIG. 4B). Similarly, double mutant ear phenotypes show additive fasciation (FIG. 4C). These results suggest that FEA2 and FEA3 act in different pathways.

Example 10

Analysis of Fea3 Orthologs in Other Plant Species

*Arabidopsis*, rice, sorghum and soy orthologs of FEA3 can also be analyzed by doing experiments described in Examples 1-9 for maize FEA3.

What is claimed is:

1. A modified maize plant comprising an introduced genetic modification in an endogenous fea3 gene encoding a FEA3 polypeptide, wherein the FEA3 polypeptide comprises an amino acid sequence that is at least 95% identical to SEQ ID NO: 3, wherein the modified maize plant comprises an amino acid substitution in the FEA3 polypeptide and exhibits increased kernel row number or kernel number, compared to a control maize plant not comprising the genetic modification.

2. The maize plant of claim 1, wherein the maize plant exhibits increased kernel row number.

3. The maize plant of claim 1, wherein the maize plant exhibits increased ear size.

4. The maize plant of claim 1, wherein the maize plant exhibits reduced tassels.

* * * * *

```
SEQUENCE LISTING

<160> NUMBER OF SEQ ID NOS: 38

<210> SEQ ID NO 1
<211> LENGTH: 3338
<212> TYPE: DNA
<213> ORGANISM: Zea mays

<400> SEQUENCE: 1
acaacgccag accgcctgcc tgtgcttgca gccaggccgg ccagctgcct gcctgcctgt        60
tgtcgtctgc ggcgcgacgg cggccgcccg gtcgaccgcc cgcattggga tcccagagc        120 agcgcttggc ataggggaat gtcccgggtc agccaccgtc gcctctgcgc tgcgaaagcc       180
ccgcatttac ttgccaccta gaaggggca ccctcgcga gaccagcgc cagacagagc        240 cagcaatggc tgctgctgct gctcctcctc ctcctatata gcggggcccg tgccgagcgc       300
tcgatccagt tcttctgatc tctgacttct gagcgaggag tggacgagtg gtgtgccgtc       360
gtccggttcc cgttggtttg gcgatgaggc gcgctcgcgg tcgccgcggg ctgctgcttc       420
tcctcggcgt ggcgctctcg gcggctgcgc tgctccgtgg ctgcgcgggg cagcaagggg       480
aggacggctc ggacgcccct gcggcggcgg cggcggagac ggcccccatg gaggagaagg       540
agcgcagggc gctgtacgcc gccatcgaga gcttcgtcgg caagggggtgg aacggctccg       600 ggctctaccc agaccctgc ggctggtctc ccatccaggc gcgtccctgc ccttcctgcg        660 cttcccttt cgcatcgatc tatgttaccg tgctgttcga ttttctggcc cgcgtatgtt       720
cgttcatcat gttcgttctt cagacgcgcg aagctttcct ctttggtttt ttcggctttg       780
cccgtcctcg tcacacgccc tttctcggtg ctccctgct gcctgctttg agctccaatc       840
caaaaaccgt ttgcgagcga aaggaggagc aagtcggtag cctccgaaat gaaattggtg       900
ccctgtttgg ggatgcagga cgcacgccaa gtcgccacca aatctcctgc tgtaatttcc       960
cgtgttaaaa ccttcctcgt ctcgcttcca gaatttctgg ccttccggta gcctctgctg      1020
tttttgtctt gtgttcgtcc ttcgtcgcac tcgtgccctg ctcctcaact gttgcttcga      1080
gattgtggca ctgttttgct gtgcgccgct gcacattcag ttcactgttg gacgagacct      1140
ctgcttgatc cccttgtgtc ttcgcatctc agccttttgc tcgatatggt aggaggatct      1200
gatctcttgg gcaggaactt tccactcaca tgaaaagaac ctcccatgat ttgaaatggc      1260
atgctccgcc caagatttt ctcatacagt actactactc tctagtatag attttagtag       1320
taccttgaca tcttcttcct tttgctcgcg cccgagaagg aatcagtcct actactccat       1380
aggagttttt gctctaacaa ttactggaat ttaccgcata tttatcttcc ttcacacggt       1440
acactggaat tcattctgg ttgttacagt accagtaaag ttaagaaggg gccaaatttg       1500
tactaggtgc acctttaaga aatgtcgcca tcttggatca tcctcatcca tgtctgttat      1560
```

```
tactgctagt agttactgtt gagcttgtgt ttactttccg agtaggacac tctcagattg    1620
cagcgtgctt gcctgcctgt taaaattaag gggattcaat ttcagtggat tgagcagatg    1680
tggttcttgg atgccaaaaa cctgtgcagg gggtgtcatg tgatctcttc aatggcctgt    1740
ggtacccaac agtgatgagc attggcccag tccttgacaa ctcgctgcag tgcggccccg    1800
acgccaagtt cagcgcccag ctgttcgacc tgaggcgcct ccggacgctg tctttctaca    1860
gctgcttccc ggcgagcaac cccacggcca tcccgaccgg cagctgggag aagctggcgg    1920
ggacgctgga gacgctggag ttccgcacca acccgggcct gaacggcgcc atcccggcgt    1980
ccctcggccg cctggccagc ctgcagtcgc tggtgctcgt ggagaacaac ctgacggggc    2040
ccgtgcccgc ggagctgggc gcgctgtcga ggctgagacg gctggtgctg tccgggaacg    2100
ggctgtcggg gccgatcccg gtgacactcg gtaacgaccg ccgcgccgac gagctgctgc    2160
tgatcgtgga cctgagcagg aactatctaa ccggctctct gccttcgtcg ctaggtggcc    2220
tcacggggct cctgaagatg gacctgagca gcaacctgct gcaggcagc atcccgccgg    2280 agctcgcggg gctcaggagc ctcacgctgc tggacctcag gaacaacagc ctcaccggcg    2340
ggctgcccca gttcgtgcag ggcatggcgt cgctgcagga cctgctgctc tcgaacaacc    2400
cgctgggcgg cggcctgccg cagtccggct gggggcgct gcggcctg gccacgctgg    2460 acctgtccaa cgtcggcctc gtgggcgcca taccggggtc catggcggcc ctgacggggc    2520
tccggttcct ggcgctggac cacaaccgcc tgacgggggc cgtgccgccc gagctcgccc    2580
ggctgcccag catcggcgcg ctgtacctga acggcaacaa cctgacgggg acgctggagt    2640
tctcggccgg gttctaccag cgcatggggc ggcggttcgc gtcgtgggac aaccccgggc    2700
tgtgctacaa cgtcgcggcc gtggacgcgg cccacgcgcc gtcgggcgtg gtggtgtgca    2760
aggacctgca ggagcccagc gtgggcggcg gcgcgcggga cggggacggg gacggggacg    2820
cggaggagga cgggacgaag cccgaggcgg gctccagcct cgtggcctcc tcgtcgtccg    2880
gcatgccggt tggcagtgtc ggtgggctcc ggtacctggt ggtggttcgg ggaatggcgg    2940
ctgcggttct tgggttggtg tccctcctac aatagcaagc aagcaggttc agaagaagaa    3000
cacggagaaa cttgaagtaa tgctaggtag gttagcacga agtagtttct gcgcgttctc    3060
tgtgatcttt tggcatttgt ttttggctgc tggtggctta ccatcgtcag atggtgacgg    3120
aggaaggagg gaacatggat ctggatggtg tgagccacag attacattac agtagtagag    3180
taaactatga gagttcttgt ggactgaagg tgtgtagtgg tggatagggt agcttctccg    3240
gggttctttt tgtgtgtaatt agcctgtgtc gccctgtggt gtcatgttac aacagcaagt    3300
ggaaatctaa gctggttcgt ccgttgttgg agaatcag                            3338
```

<210> SEQ ID NO 2
<211> LENGTH: 1521
<212> TYPE: DNA
<213> ORGANISM: Zea mays

<400> SEQUENCE: 2

```
atgaggcgcg ctcgcggtcg ccgcgggctg ctgcttctcc tcggcgtggc gctctcggcg      60
gctgcgctgc tccgtggctg cgcggggcag caagggagg acggctcgga cgcccctgcg     120
gcggcggcgg cggagacggc ccccatggag agaaggagc gcagggcgct gtacgccgcc     180
atcgagagct tcgtcggcaa ggggtggaac ggctccgggc tctacccaga cccctgcggc     240
tggtctccca tccagggggt gtcatgtgat ctcttcaatg gcctgtggta cccaacagtg     300
atgagcattg gcccagtcct tgacaactcg ctgcagtgcg ccccgacgc caagttcagc     360
```

```
gcccagctgt tcgacctgag gcgcctccgg acgctgtctt tctacagctg cttcccggcg    420 agcaaccccca cggccatccc gaccggcagc tgggagaagc tggcggggac gctggagacg    480
ctggagttcc gcaccaaccc gggcctgaac ggcgccatcc cggcgtccct cggccgcctg    540
gccagcctgc agtcgctggt gctcgtggag aacaacctga cggggcccgt gcccgcggag    600
ctgggcgcgc tgtcgaggct gagacggctg gtgctgtccg ggaacgggct gtcggggccg    660
atcccggtga cactcggtaa cgaccgccgc gccgacgagc tgctgctgat cgtggacctg    720
agcaggaact atctaaccgg ctctctgcct tcgtcgctag gtggcctcac ggggctcctg    780
aagatggacc tgagcagcaa cctgctgcag ggcagcatcc cgccggagct cgcggggctc    840
aggagcctca cgctgctgga cctcaggaac aacagcctca ccggcgggct gccccagttc    900
gtgcagggca tggcgtcgct gcaggacctg ctgctctcga caacccgct gggcggcggc    960 ctgccgcagt ccggctgggg ggcgctggcg ggcctggcca cgctggacct gtccaacgtc   1020
ggcctcgtgg gcgccatacc ggggtccatg gcggccctga cggggctccg gttcctggcg   1080
ctggaccaca accgcctgac ggggggccgtg ccgcccgagc tcgcccggct gcccagcatc   1140
ggcgcgctgt acctgaacgg caacaacctg acggggacgc tggagttctc ggccgggttc   1200
taccagcgca tggggcggcg gttcgcgtcg tgggacaacc ccgggctgtg ctacaacgtc   1260
gcggccgtgg acgcggccca cgcgccgtcg ggcgtggtgg tgtgcaagga cctgcaggag   1320
cccagcgtgg gcggcggcgc gcgggacggg gacggggacg gggacgcgga ggaggacggg   1380
acgaagcccg aggcgggctc cagcctcgtg gcctcctcgt cgtccggcat gccggttggc   1440
agtgtcggtg ggctccggta cctggtggtg gttcggggaa tggcggctgc ggttcttggg   1500
ttggtgtccc tcctacaata g                                             1521
```

<210> SEQ ID NO 3
<211> LENGTH: 506
<212> TYPE: PRT
<213> ORGANISM: Zea mays

<400> SEQUENCE: 3

```
Met Arg Arg Ala Arg Gly Arg Gly Leu Leu Leu Leu Gly Val
1               5                   10                  15

Ala Leu Ser Ala Ala Ala Leu Leu Arg Gly Cys Ala Gly Gln Gln Gly
            20                  25                  30

Glu Asp Gly Ser Asp Ala Pro Ala Ala Ala Ala Glu Thr Ala Pro
            35                  40                  45

Met Glu Glu Lys Glu Arg Arg Ala Leu Tyr Ala Ala Ile Glu Ser Phe
        50                  55                  60

Val Gly Lys Gly Trp Asn Gly Ser Gly Leu Tyr Pro Asp Pro Cys Gly
65                  70                  75                  80

Trp Ser Pro Ile Gln Gly Val Ser Cys Asp Leu Phe Asn Gly Leu Trp
                85                  90                  95

Tyr Pro Thr Val Met Ser Ile Gly Pro Val Leu Asp Asn Ser Leu Gln
            100                 105                 110

Cys Gly Pro Asp Ala Lys Phe Ser Ala Gln Leu Phe Asp Leu Arg Arg
        115                 120                 125

Leu Arg Thr Leu Ser Phe Tyr Ser Cys Phe Pro Ala Ser Asn Pro Thr
    130                 135                 140

Ala Ile Pro Thr Gly Ser Trp Glu Lys Leu Ala Gly Thr Leu Glu Thr
145                 150                 155                 160
```

```
Leu Glu Phe Arg Thr Asn Pro Gly Leu Asn Gly Ala Ile Pro Ala Ser
            165                 170                 175

Leu Gly Arg Leu Ala Ser Leu Gln Ser Leu Val Leu Val Glu Asn Asn
        180                 185                 190

Leu Thr Gly Pro Val Pro Ala Glu Leu Gly Ala Leu Ser Arg Leu Arg
        195                 200                 205

Arg Leu Val Leu Ser Gly Asn Gly Leu Ser Gly Pro Ile Pro Val Thr
    210                 215                 220

Leu Gly Asn Asp Arg Arg Ala Asp Glu Leu Leu Ile Val Asp Leu
225                 230                 235                 240

Ser Arg Asn Tyr Leu Thr Gly Ser Leu Pro Ser Leu Gly Gly Leu
                245                 250                 255

Thr Gly Leu Leu Lys Met Asp Leu Ser Ser Asn Leu Leu Gln Gly Ser
        260                 265                 270

Ile Pro Pro Glu Leu Ala Gly Leu Arg Ser Leu Thr Leu Leu Asp Leu
    275                 280                 285

Arg Asn Asn Ser Leu Thr Gly Gly Leu Pro Gln Phe Val Gln Gly Met
    290                 295                 300

Ala Ser Leu Gln Asp Leu Leu Leu Ser Asn Asn Pro Leu Gly Gly Gly
305                 310                 315                 320

Leu Pro Gln Ser Gly Trp Gly Ala Leu Ala Gly Leu Ala Thr Leu Asp
            325                 330                 335

Leu Ser Asn Val Gly Leu Val Gly Ala Ile Pro Gly Ser Met Ala Ala
            340                 345                 350

Leu Thr Gly Leu Arg Phe Leu Ala Leu Asp His Asn Arg Leu Thr Gly
        355                 360                 365

Ala Val Pro Pro Glu Leu Ala Arg Leu Pro Ser Ile Gly Ala Leu Tyr
    370                 375                 380

Leu Asn Gly Asn Asn Leu Thr Gly Thr Leu Glu Phe Ser Ala Gly Phe
385                 390                 395                 400

Tyr Gln Arg Met Gly Arg Arg Phe Ala Ser Trp Asp Asn Pro Gly Leu
            405                 410                 415

Cys Tyr Asn Val Ala Ala Val Asp Ala Ala His Ala Pro Ser Gly Val
        420                 425                 430

Val Val Cys Lys Asp Leu Gln Glu Pro Ser Val Gly Gly Gly Ala Arg
    435                 440                 445

Asp Gly Asp Gly Asp Gly Asp Ala Glu Glu Asp Gly Thr Lys Pro Glu
    450                 455                 460

Ala Gly Ser Ser Leu Val Ala Ser Ser Ser Gly Met Pro Val Gly
465                 470                 475                 480

Ser Val Gly Gly Leu Arg Tyr Leu Val Val Arg Gly Met Ala Ala
                485                 490                 495

Ala Val Leu Gly Leu Val Ser Leu Leu Gln
            500                 505

<210> SEQ ID NO 4
<211> LENGTH: 1439
<212> TYPE: DNA
<213> ORGANISM: Zea mays

<400> SEQUENCE: 4
atgaggcgcg ctcgcggtcg ccgcgggctg ctgcttctcc tcggcgtggc gctctcggcg     60
gctgcgctgc tccgtggctg cgcggggcag caagggagg acggctcgga cgcccctgcg    120
gcggcggcgg cggagacggc ccccatggag gagaaggagc gcagggcgct gtacgccgcc    180
```

```
atcgagagct tcgtcggcaa ggggtggaac ggctccgggc tctacccaga cccctgcggc    240
tggtctccca tccaggggggt gtcatgtgat ctcttcaatg cctgtggta cccaacagtg    300
atgagcattg cccagtcct tgacaactcg ctgcagtgcg ccccgacgc caagttcagc     360
gcccagctgt tcgacctgag cgcctccgg acgctgtctt tctacagctg cttcccggcg    420
agcaaccca cggccatccc gaccggcagc tgggagaagc tggcggggac gctggagacg    480
ctggagttcc gcaccaaccc gggcctgaac ggcgccatcc cggcgtccct cggccgcctg   540
gccagcctgc agtcgctggt gctcgtggag aacaacctga cggggcccgt gcccgcggag   600
ctgggcgcgc tgtcgaggct gagacggctg gtgctgtccg gaacgggct gtcggggccg    660
atcccggtga cactcggtgg tggcctcacg gggctcctga agatggacct gagcagcaac    720
ctgctgcagg gcagcatccc gccggagctc gcggggctca ggagcctcac gctgctggac    780
ctcaggaaca acagcctcac cggcgggctg ccccagttcg tgcagggcat ggcgtcgctg    840
caggacctgc tgctctcgaa caaccccgctg gcggcggcc tgccgcagtc cggctggggg   900
gcgctggcgg gcctggccac gctggacctg tccaacgtcg gcctcgtggg cgccataccg    960
gggtccatgg cggccctgac ggggctccgg ttcctggcgc tggaccacaa ccgcctgacg   1020
ggggccgtgc cgcccgagct cgcccggctg cccagcatcg gcgcgctgta cctgaacggc   1080
aacaacctga cggggacgct ggagttctcg gccgggttct accagcgcat ggggcggcgg   1140
ttcgcgtcgt gggacaaccc cggggctgtgc tacaacgtcg cggccgtgga cgcggcccac   1200
gcgccgtcgg cgtggtggt gtgcaaggac ctgcaggagc ccagcgtggg cggcggcgcg   1260
cgggacgggg acgggacgg ggacgcggag gaggacggga cgaagcccga ggcgggctcc    1320
agcctcgtgg cctcctcgtc gtccggcatg ccggttggca gtgtcggtgg gctccggtac    1380
ctggtggtgg ttcggggaat ggcggctgcg gttcttgggt tggtgtccct cctacaata     1439
```

<210> SEQ ID NO 5
<211> LENGTH: 479
<212> TYPE: PRT
<213> ORGANISM: Zea mays

<400> SEQUENCE: 5

```
Met Arg Arg Ala Arg Gly Arg Gly Leu Leu Leu Leu Gly Val
1               5                   10                  15

Ala Leu Ser Ala Ala Leu Leu Arg Gly Cys Ala Gly Gln Gln Gly
                20                  25                  30

Glu Asp Gly Ser Asp Ala Pro Ala Ala Ala Ala Glu Thr Ala Pro
            35                  40                  45

Met Glu Glu Lys Glu Arg Arg Ala Leu Tyr Ala Ala Ile Glu Ser Phe
        50                  55                  60

Val Gly Lys Gly Trp Asn Gly Ser Gly Leu Tyr Pro Asp Pro Cys Gly
65                  70                  75                  80

Trp Ser Pro Ile Gln Gly Val Ser Cys Asp Leu Phe Asn Gly Leu Trp
                85                  90                  95

Tyr Pro Thr Val Met Ser Ile Gly Pro Val Leu Asp Asn Ser Leu Gln
            100                 105                 110

Cys Gly Pro Asp Ala Lys Phe Ser Ala Gln Leu Phe Asp Leu Arg Arg
        115                 120                 125

Leu Arg Thr Leu Ser Phe Tyr Ser Cys Phe Pro Ala Ser Asn Pro Thr
    130                 135                 140

Ala Ile Pro Thr Gly Ser Trp Glu Lys Leu Ala Gly Thr Leu Glu Thr
```

```
                145                 150                 155                 160
        Leu Glu Phe Arg Thr Asn Pro Gly Leu Asn Gly Ala Ile Pro Ala Ser
                        165                 170                 175

Leu Gly Arg Leu Ala Ser Leu Gln Ser Leu Val Leu Val Glu Asn Asn
                        180                 185                 190

Leu Thr Gly Pro Val Pro Ala Glu Leu Gly Ala Leu Ser Arg Leu Arg
                        195                 200                 205

Arg Leu Val Leu Ser Gly Asn Gly Leu Ser Gly Pro Ile Pro Val Thr
                        210                 215                 220

Leu Gly Gly Gly Leu Thr Gly Leu Leu Lys Met Asp Leu Ser Ser Asn
        225                 230                 235                 240

Leu Leu Gln Gly Ser Ile Pro Pro Glu Leu Ala Gly Leu Arg Ser Leu
                        245                 250                 255

Thr Leu Leu Asp Leu Arg Asn Asn Ser Leu Thr Gly Gly Leu Pro Gln
                        260                 265                 270

Phe Val Gln Gly Met Ala Ser Leu Gln Asp Leu Leu Leu Ser Asn Asn
                        275                 280                 285

Pro Leu Gly Gly Gly Leu Pro Gln Ser Gly Trp Gly Ala Leu Ala Gly
                        290                 295                 300

Leu Ala Thr Leu Asp Leu Ser Asn Val Gly Leu Val Gly Ala Ile Pro
        305                 310                 315                 320

Gly Ser Met Ala Ala Leu Thr Gly Leu Arg Phe Leu Ala Leu Asp His
                        325                 330                 335

Asn Arg Leu Thr Gly Ala Val Pro Pro Glu Leu Ala Arg Leu Pro Ser
                        340                 345                 350

Ile Gly Ala Leu Tyr Leu Asn Gly Asn Asn Leu Thr Gly Thr Leu Glu
                        355                 360                 365

Phe Ser Ala Gly Phe Tyr Gln Arg Met Gly Arg Arg Phe Ala Ser Trp
                        370                 375                 380

Asp Asn Pro Gly Leu Cys Tyr Asn Val Ala Ala Val Asp Ala Ala His
        385                 390                 395                 400

Ala Pro Ser Gly Val Val Val Cys Lys Asp Leu Gln Glu Pro Ser Val
                        405                 410                 415

Gly Gly Gly Ala Arg Asp Gly Asp Gly Asp Gly Ala Glu Glu Asp
                        420                 425                 430

Gly Thr Lys Pro Glu Ala Gly Ser Ser Leu Val Ala Ser Ser Ser
                        435                 440                 445

Gly Met Pro Val Gly Ser Val Gly Gly Leu Arg Tyr Leu Val Val Val
        450                 455                 460

Arg Gly Met Ala Ala Ala Val Leu Gly Leu Val Ser Leu Leu Gln
        465                 470                 475

<210> SEQ ID NO 6
<211> LENGTH: 432
<212> TYPE: PRT
<213> ORGANISM: Arabidopsis thaliana

<400> SEQUENCE: 6

Met Lys Met Leu Arg Leu Arg Lys Lys Gln His Leu Val Phe Leu Leu
1               5                  10                  15

Cys Val Trp Cys Leu Val Val Asp Trp Ser Lys Ala Glu Thr Glu Glu
                20                  25                  30

Ser Asp Gly Ser Pro Met Glu Lys Thr Glu Gln Ala Ala Leu Tyr Ser
                35                  40                  45
```

```
Thr Ile Gln Gly Phe Val Gly Glu Ser Trp Asn Gly Ser Tyr Leu Tyr
     50                  55                  60

Pro Asp Pro Cys Gly Trp Thr Pro Ile Gln Gly Val Thr Cys Asp Ile
 65                  70                  75                  80

Tyr Asp Glu Leu Trp Tyr Val Thr Ala Leu Ser Phe Gly Thr Met Lys
                 85                  90                  95

Asp Asn Ser Leu Ala Cys Ser Glu Ser Pro Val Ile Arg Pro Gln Leu
            100                 105                 110

Phe Glu Leu Lys His Leu Lys Ser Leu Ser Leu Phe Asn Cys Phe Thr
            115                 120                 125

Thr Pro Asn Arg Tyr Leu Ala Ser Ile Ser Asp Glu Lys Trp Leu Asp
130                 135                 140

Leu Ser Lys Ser Leu Glu Arg Leu Glu Ile Arg Ser Asn Pro Gly Leu
145                 150                 155                 160

Ile Gly Glu Leu Pro Ser Val Ile Thr Asn Leu Thr Asn Leu Gln Ser
                165                 170                 175

Leu Val Val Leu Glu Asn Lys Leu Thr Gly Pro Leu Pro Val Asn Leu
            180                 185                 190

Ala Lys Leu Thr Arg Leu Arg Arg Leu Val Leu Ser Gly Asn Arg Phe
            195                 200                 205

Thr Gly Arg Ile Pro Glu Val Tyr Gly Leu Thr Gly Leu Leu Ile Leu
210                 215                 220

Asp Val Ser Arg Asn Phe Leu Ser Gly Ala Leu Pro Leu Ser Val Gly
225                 230                 235                 240

Gly Leu Tyr Ser Leu Leu Lys Leu Asp Leu Ser Asn Asn Tyr Leu Glu
                245                 250                 255

Gly Lys Leu Pro Arg Glu Leu Glu Ser Leu Lys Asn Leu Thr Leu Leu
            260                 265                 270

Asp Leu Arg Asn Asn Arg Leu Ser Gly Gly Leu Ser Lys Glu Ile Gln
            275                 280                 285

Glu Met Thr Ser Leu Val Glu Leu Val Leu Ser Asn Asn Arg Leu Ala
            290                 295                 300

Gly Asp Leu Thr Gly Ile Lys Trp Arg Asn Leu Lys Asn Leu Val Val
305                 310                 315                 320

Leu Asp Leu Ser Asn Thr Gly Leu Lys Gly Glu Ile Pro Gly Ser Ile
                325                 330                 335

Leu Glu Leu Lys Lys Leu Arg Phe Leu Gly Leu Ser Asn Asn Asn Leu
            340                 345                 350

Gly Gly Lys Leu Ile Pro Gln Met Glu Thr Glu Met Pro Ser Leu Ser
            355                 360                 365

Ala Leu Tyr Val Asn Gly Asn Asn Ile Ser Gly Glu Leu Glu Phe Ser
370                 375                 380

Arg Tyr Phe Tyr Glu Arg Met Gly Arg Arg Leu Gly Val Trp Gly Asn
385                 390                 395                 400

Pro Asn Leu Cys Tyr Asn Gly Asp Glu Thr Lys Asn Leu Ser Asp His
                405                 410                 415

Val Pro Phe Gly Val Asn Gln Cys Lys Arg Ile Lys Ala Asp Lys Tyr
            420                 425                 430
```

<210> SEQ ID NO 7
<211> LENGTH: 424
<212> TYPE: PRT
<213> ORGANISM: Arabidopsis thaliana

<400> SEQUENCE: 7

```
Met Leu Trp Gln Thr Phe Phe Ser Ser Leu Leu Leu Ser Leu Leu
1               5                   10                  15

Phe Gly Cys Asn Gly Asp Glu Ser Leu Pro Glu Val Thr Asp Ser Glu
            20                  25                  30

Glu Ala Pro Met Asp Lys Arg Glu Arg Glu Ala Leu Tyr Ser Ala Ile
        35                  40                  45

Gln Gly Phe Val Gly Asp Ser Trp Asn Gly Ser Ala Leu Tyr Pro Asp
50                  55                  60

Pro Cys Gly Trp Thr Pro Ile Gln Gly Val Ser Cys Asp Ile Tyr Asn
65                  70                  75                  80

Asp Leu Trp Tyr Val Thr Asp Leu Ser Leu Gly Leu Ile Tyr Glu Asn
                85                  90                  95

Ser Leu Pro Cys Ser Ser Ser Leu Gln Ile Arg Pro Glu Leu Phe Glu
                100                 105                 110

Leu Lys His Leu Arg Ser Leu Ser Phe Phe Asn Cys Phe Ile Ser Pro
            115                 120                 125

Met Val Ile Ala Lys Glu Glu Leu Trp Thr Asn Phe Ala Ser Asn Leu
        130                 135                 140

Glu Ser Leu Glu Phe Arg Ser Asn Pro Gly Leu Ile Gly Glu Leu Pro
145                 150                 155                 160

Glu Thr Ile Gly Asn Leu Thr Lys Leu Lys Ser Leu Val Val Leu Glu
                165                 170                 175

Asn Gly Phe Ser Gly Glu Leu Pro Ala Ser Ile Cys Asn Leu Lys Arg
                180                 185                 190

Leu Lys Arg Leu Val Phe Ala Gly Asn Ser Phe Ala Gly Met Ile Pro
            195                 200                 205

Asn Cys Phe Lys Gly Leu Lys Glu Leu Leu Ile Leu Asp Leu Ser Arg
        210                 215                 220

Asn Ser Phe Ser Gly Thr Leu Pro Thr Ser Phe Gly Asp Leu Val Ser
225                 230                 235                 240

Leu Leu Lys Leu Asp Leu Ser Asn Asn Leu Leu Glu Gly Asn Leu Pro
                245                 250                 255

Gln Glu Leu Gly Phe Leu Lys Asn Leu Thr Leu Leu Asp Leu Arg Asn
                260                 265                 270

Asn Arg Phe Ser Gly Gly Leu Ser Lys Asn Ile Glu Asn Ile Gln Ser
            275                 280                 285

Leu Thr Glu Leu Val Leu Ser Asn Asn Pro Met Gly Glu Glu Asp Met
        290                 295                 300

Val Gly Thr Asn Trp Gly Lys Met Ser Asn Leu Val Val Leu Asp Leu
305                 310                 315                 320

Ser Lys Met Gly Leu Arg Gly Glu Ile Pro Thr Ser Leu Thr Asn Leu
                325                 330                 335

Lys Arg Leu Arg Phe Leu Gly Leu Asn Asn Asn Asn Leu Thr Gly Phe
                340                 345                 350

Val Pro Ser Lys Lys Leu Glu Ala Leu Pro Cys Leu Gly Ala Leu Tyr
            355                 360                 365

Ile Asn Gly Asn Asn Leu Thr Gly Glu Leu Arg Phe Ser Thr Lys Phe
        370                 375                 380

Tyr Glu Lys Met Gly Arg Arg Phe Lys Ala Ser Lys Asn Pro Asn Leu
385                 390                 395                 400

Cys Gln Pro Leu Glu Met Val Met Ser Glu Ser His Lys His Leu Ser
                405                 410                 415
```

```
Pro Leu Gly Val Lys Pro Cys Thr
            420

<210> SEQ ID NO 8
<211> LENGTH: 475
<212> TYPE: PRT
<213> ORGANISM: Arabidopsis thaliana

<400> SEQUENCE: 8

Met Ser Trp Ile His Leu Val Leu Phe Leu Cys Leu Thr Leu Cys
1               5                   10                  15

Cys Val Thr Gly Glu Leu Ser Pro Glu Gly Thr Asp Asp Gly Ala Pro
            20                  25                  30

Met Glu Lys Thr Glu Gln Glu Ala Leu Tyr Ser Ala Ile Gln Gly Phe
            35                  40                  45

Val Gly Asp Ser Trp Asn Gly Ser Asp Leu Tyr Pro Asp Pro Cys Gly
    50                  55                  60

Trp Thr Pro Ile Gln Gly Val Ser Cys Asp Leu Tyr Gly Asp Leu Trp
65                  70                  75                  80

Tyr Val Thr Asp Leu Thr Leu Gly Leu Val His Glu Asn Ser Leu Ser
                85                  90                  95

Cys Ala Thr Ser Leu Glu Ile Lys Pro Gln Leu Phe Lys Leu Lys His
            100                 105                 110

Leu Lys Ser Leu Thr Phe Phe Asn Cys Phe Thr Ser Pro Ile Arg Ile
            115                 120                 125

Pro Lys Glu Asp Trp Ile Asn Leu Ala Ser Asn Leu Glu Ser Leu Glu
            130                 135                 140

Phe Arg Ser Asn Pro Gly Leu Ile Gly Glu Leu Pro Glu Thr Ile Gly
145                 150                 155                 160

Ser Leu Thr Lys Leu Lys Ser Leu Val Val Leu Glu Asn Gly Phe Asn
                165                 170                 175

Gly Lys Leu Pro Thr Arg Ile Cys Asn Leu Thr Arg Leu Lys Arg Leu
            180                 185                 190

Val Leu Ala Gly Asn Leu Phe Thr Gly Thr Ile Pro Asp Cys Phe Asn
            195                 200                 205

Gly Phe Lys Asp Leu Leu Ile Leu Asp Met Ser Arg Asn Ser Phe Ser
            210                 215                 220

Gly Ile Leu Pro Leu Ser Val Gly Glu Met Val Ser Leu Leu Lys Leu
225                 230                 235                 240

Asp Leu Ser Asn Asn Gln Leu Glu Gly Arg Leu Pro Gln Glu Ile Gly
                245                 250                 255

Phe Leu Lys Asn Leu Thr Leu Leu Asp Leu Arg Asn Asn Arg Ile Ser
            260                 265                 270

Gly Gly Leu Phe Glu Asn Ile Glu Lys Ile Pro Ser Leu Thr Asp Leu
            275                 280                 285

Val Leu Ser Gly Asn Pro Met Gly Ser Asp Asp Met Met Gly Ile Lys
            290                 295                 300

Trp Glu Asn Met Gly Asn Leu Val Ile Leu Asp Leu Ser Lys Met Gly
305                 310                 315                 320

Leu Arg Gly Glu Val Pro Leu Gly Leu Thr Ser Leu Arg Arg Leu Arg
                325                 330                 335

Phe Leu Gly Leu Asn Asp Asn Asn Leu Thr Gly Thr Val Pro Ser Lys
            340                 345                 350

Glu Leu Glu Thr Leu Pro Cys Leu Gly Ala Leu Tyr Ile Asn Gly Asn
            355                 360                 365
```

```
Asn Leu Ser Gly Glu Leu Arg Phe Ser Arg Lys Phe Tyr Glu Lys Met
            370                 375                 380

Gly Thr Arg Phe Lys Ala Ser Lys Asn Pro Asn Leu Cys Gln Asp Val
385                 390                 395                 400

Val Ser Glu Ser Arg Gln Tyr Val Val Gly Leu Lys Ser Cys Met Met
                405                 410                 415

Glu Lys Ala Glu Asp Ser Leu Val Ile Lys Gln Thr Trp Ser Asn Leu
            420                 425                 430

Lys Lys Glu Asp Glu Ser Ser Ser Met Gly Val Met Val Thr Arg
            435                 440                 445

His Val Leu Leu Ser Asn Gly Phe Met Trp Asp Leu Leu Leu Glu Leu
            450                 455                 460

Ser Leu Ile Leu Leu Asn Leu Leu Val Cys
465                 470                 475
```

<210> SEQ ID NO 9
<211> LENGTH: 477
<212> TYPE: PRT
<213> ORGANISM: Oryza sativa

<400> SEQUENCE: 9

```
Met Arg Gln Pro Gln Ser Arg Lys Leu Leu Gln Leu Gln Ala Leu Ser
1               5                   10                  15

Leu Leu Leu Phe Ile Ile Ala Leu His Ser Arg Leu His Gly Cys Ser
            20                  25                  30

Gly Gln Gly Glu Ala Ala Asp Gly Ser Ala Ser Thr Ala Ala Ala Pro
        35                  40                  45

Met Glu Glu Lys Glu Lys Arg Ala Leu Tyr Ala Ala Ile Glu Gly Phe
50                  55                  60

Val Gly Lys Gly Trp Asn Gly Ser Ala Leu Tyr Pro Asp Pro Cys Gly
65                  70                  75                  80

Trp Ser Pro Ile Gln Gly Val Ser Cys Asp Leu Phe Asn Gly Leu Trp
                85                  90                  95

Tyr Pro Thr Val Met Ser Ile Gly Pro Val Leu Asp Asn Ser Leu Arg
            100                 105                 110

Cys Ser Ala Asp Ala Lys Phe Ser Pro Gln Leu Phe Asp Leu Lys Arg
        115                 120                 125

Leu Lys Thr Leu Ser Phe Tyr Ser Cys Phe Pro Ala Thr Asn Pro Thr
130                 135                 140

Pro Ile Pro Ala Thr Ser Trp Asp Lys Leu Ala Gly Ser Leu Glu Thr
145                 150                 155                 160

Leu Glu Phe Arg Thr Asn Pro Gly Leu Thr Gly Pro Ile Pro Ala Ser
                165                 170                 175

Leu Gly Arg Leu Ser Ser Leu Gln Ser Leu Val Phe Glu Asn Asn
            180                 185                 190

Leu Thr Gly Ala Val Pro Ala Glu Leu Gly Ser Leu Val Arg Leu Arg
        195                 200                 205

Arg Leu Val Leu Ser Gly Asn Gly Leu Ser Gly Gln Ile Pro Ala Ser
210                 215                 220

Leu Gly Asn Gly His Phe Ala Glu Gln Leu Leu Ile Met Asp Val Ser
225                 230                 235                 240

Asn Asn Ser Leu Thr Gly Ser Leu Pro Ser Ser Leu Gly Gly Leu Lys
                245                 250                 255

Gly Leu Leu Lys Met Asp Leu Ser Asn Asn Leu Leu Gln Gly Ser Leu
```

```
               260                 265                 270
Pro Pro Glu Leu Ala Gly Leu Gly Ser Leu Thr Leu Leu Asp Leu Arg
            275                 280                 285

Asn Asn Ser Phe Thr Gly Gly Leu Pro Ser Phe Leu Gln Gly Met Ala
        290                 295                 300

Ser Leu Gln Asp Leu Leu Ser Asn Asn Pro Leu Gly Gly Ser Leu
305                 310                 315                 320

Gly Gln Leu Gly Trp Glu Arg Leu Arg Gly Leu Ala Thr Leu Asp Leu
                325                 330                 335

Ser Asn Leu Gly Leu Val Gly Ala Ile Pro Glu Ser Met Ala Ala Leu
            340                 345                 350

Thr Arg Leu Arg Phe Leu Ala Leu Asp His Asn Arg Leu Thr Gly Asp
        355                 360                 365

Val Pro Ala Arg Leu Ala Glu Leu Pro Asn Ile Gly Ala Leu Tyr Leu
    370                 375                 380

Asn Gly Asn Asn Leu Thr Gly Thr Leu Gln Phe Ser Pro Ala Phe Tyr
385                 390                 395                 400

Gln Arg Met Gly Arg Arg Phe Ala Ser Trp Asp Asn Pro Gly Leu Cys
                405                 410                 415

Tyr Ser Asn Ala Ala Val Asp Ala Ala His Ala Pro Pro Gly Val Thr
            420                 425                 430

Val Cys Lys Val Ala Gly Gly Val Gly Asp Gly Arg Lys Pro Glu Ala
        435                 440                 445

Ser Ser Ser Leu Met Ala Thr Ser Ser Ala Ser Asn Leu Ile Asn Gly
    450                 455                 460

Phe Cys Phe Phe Leu Trp Met Val Ala Thr Ser Leu Leu
465                 470                 475

<210> SEQ ID NO 10
<211> LENGTH: 516
<212> TYPE: PRT
<213> ORGANISM: Sorghum bicolor

<400> SEQUENCE: 10

Met Arg Pro Ala Gly Gly Cys Cys Arg Arg Gly Gly Gly Leu Leu Val
1               5                   10                  15

Leu Gly Leu Ala Leu Ser Leu Ser Ala Ala Leu Leu Leu Arg Gly Cys
            20                  25                  30

Ala Gly Gln Gln Ala Glu Asp Asp Gly Ser Ala Asp Ala Pro Ala Ala
        35                  40                  45

Ala Ala Ala Ala Thr Ala Pro Met Glu Glu Lys Glu Arg Arg Ala
    50                  55                  60

Leu Tyr Ala Ala Ile Glu Ser Phe Val Gly Lys Gly Trp Asn Gly Ser
65                  70                  75                  80

Gly Leu Tyr Pro Asp Pro Cys Gly Trp Ser Pro Ile Gln Gly Val Ser
                85                  90                  95

Cys Asp Leu Phe Asn Gly Leu Trp Tyr Pro Thr Val Met Ser Ile Gly
            100                 105                 110

Pro Val Leu Asp Asn Ser Leu Gln Cys Ala Pro Asp Ala Lys Phe Ser
        115                 120                 125

Pro Gln Leu Phe Asp Leu Arg Arg Leu Arg Thr Leu Ser Phe Tyr Ser
    130                 135                 140

Cys Phe Pro Ala Ser Asn Pro Thr Ala Ile Pro Thr Ala Gly Trp Glu
145                 150                 155                 160
```

```
Lys Leu Ser Gly Thr Leu Glu Thr Leu Glu Phe Arg Thr Asn Pro Gly
            165                 170                 175

Leu Thr Gly Gly Ile Pro Pro Ser Leu Gly Arg Leu Ala Ser Leu Gln
        180                 185                 190

Ser Leu Val Leu Val Glu Asn Asn Leu Thr Gly Pro Val Pro Ala Glu
        195                 200                 205

Leu Gly Ala Leu Ser Arg Leu Arg Arg Leu Val Leu Ser Gly Asn Gly
        210                 215                 220

Leu Ser Gly Pro Ile Pro Ala Thr Leu Gly Asn Asn Asn Asp Arg Arg
225                 230                 235                 240

His Arg His Ala His Asp Asp Glu Leu Leu Ile Val Asp Leu Ser Arg
                245                 250                 255

Asn Ser Leu Thr Gly Ser Leu Pro Ser Ser Leu Gly Gly Leu Thr Gly
            260                 265                 270

Leu Leu Lys Met Asp Leu Ser Asn Asn Leu Leu Gln Gly Ser Ile Pro
        275                 280                 285

Pro Glu Leu Ala Gly Leu Lys Ser Leu Thr Leu Leu Asp Leu Arg Asn
        290                 295                 300

Asn Ser Leu Thr Gly Gly Leu Pro Gln Phe Val Gln Cys Met Ala Ser
305                 310                 315                 320

Leu Gln Asp Leu Leu Leu Ser Asn Asn Pro Gln Leu Gly Gly Ala Leu
                325                 330                 335

Pro Gln Ser Gly Trp Glu Thr Leu Ala Ala Asn Leu Ala Thr Leu Asp
            340                 345                 350

Leu Ser Asn Val Gly Leu Val Gly Ala Ile Pro Ala Ser Met Ala Lys
        355                 360                 365

Leu Thr Gly Leu Arg Phe Leu Ala Leu Asp His Asn Arg Leu Thr Gly
        370                 375                 380

Ala Val Pro Ala Glu Leu Asp Gln Leu Pro Ser Ile Gly Ala Leu Tyr
385                 390                 395                 400

Leu Asn Gly Asn Asn Leu Thr Gly Pro Leu Gln Phe Ser Pro Gly Phe
                405                 410                 415

Tyr Gln Arg Met Gly Arg Arg Phe Ala Ser Trp Asp Asn Pro Gly Leu
            420                 425                 430

Cys Tyr Asn Ile Ala Ala Val Asp Ala Ala His Ala Pro Ser Gly Val
        435                 440                 445

Val Val Cys Lys Asp Leu Gln Glu Pro Ser Val Ala Arg Asp Gly Asp
        450                 455                 460

Gly Glu Glu Glu Gly Gly Arg Lys Pro Glu Ala Ser Ser Ser Leu Val
465                 470                 475                 480

Ala Ser Ser Ser Gly Gly Phe Val Gly Ser Val Gly Gly His Trp
                485                 490                 495

Tyr Leu Val Val Val Gln Gly Met Ala Ala Ala Val Leu Gly Leu Leu
            500                 505                 510

Ser Gln Leu Leu
        515

<210> SEQ ID NO 11
<211> LENGTH: 512
<212> TYPE: PRT
<213> ORGANISM: Sorghum bicolor

<400> SEQUENCE: 11

Met Arg Pro Ala Gly Gly Cys Cys Arg Arg Gly Gly Gly Leu Leu Val
1               5                   10                  15
```

```
Leu Gly Leu Ala Leu Ser Leu Ser Ala Ala Leu Leu Leu Arg Cys Cys
         20                  25                  30

Ala Gly Gln Gln Ala Glu Asp Asp Gly Ser Ala Asp Ala Pro Ala Ala
         35                  40                  45

Ala Thr Ala Pro Met Glu Glu Lys Glu Arg Arg Ala Leu Tyr Ala Ala
         50                  55                  60

Ile Glu Ser Phe Val Gly Lys Gly Trp Asn Gly Ser Gly Leu Tyr Pro
 65                  70                  75                  80

Asp Pro Cys Gly Trp Ser Pro Ile Gln Gly Val Ser Cys Asp Leu Phe
                 85                  90                  95

Asn Gly Leu Trp Tyr Pro Thr Val Ile Gly Ile Gly Pro Val Leu Asp
        100                 105                 110

Asn Ser Leu Gln Cys Ala Pro Asp Ala Lys Phe Ser Pro Gln Leu Phe
        115                 120                 125

Asp Leu Arg Arg Leu Arg Thr Leu Ser Phe Tyr Ser Cys Phe Pro Ala
        130                 135                 140

Ser Asn Pro Thr Ala Ile Pro Thr Ala Gly Trp Glu Lys Leu Ser Gly
145                 150                 155                 160

Thr Leu Glu Thr Leu Glu Phe Arg Thr Asn Pro Gly Leu Thr Gly Gly
                165                 170                 175

Ile Pro Pro Ser Leu Gly Arg Leu Ala Ser Leu Gln Ser Leu Val Leu
        180                 185                 190

Val Glu Asn Asn Leu Thr Gly Pro Val Pro Ala Glu Leu Gly Ala Leu
        195                 200                 205

Ser Arg Leu Arg Arg Leu Val Leu Ser Gly Asn Gly Leu Ser Gly Pro
        210                 215                 220

Ile Pro Ala Thr Leu Gly Asn Asn Asn Asp Arg His Arg Arg His Ala
225                 230                 235                 240

His Asp Asp Ala Leu Leu Ile Val Asp Leu Ser Arg Asn Ser Leu Thr
                245                 250                 255

Gly Ser Leu Pro Ser Ser Leu Gly Gly Leu Thr Gly Leu Leu Lys Met
                260                 265                 270

Asp Leu Ser Asn Asn Leu Leu Gln Gly Ser Ile Pro Pro Glu Leu Ala
        275                 280                 285

Gly Leu Lys Ser Leu Thr Leu Leu Asp Leu Arg Asn Asn Ser Leu Thr
        290                 295                 300

Gly Gly Leu Pro Gln Phe Val Gln Gly Met Ala Ser Leu Gln Asp Leu
305                 310                 315                 320

Leu Leu Ser Asn Asn Pro Gln Leu Gly Gly Ala Leu Pro Gln Ser Gly
                325                 330                 335

Trp Glu Thr Leu Ala Ala Asn Leu Ala Thr Leu Asp Leu Ser Asn Val
                340                 345                 350

Gly Leu Val Gly Ala Ile Pro Ala Asn Met Ala Lys Leu Thr Gly Leu
        355                 360                 365

Arg Phe Leu Ala Leu Asp His Asn Arg Leu Thr Gly Ala Val Pro Ala
        370                 375                 380

Glu Leu Ala Gln Leu Pro Ser Ile Gly Ala Leu Tyr Leu Asn Gly Asn
385                 390                 395                 400

Asn Leu Thr Gly Pro Leu Glu Phe Leu Ala Gly Phe Tyr Gln Arg Met
                405                 410                 415

Gly Gln Arg Phe Ala Ser Trp Asp Asn Pro Gly Leu Cys Tyr Asn Ile
        420                 425                 430
```

```
Ala Ala Val Asp Val Ala His Ala Pro Ser Gly Val Val Cys Lys
            435                 440                 445

Asp Leu Gln Glu Pro Ser Val Ala Pro Asp Gly Asp Gly Glu Val Glu
450                 455                 460

Gly Gly Arg Lys Pro Glu Ala Ser Ser Ser Leu Val Ala Ser Ser Ser
465                 470                 475                 480

Ser Gly Gly Ser Ser Ala Arg Val Gly Gly Leu Trp Tyr Leu Val Val
                485                 490                 495

Val Gln Gly Met Val Ala Ala Val Leu Gly Leu Leu Ser Arg Leu Leu
                500                 505                 510

<210> SEQ ID NO 12
<211> LENGTH: 443
<212> TYPE: PRT
<213> ORGANISM: Glycine max

<400> SEQUENCE: 12

Met Glu Lys Ala Glu Gln Glu Ala Leu Tyr Ser Thr Ile Gln Gly Phe
1               5                   10                  15

Val Gly Asp Ser Trp Asn Gly Ser Asp Leu Tyr Pro Asp Pro Cys Gly
                20                  25                  30

Trp Thr Pro Ile Gln Gly Val Ser Cys Asp Leu Phe Asp Gly Phe Trp
            35                  40                  45

Tyr Val Thr Ala Leu Asn Ile Gly Pro Val His Asp Asn Ser Leu Ser
50                  55                  60

Cys Ala Gln Asp Leu Glu Phe Arg Gln His Leu Phe Glu Leu Lys His
65                  70                  75                  80

Leu Lys Ser Leu Ser Phe Phe Asn Cys Ser Gln Ser Gln Tyr Met Phe
                85                  90                  95

Pro Ala Thr Ile Pro Thr Gly Asn Trp Gln Lys Leu Ala Gly Ser Leu
            100                 105                 110

Glu Ser Leu Glu Phe Arg Ser Asn Pro Gly Leu Ile Gly Asn Ile Pro
        115                 120                 125

Ser Ser Phe Gly Val Leu Lys Asn Leu Gln Ser Leu Val Ile Leu Glu
130                 135                 140

Asn Ser Val Thr Gly Glu Ile Pro Ser Ser Ile Gly Asn Leu Ile Lys
145                 150                 155                 160

Leu Lys Lys Leu Val Leu Ala Gly Asn Tyr Leu Thr Gly Arg Ile Pro
                165                 170                 175

Asp Val Phe Asp Gly Leu Asn Glu Leu Leu Ile Phe Asp Leu Ser Ser
            180                 185                 190

Asn Ser Leu Ser Gly Ser Leu Pro Leu Thr Leu Gly Ser Leu Thr Ser
        195                 200                 205

Ala Leu Lys Leu Asp Val Ser Asn Asn His Leu Glu Gly Asn Leu Leu
210                 215                 220

Asn Gln Phe Ala Asn Leu Lys Asn Leu Thr Leu Met Asp Leu Arg Asn
225                 230                 235                 240

Asn Arg Phe Thr Gly Gly Leu Thr Leu Ser Leu Gln Glu Met Ser Ser
                245                 250                 255

Leu Glu Glu Leu Val Leu Ser Asn Asn Pro Leu Gly Gly Asp Val Arg
            260                 265                 270

Phe Leu Lys Trp Glu Asn Leu Lys Asn Leu Ala Ile Leu Glu Leu Ser
        275                 280                 285

Asn Met Gly Leu Thr Gly Glu Ile Pro Glu Ser Leu Ser Glu Leu Lys
        290                 295                 300
```

```
Arg Leu Arg Phe Leu Gly Leu Ser Asp Asn Asn Leu Thr Gly Asn Pro
305                 310                 315                 320

Ser Pro Lys Leu Glu Thr Leu Pro Cys Leu Asn Ala Leu Tyr Leu Ser
            325                 330                 335

Gly Asn Asn Leu Thr Gly Glu Leu Ser Phe Ser Lys Asp Phe Phe Gly
            340                 345                 350

Lys Met Gly Arg Arg Phe Gly Ala Trp Asn Asn Pro Asn Leu Cys Tyr
        355                 360                 365

Gln Ile Gly Leu Met Ser Ser His Val Pro Tyr Gly Val Lys Pro
370                 375                 380

Cys Gln Lys Glu Val Asn Leu Leu Glu Ser Asp Ser Lys Thr Glu Leu
385                 390                 395                 400

Ile Asn Gly Asp Met Asn Glu Thr Phe His Phe Ile Ala Ser Lys Gly
                405                 410                 415

Phe Ser Ser Cys Ala Thr Asn Gly Phe Trp Trp Thr Phe Leu Glu Lys
                420                 425                 430

Ile Leu Met Met Gly Leu Phe Leu Ser Leu Ile
            435                 440
```

<210> SEQ ID NO 13
<211> LENGTH: 395
<212> TYPE: PRT
<213> ORGANISM: Glycine max

<400> SEQUENCE: 13

```
Cys Cys Gly Gln Glu Asp Leu Asp Asn Asp Ile Leu Ala Pro Met Glu
1               5                   10                  15

Lys Ala Glu Gln Glu Ala Leu Tyr Ser Thr Ile Gln Gly Phe Val Gly
            20                  25                  30

Asp Ser Trp Asn Gly Ser Asp Leu Tyr Pro Asp Pro Cys Gly Trp Thr
        35                  40                  45

Pro Ile Gln Gly Val Ser Cys Asp Leu Phe Asp Gly Phe Trp Tyr Val
    50                  55                  60

Thr Ala Leu Asn Ile Gly Pro Val His Asp Asn Ser Leu Ser Cys Ala
65                  70                  75                  80

Gln Glu Leu Glu Phe Arg Arg Glu Leu Phe Glu Leu Lys His Leu Lys
                85                  90                  95

Ala Leu Ser Phe Phe Asn Cys Phe Gln Ser Gln Asp Met Phe Pro Ala
            100                 105                 110

Thr Ile Pro Thr Gly Asn Trp Gln Lys Leu Ala Gly Ser Leu Glu Ser
        115                 120                 125

Leu Glu Phe Arg Ser Asn Pro Gly Leu Ile Gly Asn Ile Pro Ser Ser
130                 135                 140

Phe Ser Ala Leu Lys Asn Leu Gln Ser Leu Val Ile Leu Glu Asn Ser
145                 150                 155                 160

Val Thr Gly Glu Ile Pro Ser Ser Ile Gly Asn Leu Ile Lys Leu Lys
                165                 170                 175

Lys Leu Val Leu Ala Gly Asn Tyr Leu Thr Gly Ser Ile Pro Asp Val
            180                 185                 190

Phe Asp Gly Leu Asn Glu Leu Leu Ile Phe Asp Leu Ser Asn Ser
        195                 200                 205

Leu Ser Gly Ser Leu Pro Leu Thr Leu Gly Ser Leu Thr Ser Ala Leu
210                 215                 220

Lys Leu Asp Val Ser Tyr Asn His Leu Glu Gly Asn Leu Leu Asn Ala
```

```
                225                 230                 235                 240
        Phe Ala Asn Leu Lys Tyr Leu Thr Leu Met Asp Leu Arg Asn Asn Arg
                        245                 250                 255

Phe Thr Gly Gly Leu Thr Leu Ser Leu Gln Glu Met Ser Ser Leu Glu
                        260                 265                 270

Glu Leu Val Leu Ser Asn Asn Pro Leu Gly Gly Asp Ile Arg Phe Leu
                        275                 280                 285

Lys Trp Glu Asn Leu Asn Asn Leu Ala Ile Leu Glu Leu Ser Asn Met
                        290                 295                 300

Gly Leu Thr Gly Glu Ile Pro Glu Ser Leu Ser Glu Leu Lys Leu Leu
        305                 310                 315                 320

Arg Phe Leu Gly Leu Ser Asp Asn Asn Leu Thr Gly Asn Leu Ser Pro
                        325                 330                 335

Lys Leu Glu Thr Leu Pro Cys Leu Asn Ala Leu Tyr Leu Ser Gly Asn
                        340                 345                 350

Asn Leu Thr Gly Glu Ile Asn Phe Ser Lys Asp Phe Phe Gly Lys Met
                        355                 360                 365

Gly Arg Arg Phe Gly Ala Trp Asn Asn Pro Asn Leu Cys Tyr Gln Ile
        370                 375                 380

Gly Leu Met Ser Ser Ser His Val Pro Phe Gly
        385                 390                 395

<210> SEQ ID NO 14
<211> LENGTH: 385
<212> TYPE: PRT
<213> ORGANISM: Glycine max

<400> SEQUENCE: 14

Met Ala Pro Met Glu Lys Ala Glu Arg Asp Ala Leu Tyr Ser Thr Ile
        1               5                   10                  15

Gln Gly Phe Val Gly Asn Trp Trp Asn Gly Ser Asp Leu Tyr Pro Asp
                        20                  25                  30

Pro Cys Gly Trp Thr Pro Ile Gln Gly Val Ser Cys Asp Leu Phe Asn
                        35                  40                  45

Gly Phe Trp Tyr Val Thr Val Leu Asn Ile Gly Pro Ile His Asp Asn
                50                  55                  60

Ser Leu Ser Cys Ala Lys Asn Leu Glu Phe Arg Pro Gln Leu Phe Glu
        65                  70                  75                  80

Leu Lys His Leu Lys Ala Leu Ser Leu Phe Lys Cys Phe Glu Ser Gln
                        85                  90                  95

His Lys His His Gln Ala Thr Ile Pro Asn Ala His Trp Glu Lys Leu
                        100                 105                 110

Ala Gly Ser Leu Glu Ser Leu Glu Tyr Arg Ser Asn Arg Gly Leu Ile
                        115                 120                 125

Gly Lys Ile Pro Ser Ser Phe Gly Ala Leu Lys Asn Leu Gln Ser Leu
                        130                 135                 140

Val Val Leu Glu Asn Gly Leu Thr Gly Glu Ile Pro Pro Asp Ile Gly
        145                 150                 155                 160

Asn Leu Asn Lys Leu Lys Arg Leu Val Leu Ala Gly Asn Tyr Phe Ser
                        165                 170                 175

Gly His Ile Pro Asp Ile Phe Ser Ala Leu Ser Asp Leu Leu Ile Leu
                        180                 185                 190

Asp Leu Ser Arg Asn Ser Leu Ser Gly Thr Leu Pro Ser Thr Leu Gly
                        195                 200                 205
```

```
Ser Leu Thr Ser Leu Leu Lys Leu Asp Val Ser His Asn His Leu Glu
    210                 215                 220
Gly Asn Leu Leu Lys Glu Leu Ala Asp Leu Lys Asn Leu Thr Leu Met
225                 230                 235                 240
Asp Leu Arg Asn Asn Arg Phe Ser Gly Gly Leu Thr Leu Ser Ile Gln
                245                 250                 255
Asp Met Tyr Ser Leu Glu Glu Met Val Leu Ser Asn Asn Gly Ile Gly
            260                 265                 270
Gly Asp Ile Arg Thr Leu Lys Trp Glu Asn Leu His Asn Leu Val Ile
        275                 280                 285
Leu Asp Leu Ser Asn Met Gly Leu Lys Gly Glu Ile Pro Glu Ser Met
    290                 295                 300
Ser Glu Leu Lys Arg Leu Arg Phe Leu Gly Leu Ser Asp Asn Asn Leu
305                 310                 315                 320
Thr Gly Asn Leu Ser Pro Lys Leu Ser Thr Leu Pro Cys Leu Asn Ala
                325                 330                 335
Leu Tyr Val Ser Gly Asn Asn Leu Val Gly Leu Lys Phe Ser Met
            340                 345                 350
Glu Phe Tyr Gly Lys Met Gly Thr Arg Phe Gly Ala Trp Asn Asn Pro
        355                 360                 365
Ser Leu Cys Tyr His Leu Gly Val Met Ser Thr Ser His Val Pro Tyr
    370                 375                 380
Gly
385

<210> SEQ ID NO 15
<211> LENGTH: 408
<212> TYPE: PRT
<213> ORGANISM: Glycine max

<400> SEQUENCE: 15

Met Ala Pro Met Glu Lys Ala Glu Arg Asp Ala Leu Tyr Ser Thr Ile
1               5                   10                  15
Gln Gly Phe Val Gly Asp Trp Trp Asn Gly Ser Asp Leu Tyr Pro Asp
            20                  25                  30
Pro Cys Gly Trp Thr Pro Ile Gln Gly Val Ser Cys Asp Leu Phe Asn
        35                  40                  45
Gly Phe Trp Tyr Val Thr Val Leu Asn Ile Gly Pro Ile His Asp Asn
    50                  55                  60
Ser Leu Ser Cys Ala Lys Ile Leu Glu Phe Arg Pro Gln Leu Phe Glu
65                  70                  75                  80
Leu Lys His Leu Lys Ala Leu Ser Leu Phe Lys Cys Phe Glu Ser Gln
                85                  90                  95
His Arg His Gln Val Thr Ile Pro Asn Ala Asn Trp Glu Lys Leu Ala
            100                 105                 110
Gly Ser Leu Glu Ser Leu Glu Phe Arg Ser Asn Arg Gly Leu Ile Gly
        115                 120                 125
Lys Ile Pro Ser Ser Phe Gly Ala Leu Lys Asn Leu Gln Ser Leu Val
    130                 135                 140
Leu Leu Glu Asn Gly Leu Thr Gly Lys Ile Pro Pro Asp Ile Gly Lys
145                 150                 155                 160
Leu Asn Lys Leu Lys Arg Leu Val Leu Ala Gly Asn His Phe Ser Gly
                165                 170                 175
His Ile Pro Asp Ile Phe Ser Ala Leu Gly Glu Leu Leu Ile Leu Asp
            180                 185                 190
```

```
Leu Ser Arg Asn Ser Leu Ser Gly Thr Leu Pro Leu Thr Leu Gly Ser
            195                 200                 205

Leu Thr Ser Leu Leu Lys Leu Asp Val Ser His Asn His Leu Glu Gly
210                 215                 220

Asn Leu Leu Lys Glu Phe Ala Tyr Leu Lys Asn Leu Thr Leu Met Asp
225                 230                 235                 240

Leu Arg Asn Asn Arg Phe Ser Gly Gly Leu Thr Leu Ser Ile Gln Glu
                245                 250                 255

Met Tyr Ser Leu Glu Glu Met Val Leu Ser Asn Asn Ala Ile Gly Gly
            260                 265                 270

Asp Ile Arg Thr Leu Lys Trp Glu Asn Leu His Asn Leu Ile Ile Leu
        275                 280                 285

Asp Leu Ser Asn Met Gly Leu Lys Gly Glu Ile Pro Glu Ser Ile Ser
290                 295                 300

Glu Leu Lys Arg Leu Arg Phe Leu Gly Leu Ser Asp Asn Asn Leu Thr
305                 310                 315                 320

Gly Asn Leu Ser Pro Asn Leu Ser Thr Leu Pro Cys Leu Asn Ala Leu
                325                 330                 335

Tyr Val Ser Gly Asn Asn Leu Thr Gly Glu Leu Lys Phe Ser Val Glu
            340                 345                 350

Phe Tyr Gly Lys Met Arg Thr Arg Phe Gly Ala Trp Asn Asn Pro Ser
        355                 360                 365

Leu Cys Tyr Pro Leu Gly Val Ile Ser Thr Ser His Val Pro Tyr Gly
370                 375                 380

Arg Thr Phe His Ser Ile Ala Ser Leu Ser His Thr Pro Asn Ser Phe
385                 390                 395                 400

Cys Trp His Asp Leu Thr Ile Gly
                405

<210> SEQ ID NO 16
<211> LENGTH: 454
<212> TYPE: PRT
<213> ORGANISM: Glycine max

<400> SEQUENCE: 16

Met Gln Ser Ala Cys Arg Phe Cys Leu Gln Tyr Asp Ser Gly Gln Asp
1               5                   10                  15

Ser Ser Phe Ser Pro Met Lys Asn Lys Glu Lys Glu Ala Ile Tyr Ser
            20                  25                  30

Val Ile Gln Gly Phe Val Gly Lys Trp Trp Asn Gly Ser Tyr Leu Tyr
        35                  40                  45

Pro Asp Pro Cys Gly Trp Thr Pro Val Gln Gly Val Ser Cys Glu Gln
    50                  55                  60

Tyr Asp Asp Gly Phe Trp Tyr Val Ser Thr Val Asn Phe Gly Pro Val
65                  70                  75                  80

Phe Asp Asn Ser Leu Val Cys Ser His Glu Ala Gln Phe Pro Gln Gln
                85                  90                  95

Leu Phe Asn Leu Lys His Leu Lys Val Leu Ser Leu Ser Thr Cys Phe
            100                 105                 110

His Ser Pro Thr Lys Asn Pro Val Lys Leu Pro Leu Ser Lys Trp Asp
        115                 120                 125

Lys Phe Ser His Ser Leu Glu Ser Leu Thr Leu Arg Ser Asn Pro Gly
    130                 135                 140

Leu Val Gly Thr Ile Pro Pro Ala Ile Gly Ser Leu Lys Asn Leu Gln
```

```
            145                 150                 155                 160
Ser Leu Leu Leu Leu Glu Asn Gly Leu Ser Gly Glu Leu Pro Leu Ser
                165                 170                 175

Ile Gly Asn Leu Val Lys Leu Arg Gln Leu Val Leu Ala Gly Asn Asn
            180                 185                 190

Leu Glu Gly Glu Val Pro Ala Asn Tyr Gly Arg Leu Ser Glu Leu Leu
            195                 200                 205

Ile Phe Asp Ala Ser Arg Asn Asn Leu Ser Gly Val Phe Pro Ser Thr
        210                 215                 220

Leu Gly Leu Leu Asp Ser Leu Lys Leu Asp Phe Ser Asn Asn Met
225                 230                 235                 240

Leu Glu Gly Glu Leu Pro Arg Glu Leu Gly Arg Leu Lys Asn Leu Thr
                245                 250                 255

Leu Leu Asp Ile Ser His Asn Lys Leu Arg Gly Gly Leu Val Arg Thr
            260                 265                 270

Ile Lys Glu Leu Val Ser Leu Lys His Leu Val Leu Ser Asn Asn Pro
        275                 280                 285

Ile Gly Gly Asp Leu Leu Gly Val Lys Trp Glu Asn Phe Gln Asn Leu
        290                 295                 300

Glu Ala Leu Asp Leu Ser Asn Ile Gly Leu Glu Gly Ser Val Pro Lys
305                 310                 315                 320

Ser Met Ala Lys Met Lys Arg Leu Arg Phe Leu Asp Leu Ser Asn Asn
                325                 330                 335

Asp Leu Cys Gly Ser Leu Ser Arg Ser Leu Glu Lys Leu Pro Cys Leu
            340                 345                 350

Thr Ala Leu His Val Asn Gly Asn Asn Leu Thr Gly Arg Leu Glu Phe
            355                 360                 365

Ser Glu Arg Phe Tyr Met Lys Met Gly Met Arg Phe Ala Ala Trp Asn
        370                 375                 380

Asn Thr Asn Leu Cys Cys Met Ala Lys Pro Thr Thr His Glu Met Pro
385                 390                 395                 400

Tyr Gly Val Lys Pro Trp Val Ser Thr Val Lys Met Ser Glu Gly Asn
                405                 410                 415

Tyr Glu Asp Ser Phe Val Val Ala Ser Leu Gly Gly Ser Gly Phe Tyr
            420                 425                 430

Tyr Gly Leu Trp Cys Leu Phe Thr Val Asn Gly Val Leu Tyr Val Phe
        435                 440                 445

Leu Trp Asp Met Leu Phe
    450

<210> SEQ ID NO 17
<211> LENGTH: 434
<212> TYPE: PRT
<213> ORGANISM: Glycine max

<400> SEQUENCE: 17

Met Asn Val Lys Gly Gln Asp Ser Ser Phe Ser Ser Met Lys Asn Lys
1               5                   10                  15

Glu Lys Glu Val Ile Tyr Ser Val Ile Gln Gly Leu Val Gly Lys Trp
            20                  25                  30

Trp Asn Gly Ser Tyr Leu Tyr Pro Asp Pro Cys Gly Arg Thr Pro Ile
        35                  40                  45

Gln Gly Val Ser Cys Glu Gln Tyr Asp Asp Gly Phe Trp Tyr Val Thr
    50                  55                  60
```

```
Thr Val Asn Phe Gly Pro Val Phe Asp Asn Ser Leu Asn Cys Asn His
 65                  70                  75                  80

Glu Ala Gln Phe Pro Gln Gln Leu Phe Asn Leu Lys His Leu Lys Val
                 85                  90                  95

Leu Ser Leu Ser Thr Cys Phe Leu Ser Pro Thr Lys Asn Pro Val Lys
            100                 105                 110

Leu Pro Leu Ser Asn Trp Glu Lys Phe Ser His Ser Leu Glu Ser Leu
        115                 120                 125

Thr Leu Arg Ser Asn Pro Gly Leu Val Gly Thr Ile Pro Ser Ala Ile
    130                 135                 140

Gly Ser Leu Lys Lys Leu Gln Ser Leu Val Leu Glu Asn Gly Leu
145                 150                 155                 160

Thr Gly Glu Leu Pro Leu Ser Ile Gly Asn Leu Val Lys Leu Arg Gln
                165                 170                 175

Leu Val Leu Gln Gly Asn Asn Leu Glu Gly Gln Val Pro Ala Asn Tyr
            180                 185                 190

Gly Trp Leu Ser Glu Leu Leu Ile Phe Asp Ala Ser Arg Asn Asn Leu
        195                 200                 205

Ser Gly Val Leu Pro Ser Thr Leu Gly Leu Leu Asp Ser Leu Leu Lys
210                 215                 220

Leu Asp Leu Ser Asn Asn Met Leu Glu Gly Glu Leu Pro Arg Glu Leu
225                 230                 235                 240

Gly Arg Leu Lys Asn Leu Thr Leu Leu Asp Ile Ser His Ser Lys Leu
                245                 250                 255

Arg Gly Gly Leu Val Arg Thr Ile Lys Glu Leu Val Ser Leu Lys His
            260                 265                 270

Leu Val Leu Ser Asn Asn Pro Ile Gly Gly Asp Leu Leu Gly Val Lys
        275                 280                 285

Trp Glu Asn Phe Gln Asn Ile Glu Ala Leu Asp Leu Ser Asn Ile Gly
    290                 295                 300

Leu Glu Gly Ser Val Pro Glu Ser Met Ala Lys Met Lys Arg Leu Arg
305                 310                 315                 320

Phe Leu Asp Leu Ser Asn Asn Asn Leu Cys Gly Thr Leu Ser Arg Ser
                325                 330                 335

Leu Glu Lys Leu Pro Cys Leu Thr Ala Leu His Val Asn Gly Asn Asn
            340                 345                 350

Leu Thr Gly Arg Leu Glu Phe Ser Asp Arg Phe Tyr Met Lys Leu Gly
        355                 360                 365

Met Arg Phe Ala Ala Trp Asn Asn Ala Asn Leu Cys Cys Asn Ile Ala
    370                 375                 380

Lys Pro Gln Asn Glu Met Pro Tyr Gly Met Ser Glu Gly Asn Tyr Glu
385                 390                 395                 400

Asp Ser Phe Ala Ser Leu Gly Ser Gly Phe Tyr Tyr Gly Leu Trp
                405                 410                 415

Trp Val Phe Thr Val Asn Gly Val Leu Asn Val Leu Leu Trp Asn Met
                420                 425                 430

Leu Phe

<210> SEQ ID NO 18
<211> LENGTH: 645
<212> TYPE: DNA
<213> ORGANISM: Asclepias syriaca
<220> FEATURE:
<221> NAME/KEY: misc_feature
<222> LOCATION: (236)..(236)
```

<223> OTHER INFORMATION: n is a, c, g, or t

<400> SEQUENCE: 18

```
ggggagggag gaagagaacc ttgtttctttt ttggattctt tcacaaaatc tgttcttacc      60
atttttggaa ttggaaatag aaatgaagaa taattctcga aaaatattct atggtttcct     120
tatattatta ccttacatttt tcggctggag tggagctgat agtgtcagtg tcatagcgcc    180
aatggaggaa aatgagcaat tggcacttta ctcaactgtt caagacttca tagganagga    240
ttggaatggt tctgaacttt atcctgatcc ttgtggatgg acaccaatac agggagtttc    300
ttgtgatttc ttcaatggat tctggcatgt tacagattta agccttggac aagtatatga    360
caactctctc aactgttctt caactgcaga atttggatat caccattttg agctcaaata    420
tttgagaaag ctgacctttta cagattgctt cctttcatct caccggaaac ctgtcaaaat    480
tccagaatca agatgggaga gactggcgta caccttagaa catttagaat ttcgatctaa    540
tccaggtcta acgggcggaa ttcccaccgc cttaggctgt ctaacaaagc ttgaatccct    600
tgtgctgata gaaaatgccc taacagggaa ttgccgcctg aaata                    645
```

<210> SEQ ID NO 19
<211> LENGTH: 187
<212> TYPE: PRT
<213> ORGANISM: Asclepias syriaca
<220> FEATURE:
<221> NAME/KEY: misc_feature
<222> LOCATION: (52)..(52)
<223> OTHER INFORMATION: Xaa can be any naturally occurring amino acid

<400> SEQUENCE: 19

Met Lys Asn Asn Ser Arg Lys Ile Phe Tyr Gly Phe Leu Ile Leu Leu
1               5                   10                  15

Pro Tyr Ile Phe Gly Trp Ser Gly Ala Asp Ser Val Ser Val Ile Ala
            20                  25                  30

Pro Met Glu Glu Asn Glu Gln Leu Ala Leu Tyr Ser Thr Val Gln Asp
        35                  40                  45

Phe Ile Gly Xaa Asp Trp Asn Gly Ser Glu Leu Tyr Pro Asp Pro Cys
    50                  55                  60

Gly Trp Thr Pro Ile Gln Gly Val Ser Cys Asp Phe Phe Asn Gly Phe
65                  70                  75                  80

Trp His Val Thr Asp Leu Ser Leu Gly Gln Val Tyr Asp Asn Ser Leu
                85                  90                  95

Asn Cys Ser Ser Thr Ala Glu Phe Gly Tyr His Leu Phe Glu Leu Lys
            100                 105                 110

Tyr Leu Arg Lys Leu Thr Phe Thr Asp Cys Phe Leu Ser Ser His Arg
        115                 120                 125

Lys Pro Val Lys Ile Pro Glu Ser Arg Trp Glu Arg Leu Ala Tyr Thr
    130                 135                 140

Leu Glu His Leu Glu Phe Arg Ser Asn Pro Gly Leu Thr Gly Gly Ile
145                 150                 155                 160

Pro Thr Ala Leu Gly Cys Leu Thr Lys Leu Glu Ser Leu Val Leu Ile
                165                 170                 175

Glu Asn Ala Leu Thr Gly Asn Cys Arg Leu Lys
            180                 185

<210> SEQ ID NO 20
<211> LENGTH: 3513
<212> TYPE: DNA
<213> ORGANISM: Zea mays

<400> SEQUENCE: 20

```
acaacgccag accgcctgcc tgtgcttgca gccaggccgg ccagctgcct gcctgcctgt      60
tgtcgtctgc ggcgcgacgg cggccgcccg gtcgaccgcc cgcattggga tccccagagc     120
agcgcttggc atagggaat gtcccgggtc agccaccgtc gcctctgcgc tgcgaaagcc      180
ccgcatttac ttgccaccta gaagggggca cccctcgcga gacccagcgc cagacagagc     240
cagcaatggc tgctgctgct gctcctcctc ctcctatata gcggggcccg tgccgagcgc     300
tcgatccagt tcttctgatc tctgacttct gagcgaggag tggacgagtg gtgtgccgtc     360
gtccggttcc cgttggtttg gcgatgaggc gcgctcgcgg tcgccgcggg ctgctgcttc     420
tcctcggcgt ggcgctctcg gcggctgcgc tgctccgtgg ctgcgcgggg cagcaagggg     480
aggacggctc ggacgcccct gcggcggcgg cggcggagac ggcccccatg gaggagaagg     540
agcgcagggc gctgtacgcc gccatcgaga gcttcgtcgg caaggggtgg aacggctccg     600
ggctctaccc agaccctgc ggctggtctc ccatccaggc gcgtccctgc ccttcctgcg      660
ctttcccttt cgcatcgatc tatgttaccg tgctgttcga ttttctggcc cgcgtatgtt     720
cgttcatcat gttcgttctt cagacgcgcg aagctttcct ctttggtttt tcggctttg     780
cccgtcctcg tcacacgccc tttctcggtg ctcccctgct gcctgctttg agctccaatc     840
caaaaaccgt tgcgagcga aaggaggagc aagtcggtag cctccgaaat gaaattggtg      900
ccctgtttgg ggatgcagga cgcacgccaa gtcgccacca aatctcctgc tgtaatttcc     960
cgtgttaaaa ccttcctcgt ctcgcttcca gaatttctgg ccttccggta gcctctgctg    1020
ttttttgtctt gtgttcgtcc ttcgtcgcac tcgtgccctg ctcctcaact gttgcttcga    1080
gattgtggca ctgttttgct gtgcgccgct gcacattcag ttcactgttg gacgagacct    1140
ctgcttgatc cccttgtgtc ttcgcatctc agccttttgc tcgatatggt aggaggatct    1200
gatctcttgg gcaggaactt tccactcaca tgaaaagaac ctcccatgat ttgaaatggc    1260
atgctccgcc caagattttt ctcatacagt actactactc tctagtatag attttagtag    1320
taccttgaca tcttcttcct tttgctcgcg cccgagaagg aatcagtcct actactccat    1380
aggagttttt gctctaacaa ttactggaat ttaccgcata tttatcttcc ttcacacggt    1440
acactggaat ttcattctgg ttgttacagt accagtaaag ttaagaaggg gccaaatttg    1500
tactaggtgc acctttaaga aatgtcgcca tcttggatca tcctcatcca tgtctgttat    1560
tactgctagt agttactgtt gagcttgtgt ttactttccg agtaggacac tctcagattg    1620
cagcgtgctt gcctgcctgt taaaattaag gggattcaat ttcagtggat tgagcagatg    1680
tggttcttgg atgccaaaaa cctgtgcagg gggtgtcatg tgatctcttc aatggcctgt    1740
ggtacccaac agtgatgagc attggcccag tccttgacaa ctcgctgcag tcggccccg     1800
acgccaagtt cagcgcccag ctgttcgacc tgaggcgcct ccggacgctg tctttctaca    1860
gctgcttccc ggcgagcaac cccacggcca tcccgaccgg cagctgggag aagctggcgg    1920
ggacgctgga gacgctggag ttccgcacca acccgggcct gaacggcgcc atcccggcgt    1980
ccctcggccg cctggccagc ctgcagtcgc tggtgctcgt ggacagtggc gaagctagag    2040
caaaatataa gggggtgcac gtctcttgtg ggtgcatagg aacaaaattt gggtgatgca    2100
tatatggtgg aaatttgact cttatcactg ttttttggat ttttgggggg tgcatatgca    2160
tccacagtgc acaacatagc ttcgcccctg ctcgtggaga caacctgac ggggcccgtg     2220
cccgcggagc tgggcgcgct gtcgaggctg agacggctgg tgctgtccgg gaacgggctg    2280
```

-continued

```
tcggggccga tcccggtgac actcggtaac gaccgccgcg ccgacgagct gctgctgatc    2340
gtggacctga gcaggaacta tctaaccggc tctctgcctt cgtcgctagg tggcctcacg    2400
gggctcctga agatggacct gagcagcaac ctgctgcagg gcagcatccc gccggagctc    2460
gcggggctca ggagcctcac gctgctggac ctcaggaaca acagcctcac cggcgggctg    2520
ccccagttcg tgcagggcat ggcgtcgctg caggacctgc tgctctcgaa caacccgctg    2580
ggcggcggcc tgccgcagtc cggctggggg gcgctggcgg cctggccac gctggacctg    2640 tccaacgtcg gcctcgtggg cgccataccg gggtccatgg cggccctgac ggggctccgg    2700
ttcctggcgc tggaccacaa ccgcctgacg ggggccgtgc cgcccgagct cgcccggctg    2760
cccagcatcg gcgcgctgta cctgaacggc aacaacctga cggggacgct ggagttctcg    2820
gccgggttct accagcgcat ggggcggcgg ttcgcgtcgt gggacaaccc cgggctgtgc    2880
tacaacgtcg cggccgtgga cgcggcccac cgcgccgtcgg gcgtggtggt gtgcaaggac    2940
ctgcaggagc ccagcgtggg cggcggcgcg cgggacgggg acgggacgg ggacgcggag    3000 gaggacggga cgaagcccga ggcgggctcc agcctcgtgg cctcctcgtc gtccggcatg    3060
ccggttggca gtgtcggtgg gctccggtac ctggtggtgg ttcggggaat ggcggctgcg    3120
gttcttgggt tggtgtccct cctacaatag caagcaagca ggttcagaag aagaacacgg    3180
agaaacttga agtaatgcta ggtaggttag cacgaagtag tttctgcgcg ttctctgtga    3240
tcttttggca tttgttttttg gctgctggtg gcttaccatc gtcagatggt gacggaggaa    3300
ggagggaaca tggatctgga tggtgtgagc cacagattac attacagtag tagagtaaac    3360
tatgagagtt cttgtggact gaaggtgtgt agtggtggat agggtagctt ctccggggtt    3420
cttttgtgtg taattagcct gtgtcgccct gtggtgtcat gttacaacag caagtggaaa    3480
tctaagctgg ttcgtccgtt gttggagaat cag    3513
```

<210> SEQ ID NO 21
<211> LENGTH: 213
<212> TYPE: PRT
<213> ORGANISM: Zea mays

<400> SEQUENCE: 21

```
Met Arg Arg Ala Arg Gly Arg Gly Leu Leu Leu Leu Gly Val
1               5                   10                  15

Ala Leu Ser Ala Ala Leu Leu Arg Gly Cys Ala Gly Gln Gln Gly
            20                  25                  30

Glu Asp Gly Ser Asp Ala Pro Ala Ala Ala Ala Glu Thr Ala Pro
        35                  40                  45

Met Glu Glu Lys Glu Arg Arg Ala Leu Tyr Ala Ala Ile Glu Ser Phe
    50                  55                  60

Val Gly Lys Gly Trp Asn Gly Ser Gly Leu Tyr Pro Asp Pro Cys Gly
65                  70                  75                  80

Trp Ser Pro Ile Gln Gly Val Ser Cys Asp Leu Phe Asn Gly Leu Trp
                85                  90                  95

Tyr Pro Thr Val Met Ser Ile Gly Pro Val Leu Asp Asn Ser Leu Gln
            100                 105                 110

Cys Gly Pro Asp Ala Lys Phe Ser Ala Gln Leu Phe Asp Leu Arg Arg
        115                 120                 125

Leu Arg Thr Leu Ser Phe Tyr Ser Cys Phe Pro Ala Ser Asn Pro Thr
    130                 135                 140

Ala Ile Pro Thr Gly Ser Trp Glu Lys Leu Ala Gly Thr Leu Glu Thr
145                 150                 155                 160
```

```
Leu Glu Phe Arg Thr Asn Pro Gly Leu Asn Gly Ala Ile Pro Ala Ser
            165                 170                 175

Leu Gly Arg Leu Ala Ser Leu Gln Ser Leu Val Leu Val Asp Ser Gly
        180                 185                 190

Glu Ala Arg Ala Lys Tyr Lys Gly Val His Val Ser Cys Gly Cys Ile
        195                 200                 205

Gly Thr Lys Phe Gly
    210
```

<210> SEQ ID NO 22
<211> LENGTH: 1521
<212> TYPE: DNA
<213> ORGANISM: Zea mays

<400> SEQUENCE: 22

```
atgaggcgcg ctcgcggtcg ccgcgggctg ctgcttctcc tcggcgtggc gctctcggcg      60
gctgcgctgc tccgtggctg cgcggggcag caaggggagg acggctcgga cgccctgcg     120
gcggcggcgg cggagacggc ccccatggag gagaaggagc gcagggcgct gtacgccgcc    180
atcgagagct tcgtcggcaa ggggtggaac ggctccgggc tctacccaga ccctgcggc     240
tggtctccca tccagggggt gtcatgtgat ctcttcaatg gcctgtggta cccaacagtg    300
atgagcattg gccagtcct tgacaactcg ctgcagtgcg ccccgacgc caagttcagc      360
gcccagctgt tcgacctgag gcgcctccgg acgctgtctt tctacagctg cttcccggcg    420
agcaaccccca ggccatccc gaccggcagc tgggagaagc tggcggggac gctggagacg    480
ctggagttcc gcaccaaccc gggcctgaac ggcgccatcc cggcgtccct cggccgcctg    540
gccagcctgc agtcgctggt gctcgtggag aacaacctga cggggcccgt gcccgcggag    600
ctgggcgcgc tgtcgaggct gagacggctg gtgctgtccg gaacgggct gtcggggccg     660
atcccggtga cactcggtaa cgaccgccgc cccgacgagc tgctgctgat cgtggacctg    720
agcaggaact atctaaccgg ctctctgcct tcgtcgctag gtggcctcac ggggctcctg    780
aagatggacc tgagcagcaa cctgctgcag ggcagcatcc cgccggagct cgcggggctc    840
aggagcctca cgctgctgga cctcaggaac aacagcctca ccggcgggct gccccagttc    900
gtgcagggca tggcgtcgct gcaggacctg ctgctctcga caaacccgct gggcggcggc    960
ctgccgcagt ccggctgggg ggcgctggcg ggcctggcca cgctgaacct gtccaacgtc   1020
ggcctcgtgg cgccataccc ggggtccatg gcggccctga cggggctccg gttcctggcg   1080
ctggaccaca accgctgac gggggccgtg ccgcccgagc tcgcccggct gcccagcatc    1140
ggcgcgctgt acctgaacgg caacaacctg acggggacgc tggagttctc ggccgggttc   1200
taccagcgca tgggggcggcg gttcgcgtcg tgggacaacc ccgggctgtg ctacaacgtc   1260
gcggccgtgg acgcggccca cgcgccgtcg ggcgtggtgg tgtgcaagga cctgcaggag   1320
cccagcgtgg cggcggcgc gcgggacggg gacgggacg ggacgcgga ggaggacggg      1380
acgaagcccg aggcgggctc cagcctcgtg gcctcctcgt cgtccggcat gccggttggc   1440
agtgtcggtg ggctccggta cctggtggtg gttcggggaa tggcggctgc ggttcttggg   1500
ttggtgtccc tcctacaata g                                             1521
```

<210> SEQ ID NO 23
<211> LENGTH: 506
<212> TYPE: PRT
<213> ORGANISM: Zea mays

-continued

```
<400> SEQUENCE: 23

Met Arg Arg Ala Arg Gly Arg Gly Leu Leu Leu Leu Gly Val
1               5                   10                  15

Ala Leu Ser Ala Ala Ala Leu Leu Arg Gly Cys Ala Gly Gln Gln Gly
            20                  25                  30

Glu Asp Gly Ser Asp Ala Pro Ala Ala Ala Ala Glu Thr Ala Pro
                35                  40                  45

Met Glu Glu Lys Glu Arg Arg Ala Leu Tyr Ala Ala Ile Glu Ser Phe
50                  55                  60

Val Gly Lys Gly Trp Asn Gly Ser Gly Leu Tyr Pro Asp Pro Cys Gly
65                  70                  75                  80

Trp Ser Pro Ile Gln Gly Val Ser Cys Asp Leu Phe Asn Gly Leu Trp
                85                  90                  95

Tyr Pro Thr Val Met Ser Ile Gly Pro Val Leu Asp Asn Ser Leu Gln
                100                 105                 110

Cys Gly Pro Asp Ala Lys Phe Ser Ala Gln Leu Phe Asp Leu Arg Arg
            115                 120                 125

Leu Arg Thr Leu Ser Phe Tyr Ser Cys Phe Pro Ala Ser Asn Pro Thr
    130                 135                 140

Ala Ile Pro Thr Gly Ser Trp Glu Lys Leu Ala Gly Thr Leu Glu Thr
145                 150                 155                 160

Leu Glu Phe Arg Thr Asn Pro Gly Leu Asn Gly Ala Ile Pro Ala Ser
                165                 170                 175

Leu Gly Arg Leu Ala Ser Leu Gln Ser Leu Val Leu Glu Asn Asn
            180                 185                 190

Leu Thr Gly Pro Val Pro Ala Glu Leu Gly Ala Leu Ser Arg Leu Arg
    195                 200                 205

Arg Leu Val Leu Ser Gly Asn Gly Leu Ser Gly Pro Ile Pro Val Thr
210                 215                 220

Leu Gly Asn Asp Arg Arg Ala Asp Glu Leu Leu Leu Ile Val Asp Leu
225                 230                 235                 240

Ser Arg Asn Tyr Leu Thr Gly Ser Leu Pro Ser Ser Leu Gly Gly Leu
                245                 250                 255

Thr Gly Leu Leu Lys Met Asp Leu Ser Ser Asn Leu Leu Gln Gly Ser
            260                 265                 270

Ile Pro Pro Glu Leu Ala Gly Leu Arg Ser Leu Thr Leu Leu Asp Leu
        275                 280                 285

Arg Asn Asn Ser Leu Thr Gly Gly Leu Pro Gln Phe Val Gln Gly Met
290                 295                 300

Ala Ser Leu Gln Asp Leu Leu Ser Asn Asn Pro Leu Gly Gly Gly
305                 310                 315                 320

Leu Pro Gln Ser Gly Trp Gly Ala Leu Ala Gly Leu Ala Thr Leu Asn
                325                 330                 335

Leu Ser Asn Val Gly Leu Val Gly Ala Ile Pro Gly Ser Met Ala Ala
            340                 345                 350

Leu Thr Gly Leu Arg Phe Leu Ala Leu Asp His Asn Arg Leu Thr Gly
    355                 360                 365

Ala Val Pro Pro Glu Leu Ala Arg Leu Pro Ser Ile Gly Ala Leu Tyr
370                 375                 380

Leu Asn Gly Asn Asn Leu Thr Gly Thr Leu Glu Phe Ser Ala Gly Phe
385                 390                 395                 400

Tyr Gln Arg Met Gly Arg Arg Phe Ala Ser Trp Asp Asn Pro Gly Leu
                405                 410                 415
```

```
Cys Tyr Asn Val Ala Val Asp Ala His Ala Pro Ser Gly Val
            420                 425                 430

Val Val Cys Lys Asp Leu Gln Glu Pro Ser Val Gly Gly Ala Arg
                435                 440                 445

Asp Gly Asp Gly Asp Gly Asp Ala Glu Glu Asp Gly Thr Lys Pro Glu
    450                 455                 460

Ala Gly Ser Ser Leu Val Ala Ser Ser Ser Gly Met Pro Val Gly
465                 470                 475                 480

Ser Val Gly Gly Leu Arg Tyr Leu Val Val Val Arg Gly Met Ala Ala
                485                 490                 495

Ala Val Leu Gly Leu Val Ser Leu Leu Gln
            500                 505

<210> SEQ ID NO 24
<211> LENGTH: 1521
<212> TYPE: DNA
<213> ORGANISM: Zea mays

<400> SEQUENCE: 24
```

| | | | | | |
|---|---|---|---|---|---|
| atgaggcgcg | ctcgcggtcg | ccgcgggctg | ctgcttctcc | tcggcgtggc | gctctcggcg | 60 |
| gctgcgctgc | tccgtggctg | cgcggggcag | caaggggagg | acggctcgga | cgcccctgcg | 120 |
| gcggcggcgg | cggagacggc | ccccatggag | gagaaggagc | gcaggggcgct | gtacgccgcc | 180 |
| atcgagagct | tcgtcggcaa | ggggtggaac | ggctccgggc | tctacccaga | cccctgcggc | 240 |
| tggtctccca | tccagggggt | gtcatgtgat | ctcttcaatg | gcctgtggta | cccaacagtg | 300 |
| atgagcattg | gcccagtcct | tgacaactcg | ctgcagtgcg | gccccgacgc | caagttcagc | 360 |
| gcccagctgt | tcgacctgag | cgcctccgg | acgctgtctt | tctacagctg | cttcccggcg | 420 |
| agcaacccca | cggccatccc | gaccggcagc | tgggagaagc | tggcggggac | gctggagacg | 480 |
| ctggagttcc | gcaccaaccc | gggcctgaac | ggcgccatcc | cggcgtccct | cggccgcctg | 540 |
| gccagcctgc | agtcgctggt | gctcgtggag | aacaacctga | cggggcccgt | gccgcggag | 600 |
| ctgggcgcgc | tgtcgaggct | gagacggctg | gtgctgtccg | ggaacgggct | gtcggggccg | 660 |
| atcccggtga | cactcggtaa | cgaccgccgc | ccgacgagc | tgctgctgat | cgtggacctg | 720 |
| agcaggaact | atctaaccgg | ctctctgcct | tcgtcgctag | gtggcctcac | ggggctcctg | 780 |
| aagatggacc | tgagcagcaa | cctgctgcag | ggcagcatcc | cgccggagct | cgcggggctc | 840 |
| aggagcctca | cgctgctgga | cctcaggaac | aacagcctca | ccggcgggct | gccccagttc | 900 |
| gtgcagggca | tggcgtcgct | gcaggacctg | ctgctctcga | caacccgct | gggcggcggc | 960 |
| ctgccgcagt | ccggctgggg | ggcgctggcg | ggcctggcca | cgctggacct | gtccaacgtc | 1020 |
| ggcctcgtgg | gcgccatacc | ggggtccatg | gcggccctga | cggggctccg | gttcctggcg | 1080 |
| ctggaccaca | accgcctgac | gggggccgtg | ccgcccgagc | tcgcccggct | gccccagcatc | 1140 |
| ggcgcgctgt | acctgaacgg | caacaacctg | acggggacgc | tggagttctc | ggccgggttc | 1200 |
| taccagcgca | tggggcggcg | gttcgcgtcg | tgggacaacc | ccgggctgta | ctacaacgtc | 1260 |
| gcggccgtgg | acgcgcccca | cgcgccgtcg | ggcgtggtgg | tgtgcaagga | cctgcaggag | 1320 |
| cccagcgtgg | gcggcggcgc | gcgggacggg | gacgggacg | gggacgcgga | ggaggacggg | 1380 |
| acgaagcccg | aggcgggctc | cagcctcgtg | gcctcctcgt | cgtccggcat | gccggttggc | 1440 |
| agtgtcggtg | ggctccggta | cctggtggtg | gttcggggaa | tggcggctgc | ggttcttggg | 1500 |
| ttggtgtccc | tcctacaata | g | | | | 1521 |

<210> SEQ ID NO 25
<211> LENGTH: 506
<212> TYPE: PRT
<213> ORGANISM: Zea mays

<400> SEQUENCE: 25

```
Met Arg Arg Ala Arg Gly Arg Gly Leu Leu Leu Leu Gly Val
1               5                   10                  15

Ala Leu Ser Ala Ala Leu Leu Arg Gly Cys Ala Gly Gln Gln Gly
            20                  25                  30

Glu Asp Gly Ser Asp Ala Pro Ala Ala Ala Ala Glu Thr Ala Pro
            35                  40                  45

Met Glu Glu Lys Glu Arg Arg Ala Leu Tyr Ala Ala Ile Glu Ser Phe
50                  55                  60

Val Gly Lys Gly Trp Asn Gly Ser Gly Leu Tyr Pro Asp Pro Cys Gly
65                  70                  75                  80

Trp Ser Pro Ile Gln Gly Val Ser Cys Asp Leu Phe Asn Gly Leu Trp
                    85                  90                  95

Tyr Pro Thr Val Met Ser Ile Gly Pro Val Leu Asp Asn Ser Leu Gln
                100                 105                 110

Cys Gly Pro Asp Ala Lys Phe Ser Ala Gln Leu Phe Asp Leu Arg Arg
            115                 120                 125

Leu Arg Thr Leu Ser Phe Tyr Ser Cys Phe Pro Ala Ser Asn Pro Thr
130                 135                 140

Ala Ile Pro Thr Gly Ser Trp Glu Lys Leu Ala Gly Thr Leu Glu Thr
145                 150                 155                 160

Leu Glu Phe Arg Thr Asn Pro Gly Leu Asn Gly Ala Ile Pro Ala Ser
                165                 170                 175

Leu Gly Arg Leu Ala Ser Leu Gln Ser Leu Val Leu Val Glu Asn Asn
            180                 185                 190

Leu Thr Gly Pro Val Pro Ala Glu Leu Gly Ala Leu Ser Arg Leu Arg
            195                 200                 205

Arg Leu Val Leu Ser Gly Asn Gly Leu Ser Gly Pro Ile Pro Val Thr
210                 215                 220

Leu Gly Asn Asp Arg Arg Ala Asp Glu Leu Leu Ile Val Asp Leu
225                 230                 235                 240

Ser Arg Asn Tyr Leu Thr Gly Ser Leu Pro Ser Ser Leu Gly Gly Leu
                245                 250                 255

Thr Gly Leu Leu Lys Met Asp Leu Ser Ser Asn Leu Leu Gln Gly Ser
            260                 265                 270

Ile Pro Pro Glu Leu Ala Gly Leu Arg Ser Leu Thr Leu Leu Asp Leu
            275                 280                 285

Arg Asn Asn Ser Leu Thr Gly Gly Leu Pro Gln Phe Val Gln Gly Met
290                 295                 300

Ala Ser Leu Gln Asp Leu Leu Ser Asn Asn Pro Leu Gly Gly Gly
305                 310                 315                 320

Leu Pro Gln Ser Gly Trp Gly Ala Leu Ala Gly Leu Ala Thr Leu Asp
                325                 330                 335

Leu Ser Asn Val Gly Leu Val Gly Ala Ile Pro Gly Ser Met Ala Ala
            340                 345                 350

Leu Thr Gly Leu Arg Phe Leu Ala Leu Asp His Asn Arg Leu Thr Gly
            355                 360                 365

Ala Val Pro Pro Glu Leu Ala Arg Leu Pro Ser Ile Gly Ala Leu Tyr
370                 375                 380
```

```
Leu Asn Gly Asn Asn Leu Thr Gly Thr Leu Glu Phe Ser Ala Gly Phe
385                 390                 395                 400

Tyr Gln Arg Met Gly Arg Arg Phe Ala Ser Trp Asp Asn Pro Gly Leu
            405                 410                 415

Tyr Tyr Asn Val Ala Ala Val Asp Ala Ala His Ala Pro Ser Gly Val
            420                 425                 430

Val Val Cys Lys Asp Leu Gln Glu Pro Ser Val Gly Gly Gly Ala Arg
            435                 440                 445

Asp Gly Asp Gly Asp Gly Asp Ala Glu Glu Asp Gly Thr Lys Pro Glu
            450                 455                 460

Ala Gly Ser Ser Leu Val Ala Ser Ser Ser Gly Met Pro Val Gly
465                 470                 475                 480

Ser Val Gly Gly Leu Arg Tyr Leu Val Val Arg Gly Met Ala Ala
                485                 490                 495

Ala Val Leu Gly Leu Val Ser Leu Leu Gln
            500                 505

<210> SEQ ID NO 26
<211> LENGTH: 1521
<212> TYPE: DNA
<213> ORGANISM: Zea mays

<400> SEQUENCE: 26
atgaggcgcg ctcgcggtcg ccgcgggctg ctgcttctcc tcggcgtggc gctctcggcg     60
gctgcgctgc tccgtggctg cgcggggcag caaggggagg acggctcgga cgcccctgcg    120
gcggcggcgg cggagacggc ccccatggag gagaaggagc gcagggcgct gtacgccgcc    180
atcgagagct tcgtcggcaa ggggtggaac ggctccgggc tctacccaga ccccctgcgg    240
tggtctccca tccagggggt gtcatgtgat ctcttcaatg gcctgtggta cccaacagtg    300
atgagcattg gcccagtcct tgacaactcg ctgcagtgcg ccccgacgc caagttcagc     360 gcccagctgt tcgacctgag cgcctccgg acgctgtctt tctacagctg cttcccggcg    420 agcaaccccca cggccatccc gaccggcagc tgggagaagc tggcggggac gctggagacg    480
ctggagttcc gcaccaaccc gggcctgaac ggcgccatcc cggcgtccct cggccgcctg    540
gccagcctgc agtcgctggt gctcgtggag aacaacctga cggggcccgt gcccgcggag    600
ctgggcgcgc tgtcgaggct gagacggctg gtgctgtccg gaacgggct gtcggggccg    660 atcccggtga cactcggtaa cgaccgccgc ccgacgagc tgctgctgat cgtggacctg    720
agcaggaact atctaaccgg ctctctgcct tcgtcgctag gtggcctcac ggggctcctg    780
aagatggacc tgagcagcaa cctgctgcag ggcagcatcc cgccggagct cgcggggctc    840
aggagcctca cgctgctgga cctcaggaac aacagcctca ccggcgggct gccccagttc    900
gtgcagggca tggcgtcgct gcaggacctg ctgctctcga caacccgct gggcggcggc    960 ctgccgcagt ccggctgggg ggcgctggcg gcctggcca cgctggacct gtccaacgtc   1020
ggcctcgtgg gcgccatacc ggggtccatg gcggccctga cggggctccg gttcctggcg   1080
ctggaccaca accgcctgac gggggccgtg ccgcccgagc tcgcccggct gcccagcatc   1140
ggcgcgctgt acctgaacgg caacaacctg acggggacgc tggagttctc ggccgggttc   1200
taccagcgca tggggcggcg gttcgcgtcg tgggacaacc ccgggctgtg ctacaacgtc   1260
gcggccgtgg acgcggccca cgcgccgtcg ggcgtggtgg tgtacaagga cctgcaggag   1320
cccagcgtgg gcggcggcgc gcgggacggg gacggggacg gggacgcgga ggaggacggg   1380
```

-continued

```
acgaagcccg aggcgggctc cagcctcgtg gcctcctcgt cgtccggcat gccggttggc      1440
agtgtcggtg ggctccggta cctggtggtg gttcggggaa tggcggctgc ggttcttggg      1500
ttggtgtccc tcctacaata g                                                1521
```

<210> SEQ ID NO 27
<211> LENGTH: 506
<212> TYPE: PRT
<213> ORGANISM: Zea mays
<400> SEQUENCE: 27

```
Met Arg Arg Ala Arg Gly Arg Gly Leu Leu Leu Leu Gly Val
1               5                  10                  15

Ala Leu Ser Ala Ala Leu Leu Arg Gly Cys Ala Gly Gln Gln Gly
            20                  25                  30

Glu Asp Gly Ser Asp Ala Pro Ala Ala Ala Ala Glu Thr Ala Pro
        35                  40                  45

Met Glu Glu Lys Glu Arg Arg Ala Leu Tyr Ala Ala Ile Glu Ser Phe
    50                  55                  60

Val Gly Lys Gly Trp Asn Gly Ser Gly Leu Tyr Pro Asp Pro Cys Gly
65                  70                  75                  80

Trp Ser Pro Ile Gln Gly Val Ser Cys Asp Leu Phe Asn Gly Leu Trp
                85                  90                  95

Tyr Pro Thr Val Met Ser Ile Gly Pro Val Leu Asp Asn Ser Leu Gln
            100                 105                 110

Cys Gly Pro Asp Ala Lys Phe Ser Ala Gln Leu Phe Asp Leu Arg Arg
        115                 120                 125

Leu Arg Thr Leu Ser Phe Tyr Ser Cys Phe Pro Ala Ser Asn Pro Thr
    130                 135                 140

Ala Ile Pro Thr Gly Ser Trp Glu Lys Leu Ala Gly Thr Leu Glu Thr
145                 150                 155                 160

Leu Glu Phe Arg Thr Asn Pro Gly Leu Asn Gly Ala Ile Pro Ala Ser
                165                 170                 175

Leu Gly Arg Leu Ala Ser Leu Gln Ser Leu Val Leu Glu Asn Asn
            180                 185                 190

Leu Thr Gly Pro Val Pro Ala Glu Leu Gly Ala Leu Ser Arg Leu Arg
    195                 200                 205

Arg Leu Val Leu Ser Gly Asn Gly Leu Ser Gly Ile Pro Val Thr
210                 215                 220

Leu Gly Asn Asp Arg Arg Ala Asp Glu Leu Leu Leu Ile Val Asp Leu
225                 230                 235                 240

Ser Arg Asn Tyr Leu Thr Gly Ser Leu Pro Ser Ser Leu Gly Gly Leu
                245                 250                 255

Thr Gly Leu Leu Lys Met Asp Leu Ser Ser Asn Leu Leu Gln Gly Ser
            260                 265                 270

Ile Pro Pro Glu Leu Ala Gly Leu Arg Ser Leu Thr Leu Leu Asp Leu
        275                 280                 285

Arg Asn Asn Ser Leu Thr Gly Gly Leu Pro Gln Phe Val Gln Gly Met
    290                 295                 300

Ala Ser Leu Gln Asp Leu Leu Ser Asn Asn Pro Leu Gly Gly Gly
305                 310                 315                 320

Leu Pro Gln Ser Gly Trp Gly Ala Leu Ala Gly Leu Ala Thr Leu Asp
                325                 330                 335

Leu Ser Asn Val Gly Leu Val Gly Ala Ile Pro Gly Ser Met Ala Ala
            340                 345                 350
```

```
Leu Thr Gly Leu Arg Phe Leu Ala Leu Asp His Asn Arg Leu Thr Gly
            355                 360                 365

Ala Val Pro Pro Glu Leu Ala Arg Leu Pro Ser Ile Gly Ala Leu Tyr
    370                 375                 380

Leu Asn Gly Asn Leu Thr Gly Thr Leu Glu Phe Ser Ala Gly Phe
385                 390                 395                 400

Tyr Gln Arg Met Gly Arg Arg Phe Ala Ser Trp Asp Asn Pro Gly Leu
                405                 410                 415

Cys Tyr Asn Val Ala Ala Val Asp Ala Ala His Ala Pro Ser Gly Val
            420                 425                 430

Val Val Tyr Lys Asp Leu Gln Glu Pro Ser Val Gly Gly Gly Ala Arg
            435                 440                 445

Asp Gly Asp Gly Asp Gly Asp Ala Glu Glu Asp Gly Thr Lys Pro Glu
450                 455                 460

Ala Gly Ser Ser Leu Val Ala Ser Ser Ser Gly Met Pro Val Gly
465                 470                 475                 480

Ser Val Gly Gly Leu Arg Tyr Leu Val Val Val Arg Gly Met Ala Ala
                485                 490                 495

Ala Val Leu Gly Leu Val Ser Leu Leu Gln
            500                 505

<210> SEQ ID NO 28
<211> LENGTH: 3426
<212> TYPE: DNA
<213> ORGANISM: Zea mays

<400> SEQUENCE: 28
aattcatcat ccgatggtaa cgaggaagat gttttagctg tgggtgaaaa tagcacaccg      60
aacccaagca ttgtacttaa aggaagcgca aggtgtttca tgactctctg aagcctagga    120 tgaaaagaa acatagggat gactacatga aaggattgt cgatgccttt gagtcgagga      180
cctttagctc gaacaagacc atttcatcct atgacaatga tccggtgtgt aaggaggttg    240
ctgctcaatt gaagaatgtc atccaagatg gtgcaaccga aggaagcgac ttgcatttct    300
tcgcaactca attattaata gacaaacatc atcgggatgc ctttgcaact cttgagacaa    360
aggaaggaag gaacgcttgg cttcgtcgcg cgtacgataa tcatgacaag tcgagttagg    420
tcatttgttc ctgttggtgc cctggagctg aagcaaaatg tttcatgtta cggtagtct    480 atagactgtt tggtgttctc gatcgtctat tttactttt ctagaactgt tggtcgttta    540
agtttgttat ctattggagt actgattcca tttttcggtt gaggtctttg ttttgaataa    600
aaacacttga gagtgacagt ggttatttgt atatgctaga gcaatagtgg ttatttgttg    660
ttaaacaatt tcagtactgt ttaaacgttt ctaatatgtg tttgcttcca tgtgtgctac    720
tggtaattag tattctatgc cacaattgta ttctggatga attaaacact agtatacttc    780
ttgtgtgtct gtagatggtg tagacaaatg atgaacaaaa tgatgacgaa attcatgagg    840
aatttatggt cgttgtagtt gcattggaga tgtgggggac tcctcagacg tggttgtacg    900
acaaccaatg gcagaaacat gtatacactg ggtcgatata accttagaga gtagtaatga    960
ttgctacgtc atgtttcgca tgcgtcggac tgtctttcat cgacttcatg acacattggt   1020
caacaattat ggtctagtag cgagtcaccg agttagtacg aaggaggcgc ttgctatttt   1080
tctgtgggcg tgcggggggg gttaatcatt tcgagagata ataataagt ttggccattc    1140 attggaaact ataaaccata aatttagtga agtacttgac gcaatatata ggatgtccaa    1200
```

```
cgacgcgact aagcccaagg atgcccattt cactaatatt cacccaagac tacgggaggc    1260
tcggtttgac cacatttcaa ggactacata ggagctatcg ttggaagcca ttttcccgcc    1320
tctgtccctt tgtcggagca accaaaatat attggtcgtc acgggtacac atcgcagaat    1380
gtcatgatca tttgtgagtt cgaaatgagg tacacattta tcatcactgg ttggcctcgt    1440
tccgtgcatg atactagagt gctacaagat actctgatca cgtacgacga taggttcccg    1500
cattcttcag aagatattac tccaatctac gtctgtagta tttcgaagtc acctcgttat    1560
gtatgacctt aaccatgata atttttatatt tcaggaaaat attatcttgt tgattcgggg   1620
tacctcaata ggacgggata ccttgcacct tataaaggtc aaaagtacca cattttcgaa    1680
tttaaggatg aaggcaacc tgttgctacc aaagaggttt tcaactatgc gcacttgttc     1740
ccgaggaata ttatagagca atcattttgg gtgcccaaga taaattggag aattcttatt    1800
agcctacctt cattttcact gagaaagcaa tccaagataa ttatatcatg catgatgtta    1860
cataacttca ttcgggacag tgttttacac tttcgcgact tcgattagta tatacctgca    1920
tgaggcatgt tcaggatgta gctataggtg agagtagtag caacacgtag atgagttaga    1980
catatgtgct tttagagatt caagtgctaa tgtgttagtg tcatagttag ttatccgtac    2040
gagtaaataa acatgttgta atggacaaat catgtggtaa tttctaatta ggtgctaatt    2100
agtatgtatg ttttttcttt ttttcatttt ctactatctt agaatcagtc tatccaaaca    2160
cctaaattct aaccaccagc ttcttcccat agcacctaaa ccaaatactc agattcttct    2220
tcttcatagt cagattctct ctacaaccat ttttttcaaaa aagctgaatc aaacagactc    2280
atagacacac gatgttcttg tctattttta tctttagtac tagtttgaca attctattta    2340
aaaaaaacta ttttctcgag ataaattagc tggaaatctc ttagactaac tccaacagag    2400
cagccaaagc caatatggct gtcgtggtgc tactgtagcg cctagaaaca ggttccaaca    2460
acacagccaa aaggagcagc tattttagag gggatgagag agaaaagcta gattggctgg    2520
ttcagagccg gcagccattt tctccccttc gtctctgaca atccggaccc acttctgagg    2580
cttctggcca ctcgccctgg gaaccagcta ttttagctgc tccgttggat acgaaggacg    2640
tatggatggc cagctaaatt actgtggcaa gccaacggcc tgaatgtctg cccgttttgg    2700
ctagtgcctg ttggagacag ccttaggagt tgacaaacta ggggctagtt tggatcggca    2760
cgccggcggc cacgccgcgc cacacctgtg gcgctgaaaa cgagcgccac actggtggcg    2820
tgggaagtgt ggcgggcggc ggcggcttag gcggccatcc aaacatcccc tagaccttaa    2880
ccaaacattc ctcccttctc gcttgtgtgt aacacccact ccgtattttt caccagcgcc    2940
accacggtaa agtgcacgct gttcctgcgg gacattacta caaaaccaat ccccgtcttt    3000
gcgaggtcgc gagtctctcc aactccgtcc ctctggcctc agcacaacgc cagaccgcct    3060
gcctgtgctt gcagccaggc cggccagctg cctgcctgcc tgttgtcgtc tgcggcgcga    3120
cggcggccgc ccggtcgacc gcccgcattg ggatccccag agcagcgctt ggcatagggg    3180
aatgtcccgg gtcagccacc gtcgcctctg cgctgcgaaa gccccgcatt tacttgccac    3240
ctagaagggg gcaccctcg cgagacccag cgccagacag agccagcaat ggctgctgct     3300
gctgctcctc ctcctcctat atagcggggc ccgtgccgag cgctcgatcc agttcttctg    3360
atctctgact tctgagcgag gagtggacga gtggtgtgcc gtcgtccggt tcccgttggt    3420
ttggcg                                                              3426
```

<210> SEQ ID NO 29
<211> LENGTH: 111

```
<212> TYPE: DNA
<213> ORGANISM: Zea mays

<400> SEQUENCE: 29
atgaggcgcg ctcgcggtcg ccgcgggctg ctgcttctcc tcggcgtggc gctctcggcg      60
gctgcgctgc tccgtggctg cgcggggcag caaggggagg acggctcgga c              111

<210> SEQ ID NO 30
<211> LENGTH: 3282
<212> TYPE: DNA
<213> ORGANISM: Artificial Sequence
<220> FEATURE:
<223> OTHER INFORMATION: Encodes RFP-FEA3 fusion protein

<400> SEQUENCE: 30
acaactttgt atacaaaagt tgcaggccgg cctggaggtg gaggtggagc tgcctcctcc      60
gaggacgtca tcaaggagtt catgcgcttc aaggtgcgca tggagggctc cgtgaacggc     120
cacgagttcg agatcgaggg cgagggcgag ggccgcccct acgagggcac ccagaccgcc     180
aagctgaagg tgaccaaggg cggccccctg cccttcgcct gggacatcct gtcccctcag     240
ttccagtacg gctccaaggc ctacgtgaag caccccgccg acatcccccga ctacttgaag     300 ctgtccttcc ccgagggctt caagtgggag cgcgtgatga acttcgagga cggcggcgtg     360
gtgaccgtga cccaggactc ctccctgcag gacggcgagt tcatctacaa ggtgaagctg     420
cgcggcacca acttccctc cgacggcccc gtaatgcaga agaagaccat gggctgggag     480
gcctccaccg agcggatgta ccccgaggac ggcgccctga agggcgagat caagatgagg     540
ctgaagctga aggacggcgg ccactacgac gccgaggtca agaccaccta catggccaag     600
aagcccgtgc agctgcccgg cgcctacaag accgacatca gctggacat cacctcccac     660 aacgaggact acaccatcgt ggaacagtac gagcgcgccg agggccgcca ctccaccggc     720
gccgatcctg ctggtgctgc tgcggccgct ggggcccacc caacttttct atacaaagtt     780
gcacaagggg aggacggctc ggacgcccct gcggcggcg cggcggagac ggcccccatg     840
gaggagaagg agcgcagggc gctgtacgcc gccatcgaga gcttcgtcgg caaggggtgg     900
aacggctccg ggctctaccc agaccctgc ggctggtctc ccatccaggc gcgtccctgc     960
ccttcctgcg ctttcccttt cgcatcgatc tatgttaccg tgctgttcga ttttctggcc    1020
cgcgtatgtt cgttcatcat gttcgttctt cagacgcgcg aagctttcct ctttggtttt    1080
ttcggctttg cccgtcctcg tcacacgccc tttctcggtg ctcccctgct gcctgctttg    1140
agctccaatc caaaaaccgt ttgcgagcga aaggaggagc aagtcggtag cctccgaaat    1200
gaaattggtg ccctgtttgg ggatgcagga cgcacgccaa gtcgccacca aatctcctgc    1260
tgtaatttcc cgtgttaaaa ccttcctcgt ctcgcttcca gaattctctgg ccttccggta    1320 gcctctgctg ttttttgtctt gtgttcgtcc ttcgtcgcac tcgtgccctg ctcctcaact    1380
gttgcttcga gattgtggca ctgttttgct gtgcgccgct gcacattcag ttcactgttg    1440
gacgagacct ctgcttgatc cccttgtgtc ttcgcatctc agccttttgc tcgatatggt    1500
aggaggatct gatctcttgg gcaggaactt tccactcaca tgaaaagaac ctcccatgat    1560
ttgaaatggc atgctccgcc caagattttt ctcatacagt actactactc tctagtatag    1620
attttagtag taccttgaca tcttcttcct tttgctcgcg cccgagaagg aatcagtcct    1680
actactccat aggagttttt gctctaacaa ttactgaat ttaccgcata tttatcttcc    1740
ttcacacggt acactggaat tcattctgg ttgttacagt accagtaaag ttaagaaggg    1800
```

| | |
|---|---|
| gccaaatttg tactaggtgc acctttaaga aatgtcgcca tcttggatca tcctcatcca | 1860 |
| tgtctgttat tactgctagt agttactgtt gagcttgtgt ttactttccg agtaggacac | 1920 |
| tctcagattg cagcgtgctt gcctgcctgt taaaattaag gggattcaat ttcagtggat | 1980 |
| tgagcagatg tggttcttgg atgccaaaaa cctgtgcagg gggtgtcatg tgatctcttc | 2040 |
| aatggcctgt ggtacccaac agtgatgagc attgggccag tccttgacaa ctcgctgcag | 2100 |
| tgcggccccg acgccaagtt cagcgcccag ctgttcgacc tgaggcgcct ccggacgctg | 2160 |
| tctttctaca gctgcttccc ggcgagcaac cccacggcca tcccgaccgg cagctgggag | 2220 |
| aagctggcgg ggacgctgga gacgctggag ttccgcacca acccgggcct gaacggcgcc | 2280 |
| atcccggcgt ccctcggccg cctggccagc ctgcagtcgc tggtgctcgt ggagaacaac | 2340 |
| ctgacggggc ccgtgcccgc ggagctgggc gcgctgtcga ggctgagacg gctggtgctg | 2400 |
| tccgggaacg ggctgtcggg gccgatcccg gtgacactcg gtaacgaccg ccgcgccgac | 2460 |
| gagctgctgc tgatcgtgga cctgagcagg aactatctaa ccggctctct gccttcgtcg | 2520 |
| ctaggtggcc tcacggggct cctgaagatg gacctgagca gcaacctgct gcagggcagc | 2580 |
| atcccgccgg agctcgcggg gctcaggagc ctcacgctgc tggacctcag gaacaacagc | 2640 |
| ctcaccggcg ggctgcccca gttcgtgcag ggcatggcgt cgctgcagga cctgctgctc | 2700 |
| tcgaacaacc cgctgggcgg cggcctgccg cagtccggct gggggcgct ggcgggcctg | 2760 |
| gccacgctgg acctgtccaa cgtcggcctc gtgggcgcca taccgggtc catggcggcc | 2820 |
| ctgacggggc tccggttcct ggcgctggac acaaccgcc tgacggggc cgtgccgccc | 2880 |
| gagctcgccc ggctgcccag catcggcgcg ctgtacctga acggcaacaa cctgacgggg | 2940 |
| acgctggagt tctcggccgg gttctaccag cgcatggggc ggcggttcgc gtcgtgggac | 3000 |
| aaccccgggc tgtgctacaa cgtcgcggcc gtggacgcgg cccacgcgcc gtcgggcgtg | 3060 |
| gtggtgtgca aggacctgca ggagcccagc gtgggcggcg gcgcgcggga cggggacggg | 3120 |
| gacggggacg cggaggagga cgggacgaag cccgaggcgg gctccagcct cgtggcctcc | 3180 |
| tcgtcgtccg gcatgccggt tggcagtgtc ggtgggctcc ggtacctggt ggtggttcgg | 3240 |
| ggaatggcgg ctgcggttct tgggttggtg tccctcctac aa | 3282 |

<210> SEQ ID NO 31
<211> LENGTH: 1295
<212> TYPE: DNA
<213> ORGANISM: Zea mays

<400> SEQUENCE: 31

| | |
|---|---|
| tagcaagcaa gcaggttcag aagaagaaca cggagaaact tgaagtaatg ctaggtaggt | 60 |
| tagcacgaag tagtttctgc gcgttctctg tgatcttttg gcatttgttt ttggctgctg | 120 |
| gtggcttacc atcgtcagat ggtgacggag gaaggaggga acatggatct ggatggtgtg | 180 |
| agccacagat tacattacag tagtagagta aactatgaga gttcttgtgg actgaaggtg | 240 |
| tgtagtggtg datagggtag cttctccggg gttcttttgt gtgtaattag cctgtgtcgc | 300 |
| cctgtggtgt catgttacaa cagcaagtgg aaatctaagc tggttcgtcc gttgttggag | 360 |
| aatcagaaaa aaaaaaattg tcgtgcttca ttcacatcac atggatacac agtttcctgt | 420 |
| tcttggagca gaagaactgg aaagatctct cgttatctct atttgctata gaaagaacat | 480 |
| agcggcggta tctgcagacg atacaaatgg aagaagagcg ggcaagcagc acgacaggat | 540 |
| ggagcggcg cgccgccgca tatgtccggc tgccgcctgc cggcgatctc ggtgtctcct | 600 |
| gctgcctttt gcctttgcgt gttctcgagt ctgaaaataa aatcaaaaat atggaccgag | 660 |

```
acgctgattg cgcagggccc cgcgctcgca gaggagtcag aaacagaaag gacctgtcac    720
cttggaaagc tggcggccgg agcggagccc tcacagacag gctgcgctct gcctctctgg    780
cactggcagg cggcagcggc agtagcgcta gtcctctaca ggtggaggct ggactgcacc    840
tcgacgtgta ggaactgtag cgtcattgtg gtactccggc gtctgtaccg gtctactcta    900
cacttttcca tcccagtacg ctttgaaata tttacaaaaa ataaatgtat ttaatgatga    960
tatcactagc tctagttgtc ttttttttta tttatcttc tcttaaaata caacaagtac    1020
actattatag atatataatt tatcactaac attatttatt ttgaaaacga gggagcaccg    1080
gagcagtact ctgtactcct agtgctacgc aatggcgcgg tggcaccacg caccaggcac    1140
cagcctgcgg gtgcaggtat aggcgtgcta gcacctagca gtatggggtt gggctgcacg    1200
tcgcagtact agcgcgtaga agcaatcgat gctctcgccg aaaaacaaag gcacaggatc    1260
agtggcacag ctcgtaatac aattgtcgtt tcctc                              1295
```

<210> SEQ ID NO 32
<211> LENGTH: 12
<212> TYPE: PRT
<213> ORGANISM: Zea mays

<400> SEQUENCE: 32

Arg Pro Val Pro Ser Gly Pro Asp Pro Ile His His
1               5                   10

<210> SEQ ID NO 33
<211> LENGTH: 12
<212> TYPE: PRT
<213> ORGANISM: Oryza sativa

<400> SEQUENCE: 33

Arg Glu Val Pro Thr Gly Pro Asp Pro Ile His His
1               5                   10

<210> SEQ ID NO 34
<211> LENGTH: 12
<212> TYPE: PRT
<213> ORGANISM: Arabidopsis thaliana

<400> SEQUENCE: 34

Arg Thr Val Pro Ser Gly Pro Asp Pro Leu His His
1               5                   10

<210> SEQ ID NO 35
<211> LENGTH: 12
<212> TYPE: PRT
<213> ORGANISM: Arabidopsis thaliana

<400> SEQUENCE: 35

Arg Lys Val Lys Thr Gly Ser Asn Pro Leu His Asn
1               5                   10

<210> SEQ ID NO 36
<211> LENGTH: 12
<212> TYPE: PRT
<213> ORGANISM: Arabidopsis thaliana

<400> SEQUENCE: 36

Arg Gln Val Pro Thr Gly Ser Asp Pro Leu His His
1               5                   10

```
<210> SEQ ID NO 37
<211> LENGTH: 12
<212> TYPE: PRT
<213> ORGANISM: Zea mays

<400> SEQUENCE: 37

Arg Leu Val Pro Gln Gly Pro Asn Pro Leu His Asn
1               5                   10

<210> SEQ ID NO 38
<211> LENGTH: 12
<212> TYPE: PRT
<213> ORGANISM: Zea mays

<400> SEQUENCE: 38

Arg Arg Ile Pro Thr Gly Pro Asn Pro Leu His Asn
1               5                   10
```